(12) United States Patent
Rodriguez-Navarro et al.

(10) Patent No.: US 11,730,476 B2
(45) Date of Patent: Aug. 22, 2023

(54) LAPAROSCOPIC GRASPERS AND SYSTEMS THEREFOR

(71) Applicant: Levita Magnetics International Corp., San Mateo, CA (US)

(72) Inventors: Alberto Rodriguez-Navarro, San Francisco, CA (US); Mariel Fabro, San Francisco, CA (US); Archana Nair, Eden Prairie, MN (US); Olgy Datto, Baton Rouge, LA (US)

(73) Assignee: LEVITA MAGNETICS INTERNATIONAL CORP., Menlo Park, CA (US)

( * ) Notice: Subject to any disclaimer, the term of this patent is extended or adjusted under 35 U.S.C. 154(b) by 531 days.

(21) Appl. No.: 16/746,448

(22) Filed: Jan. 17, 2020

(65) Prior Publication Data
US 2020/0289140 A1    Sep. 17, 2020

Related U.S. Application Data

(60) Division of application No. 15/195,898, filed on Jun. 28, 2016, now Pat. No. 10,537,348, which is a (Continued)

(51) Int. Cl.
*A61B 17/10* (2006.01)
*A61B 34/00* (2016.01)
(Continued)

(52) U.S. Cl.
CPC .............. *A61B 17/10* (2013.01); *A61B 17/08* (2013.01); *A61B 17/122* (2013.01);
(Continued)

(58) Field of Classification Search
CPC .. A61B 2017/00876; A61B 2017/2931; A61B 17/29; A61B 34/73; A61B 17/0218;
(Continued)

(56) References Cited

U.S. PATENT DOCUMENTS 2,678,228 A   5/1954   Gerhardt
2,863,444 A   12/1958   Winsten
(Continued)

FOREIGN PATENT DOCUMENTS

CA    2 748 471 A1    7/2010
CA    2733465 A1    9/2011
(Continued)

OTHER PUBLICATIONS

Aesculap, "Endoscopic Vascular surgery in the pelvic region," B/Braun, Aesculap AG & Co.KG, Catalog, 48 pages, 2006, Copy Unavailable, document can be accessed at https://docplayer.net/22042174-Aesculap-endoscopic-technology-endoscopic-vascular-surgery-in-the-pelvic-region.html.
(Continued)

*Primary Examiner* — Katherine M Shi
(74) *Attorney, Agent, or Firm* — Cooley LLP

(57) ABSTRACT

Described here are systems, devices, and methods for providing remote manipulation or traction to tissue using one or more graspers, delivery devices, and magnetic control assemblies. The graspers may be configured for insertion into the patient during a minimally-invasive procedure, such as a laparoscopic operation. The graspers may be configured to releasably connect to tissue. In some embodiments, the grasper may comprise a clip, a clamp, a suction device, a coil, or the like, and may be configured to connect to any suitable tissue. Delivery devices may be configured to releasably engage a grasper to deliver the grasper, remove it from the patient, or reposition it. The delivery devices may additionally be configured to actuate the grasper to attach it to tissue and/or detach it from tissue. The magnetic control elements may be configured to be positioned externally of the body to move, reposition, and/or hold the grasper.

15 Claims, 29 Drawing Sheets

Related U.S. Application Data continuation of application No. PCT/US2015/012319, filed on Jan. 21, 2015.

(60) Provisional application No. 61/929,918, filed on Jan. 21, 2014.

(51) Int. Cl.
| | |
|---|---|
| *A61B 17/128* | (2006.01) |
| *A61B 17/122* | (2006.01) |
| *A61B 17/08* | (2006.01) |
| *A61B 17/29* | (2006.01) |
| *A61B 17/00* | (2006.01) |
| *A61B 17/30* | (2006.01) |

(52) U.S. Cl.
CPC .......... *A61B 17/1285* (2013.01); *A61B 17/29* (2013.01); *A61B 34/73* (2016.02); *A61B 2017/00336* (2013.01); *A61B 2017/00876* (2013.01); *A61B 2017/2931* (2013.01); *A61B 2017/2941* (2013.01); *A61B 2017/2947* (2013.01); *A61B 2017/305* (2013.01); *A61B 2017/306* (2013.01); *A61B 2017/308* (2013.01)

(58) Field of Classification Search
CPC ........ A61B 17/122; A61B 2017/00473; A61B 2017/00477; A61B 17/08; A61B 17/1285; A61B 17/00234; A61B 17/1227
See application file for complete search history.

(56) References Cited

U.S. PATENT DOCUMENTS

| | | | |
|---|---|---|---|
| 3,146,381 A | 8/1964 | Louis | |
| 3,674,014 A | 7/1972 | Tillander | |
| 3,789,285 A | 1/1974 | Nishizawa | |
| 3,794,091 A | 2/1974 | Ersek et al. | |
| 4,364,377 A | 12/1982 | Smith | |
| 4,380,999 A | 4/1983 | Healy | |
| 4,706,668 A | 11/1987 | Backer | |
| 4,756,312 A | 7/1988 | Epley | |
| 4,901,405 A | 2/1990 | Grover et al. | |
| 4,915,435 A | 4/1990 | Levine | |
| 4,968,136 A | 11/1990 | Lim et al. | |
| 4,971,067 A | 11/1990 | Bolduc et al. | |
| 4,976,723 A | 12/1990 | Schad | |
| 4,997,436 A | 3/1991 | Oberlander | |
| 5,002,557 A | 3/1991 | Hasson | |
| 5,154,189 A | 10/1992 | Oberlander | |
| 5,156,608 A | 10/1992 | Troidl et al. | |
| 5,156,609 A | 10/1992 | Nakao et al. | |
| 5,282,806 A | 2/1994 | Haber et al. | |
| 5,300,081 A | 4/1994 | Young et al. | |
| 5,304,183 A | 4/1994 | Gourlay et al. | |
| 5,304,185 A | 4/1994 | Taylor | |
| 5,307,805 A | 5/1994 | Byrne | |
| 5,340,360 A | 8/1994 | Stefanchik | |
| 5,397,325 A | 3/1995 | Della Badia | |
| 5,411,535 A | 5/1995 | Fujii et al. | |
| 5,415,160 A | 5/1995 | Ortiz et al. | |
| 5,417,701 A | 5/1995 | Holmes | |
| 5,449,361 A | 9/1995 | Preissman | |
| 5,449,365 A | 9/1995 | Green et al. | |
| 5,450,842 A | 9/1995 | Tovey et al. | |
| 5,458,603 A | 10/1995 | Futch, Sr. | |
| 5,458,693 A | 10/1995 | Codorniu | |
| 5,465,711 A | 11/1995 | Moll et al. | |
| 5,496,317 A | 3/1996 | Goble et al. | |
| 5,499,986 A | 3/1996 | Dimarco | |
| 5,529,568 A | 6/1996 | Rayman | |
| 5,538,098 A | 7/1996 | Sparhawk | |
| 5,569,274 A * | 10/1996 | Rapacki ............. A61B 18/1442 606/151 |
| 5,593,379 A | 1/1997 | Rayman | |
| 5,595,562 A | 1/1997 | Grier | |
| 5,654,864 A | 8/1997 | Ritter et al. | |
| 5,665,100 A | 9/1997 | Yoon | |
| 5,681,260 A | 10/1997 | Ueda et al. | |
| 5,728,121 A | 3/1998 | Bimbo et al. | |
| 5,733,292 A | 3/1998 | Gustilo et al. | |
| 5,749,881 A | 5/1998 | Sackier et al. | |
| 5,766,189 A | 6/1998 | Matsuno | |
| 5,782,748 A | 7/1998 | Palmer et al. | |
| 5,797,911 A | 8/1998 | Sherman et al. | |
| 5,797,939 A | 8/1998 | Yoon | |
| 5,824,041 A * | 10/1998 | Lenker ............. A61F 2/91 606/195 |
| 5,848,969 A | 12/1998 | Panescu et al. | |
| 5,849,015 A | 12/1998 | Haywood et al. | |
| 5,888,196 A | 3/1999 | Bonutti | |
| 5,893,873 A | 4/1999 | Rader et al. | |
| 5,933,926 A | 8/1999 | Reiter | |
| 6,015,414 A | 1/2000 | Werp et al. | |
| 6,017,358 A | 1/2000 | Yoon et al. | |
| 6,096,038 A | 8/2000 | Michelson | |
| 6,099,537 A | 8/2000 | Sugai et al. | |
| 6,099,550 A | 8/2000 | Yoon | |
| 6,123,657 A | 9/2000 | Ishikawa et al. | |
| 6,126,647 A | 10/2000 | Posey et al. | |
| 6,127,757 A | 10/2000 | Banks | |
| 6,165,180 A | 12/2000 | Cigaina et al. | |
| 6,173,715 B1 | 1/2001 | Sinanan et al. | |
| 6,212,419 B1 | 4/2001 | Blume et al. | |
| 6,216,028 B1 | 4/2001 | Haynor et al. | |
| 6,241,671 B1 | 6/2001 | Ritter et al. | |
| 6,311,082 B1 | 10/2001 | Creighton, IV et al. | |
| 6,315,709 B1 | 11/2001 | Garibaldi et al. | |
| 6,330,467 B1 | 12/2001 | Creighton, IV et al. | |
| 6,340,365 B2 | 1/2002 | Dittrich et al. | |
| 6,358,196 B1 | 3/2002 | Rayman | |
| 6,371,973 B1 | 4/2002 | Tepper | |
| 6,398,791 B1 | 6/2002 | Que et al. | |
| 6,399,146 B1 | 6/2002 | Harris et al. | |
| 6,401,723 B1 | 6/2002 | Garibaldi et al. | |
| 6,440,133 B1 | 8/2002 | Beale et al. | |
| 6,458,146 B1 | 10/2002 | Kramer | |
| 6,459,924 B1 | 10/2002 | Creighton, IV et al. | |
| 6,464,710 B1 | 10/2002 | Foster | |
| 6,488,615 B1 | 12/2002 | Mitchiner et al. | |
| 6,523,919 B1 | 2/2003 | Israelsen et al. | |
| 6,537,196 B1 | 3/2003 | Creighton, IV et al. | |
| 6,551,304 B1 | 4/2003 | Whalen et al. | |
| 6,594,517 B1 | 7/2003 | Nevo | |
| 6,630,879 B1 | 10/2003 | Creighton, IV et al. | |
| 6,632,229 B1 | 10/2003 | Yamanouchi | |
| 6,641,595 B1 | 11/2003 | Moran et al. | |
| 6,656,199 B1 | 12/2003 | Lafontaine | |
| 6,677,752 B1 | 1/2004 | Creighton, IV et al. | |
| 6,689,119 B1 | 2/2004 | Di Caprio et al. | |
| 6,702,804 B1 | 3/2004 | Ritter et al. | |
| 6,705,989 B2 | 3/2004 | Cuschieri et al. | |
| 6,719,765 B2 | 4/2004 | Bonutti | |
| 6,761,681 B2 | 7/2004 | Schmid et al. | |
| 6,786,219 B2 | 9/2004 | Garibaldi et al. | |
| 6,817,364 B2 | 11/2004 | Garibaldi et al. | |
| 6,824,511 B1 | 11/2004 | Bell et al. | |
| 6,916,314 B2 | 7/2005 | Schneider et al. | |
| 7,017,584 B2 | 3/2006 | Garibaldi et al. | |
| 7,094,245 B2 | 8/2006 | Adams et al. | |
| 7,169,104 B2 | 1/2007 | Ueda et al. | |
| 7,182,089 B2 | 2/2007 | Ries | |
| 7,182,775 B2 | 2/2007 | De Guillebon et al. | |
| 7,189,198 B2 | 3/2007 | Harburn et al. | |
| 7,264,584 B2 | 9/2007 | Ritter et al. | |
| 7,300,400 B2 | 11/2007 | Brown | |
| 7,311,107 B2 | 12/2007 | Harel et al. | |
| 7,313,429 B2 | 12/2007 | Creighton, IV et al. | |
| 7,314,063 B2 | 1/2008 | Egli | |
| 7,341,063 B2 | 3/2008 | Garbibaldi et al. | |
| 7,344,553 B2 | 3/2008 | Opolski et al. | |
| 7,390,298 B2 | 6/2008 | Chu | |
| 7,416,335 B2 | 8/2008 | Munger | |
| 7,429,259 B2 | 9/2008 | Cadeddu et al. | |

(56) References Cited

U.S. PATENT DOCUMENTS

| | | |
|---|---|---|
| 7,431,726 B2 | 10/2008 | Spence et al. |
| 7,566,038 B2 | 7/2009 | Scott et al. |
| 7,618,435 B2 | 11/2009 | Opolski |
| 7,686,827 B2 | 3/2010 | Hushka |
| 7,691,103 B2 | 4/2010 | Fernandez et al. |
| 7,691,731 B2 | 4/2010 | Bet et al. |
| 7,708,756 B2 | 5/2010 | Nobis et al. |
| 7,736,356 B2 | 6/2010 | Cooper et al. |
| 7,766,810 B2 | 8/2010 | Ohdaira |
| 7,769,427 B2 | 8/2010 | Shachar |
| 7,772,950 B2 | 8/2010 | Tunay |
| 7,774,046 B2 | 8/2010 | Werp et al. |
| 7,780,054 B2 | 8/2010 | Wales |
| 7,799,050 B2 | 9/2010 | Hensley et al. |
| 7,837,612 B2 | 11/2010 | Gill et al. |
| 7,850,591 B2 | 12/2010 | Spector |
| 7,942,885 B2 | 5/2011 | Sixto, Jr. et al. |
| 7,963,903 B2 | 6/2011 | Ghiron et al. |
| 7,966,059 B2 | 6/2011 | Creighton, IV et al. |
| 7,967,830 B2 | 6/2011 | Ayala et al. |
| 8,038,612 B2 | 10/2011 | Paz |
| 8,043,290 B2 | 10/2011 | Harrison et al. |
| 8,057,472 B2 | 11/2011 | Walker et al. |
| 8,060,184 B2 | 11/2011 | Hastings et al. |
| 8,066,715 B2 | 11/2011 | Ducharme |
| 8,074,657 B2 | 12/2011 | Scott et al. |
| 8,082,035 B2 | 12/2011 | Glukhovsky |
| 8,133,254 B2 | 3/2012 | Dumbauld et al. |
| 8,136,888 B2 | 3/2012 | Suzuki et al. |
| 8,137,268 B2 | 3/2012 | Van Lue |
| 8,157,149 B2 | 4/2012 | Olson et al. |
| 8,187,286 B2 | 5/2012 | Jugenheimer et al. |
| 8,197,494 B2 | 6/2012 | Jaggi et al. |
| 8,226,690 B2 | 7/2012 | Altarac et al. |
| 8,235,272 B2 | 8/2012 | Nicholas et al. |
| 8,241,322 B2 | 8/2012 | Whitman et al. |
| 8,246,529 B2 | 8/2012 | Riehl et al. |
| 8,252,021 B2 | 8/2012 | Boulnois et al. |
| 8,267,854 B2 | 9/2012 | Asada et al. |
| 8,301,226 B2 | 10/2012 | Csavoy et al. |
| 8,303,495 B2 | 11/2012 | Ducharme |
| 8,313,497 B2 | 11/2012 | Walberg et al. |
| 8,316,861 B2 | 11/2012 | Brewer et al. |
| 8,316,862 B2 | 11/2012 | Shapiro et al. |
| 8,333,695 B2 | 12/2012 | Cuschieri |
| 8,343,171 B2 | 1/2013 | Farritor et al. |
| 8,360,972 B2 | 1/2013 | Paz |
| 8,364,277 B2 | 1/2013 | Glukhovsky |
| 8,377,044 B2 | 2/2013 | Coe et al. |
| 8,382,754 B2 | 2/2013 | Odom et al. |
| 8,403,916 B2 | 3/2013 | Prescott |
| 8,409,076 B2 | 4/2013 | Pang et al. |
| 8,480,668 B2 | 7/2013 | Fernandez et al. |
| 8,491,626 B2 | 7/2013 | Roy et al. |
| 8,517,931 B2 | 8/2013 | Minnelli et al. |
| 8,518,057 B2 | 8/2013 | Walberg et al. |
| 8,556,919 B2 | 10/2013 | Aguirre et al. |
| 8,579,787 B2 | 11/2013 | Shapiro et al. |
| 8,585,685 B2 | 11/2013 | Hagg |
| 8,602,981 B2 | 12/2013 | Deutch |
| 8,608,773 B2 | 12/2013 | Tierney et al. |
| 8,623,011 B2 | 1/2014 | Spivey |
| 8,628,529 B2 | 1/2014 | Aldridge et al. |
| 8,636,762 B2 | 1/2014 | Whitman et al. |
| 8,637,818 B2 | 1/2014 | Balakin |
| 8,685,043 B2 | 4/2014 | Jugenheimer et al. |
| 8,758,394 B2 | 6/2014 | Zimmerling et al. |
| 8,764,769 B1 | 7/2014 | Rodriguez-Navarro et al. |
| 8,790,245 B2 | 7/2014 | Rodriguez Fernandez et al. |
| 8,820,602 B2 | 9/2014 | Walberg et al. |
| 8,827,891 B2 | 9/2014 | Roberts |
| 8,828,024 B2 | 9/2014 | Farritor et al. |
| 8,894,574 B2 | 11/2014 | Ellman |
| 8,926,656 B2 | 1/2015 | Palermo et al. |
| 8,944,997 B2 | 2/2015 | Fernandez et al. |
| 8,968,332 B2 | 3/2015 | Farritor et al. |
| 8,968,356 B2 | 3/2015 | Mueller |
| 9,011,468 B2 | 4/2015 | Ketai et al. |
| 9,033,957 B2 | 5/2015 | Cadeddu et al. |
| 9,044,256 B2 | 6/2015 | Cadeddu et al. |
| 9,339,285 B2 | 5/2016 | Rodriguez-Navarro et al. |
| 9,386,973 B2 | 7/2016 | Deutch |
| 9,561,031 B2 | 2/2017 | Heinrich et al. |
| 9,627,120 B2 | 4/2017 | Scott et al. |
| 9,844,391 B2 | 12/2017 | Rodriguez Fernandez et al. |
| 9,962,148 B2 | 5/2018 | Deutch |
| 9,974,546 B2 | 5/2018 | Rodriguez Fernandez et al. |
| 10,010,370 B2 | 7/2018 | Rodriguez-Navarro et al. |
| 10,130,381 B2 | 11/2018 | Rodriguez-Navarro et al. |
| 10,143,459 B2 | 12/2018 | Heftman |
| 10,335,134 B2 | 7/2019 | Deutch |
| 10,537,348 B2 | 1/2020 | Rodriguez-Navarro et al. |
| 10,905,511 B2 | 2/2021 | Rodriguez-Navarro et al. |
| 11,020,137 B2 | 6/2021 | Rodriguez-Navarro |
| 11,357,525 B2 | 6/2022 | Rodriguez-Navarro et al. |
| 11,413,025 B2 | 8/2022 | Deutch |
| 11,413,026 B2 | 8/2022 | Deutch |
| 11,583,354 B2 | 2/2023 | Rodriguez-Navarro et al. |
| 2001/0038683 A1 | 11/2001 | Ritter et al. |
| 2002/0100486 A1 | 8/2002 | Creighton, IV et al. |
| 2002/0107533 A1 | 8/2002 | Solingen |
| 2002/0116043 A1 | 8/2002 | Garibaldi et al. |
| 2002/0173805 A1 | 11/2002 | Matsuno et al. |
| 2003/0114731 A1 | 6/2003 | Cadeddu et al. |
| 2003/0125752 A1 | 7/2003 | Werp et al. |
| 2003/0181945 A1 | 9/2003 | Opolski et al. |
| 2003/0208185 A1 | 11/2003 | Sheffer et al. |
| 2004/0044295 A1 | 3/2004 | Reinert et al. |
| 2004/0050395 A1 | 3/2004 | Ueda et al. |
| 2004/0064153 A1 | 4/2004 | Creighton, IV et al. |
| 2004/0068173 A1 | 4/2004 | Viswanathan |
| 2004/0158972 A1 | 8/2004 | Creighton, IV et al. |
| 2004/0172057 A1 | 9/2004 | Guillebon et al. |
| 2004/0186347 A1 | 9/2004 | Shose et al. |
| 2004/0199074 A1 | 10/2004 | Ritter et al. |
| 2004/0230100 A1 | 11/2004 | Shluzas |
| 2004/0249262 A1 | 12/2004 | Werp et al. |
| 2005/0080440 A1 | 4/2005 | Durgin et al. |
| 2005/0085696 A1 | 4/2005 | Uchiyama et al. |
| 2005/0113628 A1 | 5/2005 | Creighton, IV et al. |
| 2005/0131390 A1 | 6/2005 | Heinrich et al. |
| 2005/0165449 A1 | 7/2005 | Cadeddu et al. |
| 2005/0220583 A1 | 10/2005 | Lutz |
| 2005/0250988 A1 | 11/2005 | Ewers et al. |
| 2005/0251183 A1* | 11/2005 | Buckman ............... A61B 17/08 606/157 |
| 2005/0277975 A1 | 12/2005 | Saadat et al. |
| 2006/0015178 A1 | 1/2006 | Moaddeb et al. |
| 2006/0074448 A1 | 4/2006 | Harrison et al. |
| 2006/0079897 A1 | 4/2006 | Harrison et al. |
| 2006/0089633 A1 | 4/2006 | Bleich et al. |
| 2006/0116714 A1 | 6/2006 | Sepetka et al. |
| 2006/0149135 A1 | 7/2006 | Paz |
| 2006/0152309 A1 | 7/2006 | Mintchev et al. |
| 2006/0228421 A1 | 10/2006 | Seeney et al. |
| 2006/0241691 A1 | 10/2006 | Wilk |
| 2006/0247522 A1 | 11/2006 | Mcgee |
| 2006/0276738 A1 | 12/2006 | Becker |
| 2006/0293566 A1 | 12/2006 | Brown |
| 2007/0004958 A1 | 1/2007 | Ohdaira |
| 2007/0016010 A1 | 1/2007 | Creighton, IV et al. |
| 2007/0027458 A1 | 2/2007 | Sixto, Jr. et al. |
| 2007/0043359 A1 | 2/2007 | Altarac et al. |
| 2007/0073102 A1 | 3/2007 | Matsuno et al. |
| 2007/0135678 A1 | 6/2007 | Suzuki |
| 2007/0135685 A1 | 6/2007 | Cuschieri |
| 2007/0135802 A1 | 6/2007 | Suzuki |
| 2007/0135803 A1 | 6/2007 | Belson |
| 2007/0156028 A1 | 7/2007 | Van Lue et al. |
| 2007/0191670 A1 | 8/2007 | Spector |
| 2007/0221233 A1 | 9/2007 | Kawano et al. |
| 2007/0255273 A1 | 11/2007 | Fernandez et al. |
| 2007/0270629 A1 | 11/2007 | Charles |
| 2007/0282311 A1 | 12/2007 | Scott et al. |

(56) References Cited

U.S. PATENT DOCUMENTS

| | | |
|---|---|---|
| 2008/0081883 A1 | 4/2008 | King, II et al. |
| 2008/0097496 A1 | 4/2008 | Chang et al. |
| 2008/0108860 A1 | 5/2008 | Bell et al. |
| 2008/0134474 A1 | 6/2008 | Uryasov |
| 2008/0171907 A1 | 7/2008 | Long et al. |
| 2008/0243106 A1 | 10/2008 | Coe et al. |
| 2008/0249534 A1 | 10/2008 | Gruber et al. |
| 2008/0269779 A1 | 10/2008 | Cadeddu et al. |
| 2008/0300458 A1 | 12/2008 | Kim et al. |
| 2009/0004324 A1 | 1/2009 | Viel et al. |
| 2009/0005636 A1 | 1/2009 | Pang et al. |
| 2009/0043246 A1 | 2/2009 | Dominguez |
| 2009/0054909 A1 | 2/2009 | Farritor et al. |
| 2009/0062772 A1 | 3/2009 | Wakeford et al. |
| 2009/0076536 A1 | 3/2009 | Rentschler et al. |
| 2009/0137984 A1 | 5/2009 | Minnelli |
| 2009/0187074 A1 | 7/2009 | Saadat et al. |
| 2009/0192344 A1 | 7/2009 | Bakos et al. |
| 2009/0222029 A1* | 9/2009 | Gordin .................. A61B 17/29 606/151 |
| 2009/0026771 A1 | 10/2009 | Baskett |
| 2009/0267717 A1 | 10/2009 | Baskett |
| 2009/0318762 A1 | 12/2009 | Segawa et al. |
| 2010/0010306 A1 | 1/2010 | Kawano et al. |
| 2010/0030026 A1 | 2/2010 | Uchiyama et al. |
| 2010/0036394 A1 | 2/2010 | Mintz et al. |
| 2010/0036399 A1 | 2/2010 | Viola |
| 2010/0081876 A1 | 4/2010 | Linenkugel et al. |
| 2010/0105984 A1 | 4/2010 | Brewer et al. |
| 2010/0113872 A1 | 5/2010 | Asada et al. |
| 2010/0114126 A1 | 5/2010 | Neff |
| 2010/0137845 A1 | 6/2010 | Ramstein et al. |
| 2010/0145147 A1 | 6/2010 | Pinsky et al. |
| 2010/0152539 A1 | 6/2010 | Ghabrial et al. |
| 2010/0160739 A1 | 6/2010 | Van Lue |
| 2010/0168523 A1 | 7/2010 | Ducharme |
| 2010/0174234 A1 | 7/2010 | Werp et al. |
| 2010/0193566 A1 | 8/2010 | Scheib et al. |
| 2010/0204727 A1 | 8/2010 | Dominguez |
| 2010/0217245 A1 | 8/2010 | Prescott |
| 2010/0237206 A1 | 9/2010 | Barker |
| 2010/0256636 A1 | 10/2010 | Fernandez et al. |
| 2010/0268254 A1 | 10/2010 | Golden et al. |
| 2010/0298645 A1 | 11/2010 | Deutch |
| 2011/0040152 A1 | 2/2011 | Kim et al. |
| 2011/0054306 A1 | 3/2011 | Del Nido et al. |
| 2011/0087223 A1 | 4/2011 | Spivey |
| 2011/0087224 A1 | 4/2011 | Cadeddu et al. |
| 2011/0087249 A1 | 4/2011 | Rodrigues et al. |
| 2011/0105848 A1 | 5/2011 | Sadovsky et al. |
| 2011/0121050 A1 | 5/2011 | Nicholas et al. |
| 2011/0130787 A1 | 6/2011 | Cinquin et al. |
| 2011/0184440 A1 | 7/2011 | Saldinger |
| 2011/0230726 A1 | 9/2011 | Viola |
| 2011/0230869 A1 | 9/2011 | Altamirano |
| 2011/0276941 A1 | 11/2011 | Oi |
| 2011/0283822 A1 | 11/2011 | Cadeddu et al. |
| 2011/0284014 A1 | 11/2011 | Cadeddu et al. |
| 2011/0285488 A1 | 11/2011 | Scott et al. |
| 2011/0295067 A1 | 12/2011 | Rodriguez Fernandez et al. |
| 2011/0306840 A1 | 12/2011 | Allen et al. |
| 2011/0313415 A1 | 12/2011 | Fernandez et al. |
| 2012/0016362 A1 | 1/2012 | Heinrich et al. |
| 2012/0035416 A1 | 2/2012 | Fernandez et al. |
| 2012/0053402 A1 | 3/2012 | Conlon et al. |
| 2012/0053406 A1 | 3/2012 | Conlon et al. |
| 2012/0065627 A1 | 3/2012 | Ghabrial et al. |
| 2012/0078292 A1 | 3/2012 | Banju |
| 2012/0008535 A1 | 4/2012 | Cadeddu et al. |
| 2012/0085358 A1 | 4/2012 | Cadeddu et al. |
| 2012/0101488 A1 | 4/2012 | Aldridge et al. |
| 2012/0116148 A1 | 5/2012 | Weinberg et al. |
| 2012/0227748 A1 | 9/2012 | Sanders |
| 2012/0238796 A1 | 9/2012 | Conlon |
| 2012/0330089 A1 | 12/2012 | Ritter et al. |
| 2013/0030462 A1 | 1/2013 | Keating et al. |
| 2013/0066304 A1 | 3/2013 | Belson et al. |
| 2013/0085341 A1 | 4/2013 | Nobis et al. |
| 2013/0090666 A1 | 4/2013 | Hess et al. |
| 2013/0109267 A1 | 5/2013 | Schweikardt et al. |
| 2013/0110128 A1 | 5/2013 | Schostek et al. |
| 2013/0123828 A1 | 5/2013 | Culmer et al. |
| 2013/0158348 A1 | 6/2013 | Nobis et al. |
| 2013/0158523 A1 | 6/2013 | Bergs et al. |
| 2013/0158659 A1 | 6/2013 | Bergs et al. |
| 2013/0158660 A1 | 6/2013 | Bergs et al. |
| 2013/0172672 A1 | 7/2013 | Iddan et al. |
| 2013/0172906 A1 | 7/2013 | Olson et al. |
| 2013/0226226 A1 | 8/2013 | Garrison et al. |
| 2013/0245356 A1 | 9/2013 | Fernandez et al. |
| 2013/0253256 A1 | 9/2013 | Griffith et al. |
| 2013/0253275 A1 | 9/2013 | Ransden et al. |
| 2013/0253550 A1 | 9/2013 | Beisel et al. |
| 2013/0267788 A1 | 10/2013 | Duan et al. |
| 2013/0289579 A1 | 10/2013 | Yeung et al. |
| 2013/0289768 A1 | 10/2013 | Yeung et al. |
| 2013/0303851 A1 | 11/2013 | Griffith et al. |
| 2014/0066695 A1 | 3/2014 | Deutch |
| 2014/0084761 A1 | 3/2014 | Scott et al. |
| 2014/0135616 A1 | 5/2014 | Stein et al. |
| 2014/0176797 A1 | 6/2014 | Silva et al. |
| 2014/0187857 A1 | 7/2014 | Wilson et al. |
| 2014/0243586 A1* | 8/2014 | Rohaninejad .......... A61B 34/73 600/37 |
| 2014/0243597 A1 | 8/2014 | Weisenburgh, II et al. |
| 2014/0257370 A1 | 9/2014 | Taylor et al. |
| 2014/0276335 A1 | 9/2014 | Pate |
| 2014/0277104 A1 | 9/2014 | Rodriguez-Navarro et al. |
| 2014/0350574 A1 | 11/2014 | Farritor et al. |
| 2014/0358229 A1 | 12/2014 | Bergs et al. |
| 2015/0012010 A1 | 1/2015 | Adler et al. |
| 2015/0141750 A1 | 5/2015 | Iddan et al. |
| 2016/0038135 A1 | 2/2016 | Deutch |
| 2016/0120613 A1 | 5/2016 | Cadeddu et al. |
| 2018/0092703 A1 | 4/2018 | Rodriguez-Navarro et al. |
| 2018/0153633 A1 | 6/2018 | Rodriguez-Navarro et al. |
| 2018/0271550 A1 | 9/2018 | Rodriguez-Navarro |
| 2018/0271603 A1 | 9/2018 | Nir et al. |
| 2018/0296289 A1 | 10/2018 | Rodriguez-Navarro et al. |
| 2018/0325604 A1 | 11/2018 | Atarot et al. |
| 2019/0133631 A1 | 5/2019 | Rodriguez-Navarro et al. |
| 2019/0269394 A1 | 9/2019 | Deutch |
| 2019/0350575 A1 | 11/2019 | Deutch |
| 2020/0289140 A1 | 9/2020 | Rodriguez-Navarro et al. |
| 2021/0290330 A1 | 9/2021 | Rodriguez-Navarro et al. |
| 2022/0015789 A1 | 1/2022 | Rodriguez-Navarro |
| 2023/0021246 A1 | 1/2023 | Rodriguez-Navarro et al. |

FOREIGN PATENT DOCUMENTS

| | | |
|---|---|---|
| CN | 2244381 Y | 1/1997 |
| CN | 101090672 A | 12/2007 |
| CN | 201079412 Y | 7/2008 |
| CN | 201091596 Y | 7/2008 |
| CN | 101534725 A | 9/2009 |
| CN | 102068288 A | 5/2011 |
| CN | 102355865 A | 2/2012 |
| CN | 203953720 U | 11/2014 |
| DE | 42 12 430 A1 | 10/1993 |
| DE | 19534618 A1 | 3/1997 |
| DE | 10 2005 006 705 A1 | 8/2006 |
| DE | 10-2010-010417 A1 | 9/2011 |
| EP | 1 797 823 A1 | 6/2007 |
| EP | 1 972 284 A2 | 9/2008 |
| EP | 2 012 697 A2 | 1/2009 |
| EP | 2 355 699 A2 | 8/2011 |
| EP | 2 366 357 A1 | 9/2011 |
| EP | 2 381 873 A2 | 11/2011 |
| EP | 2 391 277 | 12/2011 |
| EP | 1 942 810 B1 | 8/2012 |
| EP | 2 571 443 A2 | 3/2013 |
| EP | 2 595 548 | 5/2013 |
| EP | 2 842 511 A1 | 3/2015 |
| JP | 09-192137 A | 7/1997 |

(56) References Cited

FOREIGN PATENT DOCUMENTS

| JP | 2004-357816 A | 12/2004 |
|---|---|---|
| JP | 2005-021576 A | 1/2005 |
| JP | 4320214 B2 | 8/2009 |
| JP | 2009-538699 A | 11/2009 |
| WO | WO-00/51500 A1 | 9/2000 |
| WO | WO-2005/004734 A1 | 1/2005 |
| WO | WO-2005/032370 A1 | 4/2005 |
| WO | WO-2006/071120 A1 | 7/2006 |
| WO | WO-2007/067231 A1 | 6/2007 |
| WO | WO-2007/130382 A2 | 11/2007 |
| WO | WO-2007/130382 A3 | 11/2007 |
| WO | WO-2007/142977 A2 | 12/2007 |
| WO | WO-2007/142977 A3 | 12/2007 |
| WO | WO-2007/143162 A2 | 12/2007 |
| WO | WO-2007/143162 A3 | 12/2007 |
| WO | WO-2007/143170 A2 | 12/2007 |
| WO | WO-2007/143170 A3 | 12/2007 |
| WO | WO-2008/039237 A1 | 4/2008 |
| WO | WO-2008/085919 A2 | 7/2008 |
| WO | WO-2008/085919 A3 | 7/2008 |
| WO | WO-2008/131128 A1 | 10/2008 |
| WO | WO-2009/008865 A1 | 1/2009 |
| WO | WO-2009/019288 A2 | 2/2009 |
| WO | WO-2009/019288 A3 | 2/2009 |
| WO | WO-2009/070743 A1 | 6/2009 |
| WO | WO-2010/056716 A2 | 5/2010 |
| WO | WO-2010/056716 A3 | 5/2010 |
| WO | WO-2010/077561 A1 | 7/2010 |
| WO | WO-2010/083480 A2 | 7/2010 |
| WO | WO-2010/083480 A3 | 7/2010 |
| WO | WO-2010/089635 A1 | 8/2010 |
| WO | WO-2011/044468 A2 | 4/2011 |
| WO | WO-2011/044468 A3 | 4/2011 |
| WO | WO-2011/044471 A2 | 4/2011 |
| WO | WO-2011/044471 A3 | 4/2011 |
| WO | WO-2011/091483 A1 | 8/2011 |
| WO | WO-2011/146691 A2 | 11/2011 |
| WO | WO-2011/146691 A3 | 11/2011 |
| WO | WO2011/146698 A2 | 11/2011 |
| WO | WO2011/146698 A3 | 11/2011 |
| WO | WO-2011/146709 A2 | 11/2011 |
| WO | WO-2011/146709 A3 | 11/2011 |
| WO | WO-2012/010910 A1 | 1/2012 |
| WO | WO-2012/031114 A2 | 3/2012 |
| WO | WO-2012/031114 A3 | 3/2012 |
| WO | WO-2012/033925 A1 | 3/2012 |
| WO | WO-2012/048102 A2 | 4/2012 |
| WO | WO-2012/048102 A3 | 4/2012 |
| WO | WO-2013/096470 A1 | 6/2013 |
| WO | WO-2014/133751 A1 | 9/2014 |
| WO | WO-2014/159023 A1 | 10/2014 |
| WO | WO-2014/163872 A1 | 10/2014 |
| WO | WO-2015/112645 A1 | 7/2015 |
| WO | WO-2015/142953 A1 | 9/2015 |
| WO | WO-2016/168380 A1 | 10/2016 |

OTHER PUBLICATIONS

Extended European Search Report dated Jul. 22, 2019, for EP Application No. 19 151 941.2, filed on Feb. 25, 2014, 6 pages.
Extended European Search Report dated May 31, 2013, for EP Application No. 08 853 840.0, filed on Nov. 26, 2008, 11 pages.
Extended European Search Report dated Jan. 4, 2022, for EP Application No. 21 189 505.7, filed on Apr. 13, 2016, 10 pages.
Extended European Search Report dated Jan. 18, 2022, for EP Application No. 21 187 437.5, filed on Apr. 13, 2016, 6 pages.
Extended European Search Report dated Feb. 17, 2022, for EP Application No. 21 189 492.8, filed on Feb. 25, 2014, 6 pages.
Final Office Action dated Nov. 25, 2020, for U.S. Appl. No. 15/728,297, filed Oct. 9, 2017, 11 pages.
Final Office Action dated Sep. 3, 2021, for U.S. Appl. No. 16/149,576, filed Oct. 2, 2018, 14 pages.
Final Office Action dated Oct. 26, 2021, for U.S. Appl. No. 16/419,363, filed May 22, 2019, 7 pages.
Final Office Action dated Oct. 28, 2021, for U.S. Appl. No. 16/528,878, filed Aug. 1, 2019, 8 pages.
Final Office Action dated Feb. 7, 2022, for U.S. Appl. No. 16/008,976, filed Jun. 14, 2018, 20 pages.
Final Office Action dated May 2, 2022, for U.S. Appl. No. 15/728,297, filed Oct. 9, 2017, 13 pages.
International Search Report dated Apr. 9, 2009, for PCT Application No. PCT/US2008/084991, filed on Nov. 26, 2008, 3 pages.
Milki et al. (1998). Vaginal ultrasound probe coverage leakage implications for patient care, fertility and sterility, American Society for Reproductive Medicine, vol. 69, No. 3.
Non-Final Office Action dated Dec. 22, 2020, for U.S. Appl. No. 16/149,576, filed Oct. 2, 2018, 10 pages.
Non-Final Office Action dated May 12, 2021, for U.S. Appl. No. 16/008,976, filed Jun. 14, 2018, 15 pages.
Non-Final Office Action dated Apr. 29, 2021, for U.S. Appl. No. 16/419,363, filed May 22, 2019, 9 pages.
Non-Final Office Action dated Apr. 15, 2021, for U.S. Appl. No. 16/528,878, filed Aug. 1, 2019, 6 pages.
Non-Final Office Action dated Sep. 15, 2021, for U.S. Appl. No. 15/728,297, filed Oct. 9, 2017, 11 pages.
Non-Final Office Action dated Aug. 5, 2022, for U.S. Appl. No. 16/008,976, filed Jun. 14, 2018, 18 pages.
Notice of Allowance dated Sep. 29, 2020, for U.S. Appl. No. 15/728,302, filed Oct. 9, 2017, 8 pages.
Notice of Allowance dated Feb. 5, 2021, for U.S. Appl. No. 15/926,578, filed Mar. 20, 2018, 9 pages.
Notice of Allowance dated Feb. 14, 2022, for U.S. Appl. No. 16/149,576, filed Oct. 2, 2018, 9 pages.
Notice of Allowance dated Apr. 7, 2022, for U.S. Appl. No. 16/528,878, filed Aug. 1, 2019, 6 pages.
Notice of Allowance dated Apr. 20, 2022, for U.S. Appl. No. 16/419,363, filed May 2, 2019, 6 pages.
Odwin et al. (1990), Prove covers and disinfectants for transvaginal transducers, JDMS, 6:130-135.
Supplemental Notice of Allowability dated Dec. 18, 2020, for U.S. Appl. No. 15/728,302, filed Oct. 9, 2017, 3 pages.
Written Opinion of the International Searching Authority dated Apr. 9, 2009, for PCT Application No. PCT/US2008/084991, filed on Nov. 26, 2008, 12 pages.
Best, S.L. et al. (2010). "Development of magnetic anchoring and guidance systems for minimally invasive surgery," Indian J. of Urology 26:418-422.
Best, S.L. et al. (2010). "Solo Surgeon LESS Nephrectomy Facilitated by New Generation Magnetically Anchored and Guided (MAGS) Camera," World Congress of Endourology, PS38-14, Chicago IL, Sep. 2010.
Best, S.L. et al. (2010). "MAGS Instrumentation for LESS/NOTES: Lack of Histologic Damage After Prolonged Magnetic Coupling Across the Abdominal Wall," World Congress of Endourology, PS2-4, Chicago IL, Sep. 2010.
Best, S.L. et al. (2008). "Maximizing Coupling Strength of Magnetically Anchored NOTES Instruments: How Thick Can We Go?" Surgical Endoscopy, vol. 22: S241.
Cadeddu, J.A. et al. (2002). "Transabdominal magnetic anchoring system for trocar-less laparoscopic surgery," J. of Urology, vol. 167, No. 4, Supplement, Abstract No. 16, 1 total page.
Cadeddu, J. et al. (2009). "Novel Magnetically Guided Intraabdominal Camera to Facilitate Laparoendoscopic Single Site Surgery: Initial Human Experience," Surgical Endoscopy 23:1894-1899.
Dominguez (2007). "Colecistectomia con un trocar asistida por imanes de neodimio. Reporte de un caso." Asociacion Mexicana de Cirugia Endo. vol. 8. No. 4, pp. 172-176 (with English Abstract).
Dominguez, G. et al. (2009). "Retraction and triangulation with neodymium magnetic forceps for single-port laparoscopic cholecystectomy," Surg. Endosc. 23:1660-1666.
Duchene, D.A. et al. (2004). "Magnetic positioning system for trocarless laparoscopic instruments," J. of Endourology 18:693.
Extended European Search Report dated Jul. 20, 2016, for EP Application No. 14 778 895.4, filed on Feb. 25, 2014, 7 pages.
Extended European Search Report dated Dec. 20, 2016, for EP Application No. 09 839 564.3, filed on Oct. 1, 2009, 11 pages.

(56) References Cited

OTHER PUBLICATIONS

Extended European Search Report dated Sep. 27, 2017, for EP Application No. 15 741 055.6, filed on Jan. 21, 2015, 9 pages.
Extended European Search Report dated Oct. 30, 2018, for EP Application No. 16 780 691.8, filed on Apr. 13, 2016, 6 pages.
Extended European Search Report dated Nov. 26, 2018, for EP Application No. 16 780 688.4, filed on Sep. 26, 2017, 9 pages.
Extended European Search Report dated Aug. 22, 2019, for EP Application No. 17 736 483.3, filed on Jan. 6, 2017, 8 pages.
Fernandez, R. et al. (2012). "Determining a Performance Envelope for Capture of Kidney Stones Functionalized with Superparamagnetic Particles," Journal of Endourology, 26(9):1227-30.
Fernandez, R. et al. (2003). "Development of a Transabdominal Anchoring System for Trocar-Less Laparoscopic Surgery," Advances in Bioengineering—ASME International Mechanical Engineering Congress & Exposition, Washington DC, Nov. 2003, BED vol. 55, pp. 157-158.
Final Office Action dated Sep. 16, 2016, for U.S. Appl. No. 14/704,828, filed May 5, 2015, 10 pages.
Final Office Action dated Jan. 25, 2016, for U.S. Appl. No. 14/337,082, filed Jul. 21, 2014, 9 pages.
Final Office Action dated Dec. 28, 2016, for U.S. Appl. No. 14/200,302, filed Mar. 7, 2014, 15 pages.
Final Office Action dated Sep. 6, 2017, for U.S. Appl. No. 14/200,302, filed Mar. 7, 2014, 9 pages.
Final Office Action dated Mar. 7, 2018, for U.S. Appl. No. 15/098,262, filed Apr. 13, 2016, 10 pages.
Final Office Action dated Feb. 26, 2019, for U.S. Appl. No. 15/195,898, filed Jun. 28, 2016, 9 pages.
International Search Report dated Jul. 30, 2014, for PCT Application No. PCT/US2014/021537, filed on Mar. 7, 2014, 2 pages.
International Search Report for International Application No. PCT/IB2009/054307 dated Feb. 8, 2010, 4 pages.
International Search Report dated May 4, 2015, for PCT Application No. PCT/US2015/012319, filed on Jan. 21, 2015, 2 pages.
International Search Report dated Jul. 18, 2014, for PCT Application No. PCT/US2014/018307, filed on Feb. 25, 2014, 4 pages.
International Search Report dated Jul. 15, 2016, for PCT Application No. PCT/US2016/027385, filed on Apr. 13, 2016, 2 pages.
International Search Report dated Aug. 22, 2016, for PCT Application No. PCT/US2016/027390, filed on Apr. 13, 2016, 4 pages.
International Search Report dated Apr. 3, 2017, for PCT Application No. PCT/US2017/012628, filed on Jan. 6, 2017, 2 pages.
Leong, F. et al. (2016). "Magnetic surgical instruments for robotic abdominal surgery," IEEE Reviews in Biomedical Engineering 9:66-78.
Mashaud, L. et al. (2011). "Tissue Compression Analysis for Magnetically Anchored Cautery Dissector During Single Site Laparoscopic Cholecystectomy," Journal of Gastrointestinal Surgery 15:902-907.
Mashaud, L. et al. (2010). "Tissue Compression Analysis for Magnetically Anchored Cautery Dissector During Single Site Laparoscopic Cholecystectomy," Gastroenterology, 138:5 (Supplement 1):S-882.
Mashaud, L. et al. (2010). "Magnetic Cautery Dissector Suitability for Traditional or Single Site Laparoscopic Cholecystectomy in Human Cadaver Models," 12th World Congress of Endoscopic Surgery, P246, National Harbor, MD, Apr. 2010.
Non-Final Office Action dated May 25, 2016, for U.S. Appl. No. 14/200,302, filed Mar. 7, 2014, 12 pages.
Non-Final Office Action dated May 21, 2013 for U.S. Appl. No. 13/132,185, filed Aug. 17, 2011, 18 pages.
Non-Final Office Action dated Jul. 21, 2016, for U.S. Appl. No. 14/337,082, filed Jul. 21, 2014, 9 pages.
Non-Final Office Action dated Jul. 13, 2015, for U.S. Appl. No. 14/337,082, filed Jul. 21, 2014, 10 pages.
Non-Final Office Action dated Jan. 25, 2016, for U.S. Appl. No. 14/704,828, filed May 5, 2015, 9 pages.
Non-Final Office Action dated Jul. 14, 2015, for U.S. Appl. No. 14/704,828, filed May 5, 2015, 10 pages.
Non-Final Office Action dated Oct. 24, 2013, for U.S. Appl. No. 14/019,370, filed on Sep. 5, 2013, 7 pages.
Non-Final Office Action dated Oct. 22, 2015, for U.S. Appl. No. 14/019,404, filed Sep. 5, 2013, 6 pages.
Non-Final Office Action dated May 22, 2017, for U.S. Appl. No. 14/200,302, filed Mar. 7, 2014, 14 pages.
Non-Final Office Action dated May 3, 2017, for U.S. Appl. No. 14/704,828, filed May 5, 2015, 8 pages.
Non-Final Office Action dated Jul. 24, 2017, for U.S. Appl. No. 15/098,262, filed Apr. 13, 2016, 9 pages.
Non-Final Office Action dated Jun. 29, 2018, for U.S. Appl. No. 15/195,898, filed Jun. 28, 2016, 9 pages.
Non-Final Office Action dated Sep. 17, 2019, for U.S. Appl. No. 15/728,297, filed Oct. 9, 2017, 8 pages.
Non-Final Office Action dated Mar. 3, 2020, for U.S. Appl. No. 15/728,302, filed Oct. 9, 2017, 14 pages.
Non-Final Office Action dated Mar. 6, 2020, for U.S. Appl. No. 15/926,578, filed Mar. 20, 2018, 9 pages.
Notice of Allowance dated Feb. 14, 2014, for U.S. Appl. No. 14/019,370, filed on Sep. 5, 2013, 7 pages.
Notice of Allowance dated Mar. 14, 2014, for U.S. Appl. No. 13/132,185, filed Aug. 17, 2011, 7 pages.
Notice of Allowance dated Mar. 14, 2016, for U.S. Appl. No. 14/019,404, filed on Sep. 5, 2013, 7 pages.
Notice of Allowance dated May 3, 2017, for U.S. Appl. No. 14/337,082, filed Jul. 21, 2014, 7 pages.
Notice of Allowance dated Aug. 25, 2017, for U.S. Appl. No. 14/337,082, filed Jul. 21, 2014, 7 pages.
Notice of Allowance dated Nov. 22, 2017, for U.S. Appl. No. 14/200,302, filed Mar. 7, 2014, 5 pages.
Notice of Allowance dated Jan. 19, 2018, for U.S. Appl. No. 14/704,828, filed May 5, 2015, 7 pages.
Notice of Allowance dated Aug. 24, 2018, for U.S. Appl. No. 15/098,262, filed Apr. 13, 2016, 9 pages.
Notice of Allowance dated Sep. 11, 2019, for U.S. Appl. No. 15/195,898, filed Jun. 28, 2016, 9 pages.
Notice of Allowance dated Nov. 26, 2019, for U.S. Appl. No. 15/195,898, filed Jun. 28, 2016, 6 pages.
Park, S. et al. (2007). "Trocar-less instrumentation for laparoscopy magnetic positioning of intraabdominal camera and retractor," Surgical Technique 245:379-384.
Raman, J. (2009). "Complete Transvaginal NOTES Nephrectomy Using Magnetically Anchored Instrumentation," Journal of Endourology 23:367-371.
Rivas, H. et al. (2005). "A Magnetic Positioning System to Drive Trocarless Laparoscopic Instruments," First International Minimally Invasive Robotic Association (MIRA) Conference on Robotic Surgery, Innsbruck, Austria, Dec. 2005.
Scott, D.J. et al. (2007). "Completely transvaginal NOTES cholecystectomy using magnetically anchored instruments," Surg. Endosc. 21:2308-2316.
Scott, D. et al. (2008). "Optimizing Magnetically Anchored Camera, Light Source, Graspers, and Cautery Dissector for Transvaginal NOTES Cholecystectomy," Surgical Endoscopy 22:S244.
Scott, D. et al. (2008). "Randomized Comparison of Laparoscopic, Flexible Endoscopic, and Wired and Wireless Magnetic NOTES Cameras on Ex-Vivo and In-Vivo Surgical Performance," Gastrointestinal Endoscopy, vol. 67: AB115.
Scott, D. et al. (2008). "Transvaginal Single Access "Pure" NOTES Sleeve Gastrectomy Using a Deployable Magnetically Anchored Video Camera," Gastrointestinal Endoscopy, vol. 67: AB116.
Scott, D. et al. (2007). "Transgastric, Transcolonic, and Transvaginal Cholecystectomy Using Magnetically Anchored Instruments," Surgical Endoscopy, vol. 21: S474.
Scott, D. et al. (2007). "Completely Transvaginal Cholecystectomy Using Magnetically Anchored Instruments," Surgical Endoscopy, vol. 21: S335.
Scott, D. et al. (2007). "Short-Term Survival Outcomes Following Transvaginal NOTES Cholecystectomy Using Magnetically Anchored Instruments," Gastrointestinal Endoscopy, vol. 65: AB109.
Swain, C. et al. (2008). "Linear Stapler Formation of Ileo-Rectal, Entero-Enteral and Gastrojejunal Anastomoses During Dual and

(56) References Cited

OTHER PUBLICATIONS

Single Access "Pure" NOTES Procedures: Methods, Magnets and Stapler Modifications," Gastrointestinal Endoscopy, vol. 67: AB119.
Swain, P. et al. (2008). "Wireless Endosurgery for NOTES," Gastrointestinal Endoscopy, vol. 67: AB104.
Tan, Y. (2011). "Modeling of Magnetic Tools for Use with Superparamagnetic Particles for Magnetic Stone Extraction," 26th Engineering & Urology Society Annual Meeting, p. 29, Washington DC, May 14, 2011.
Tan, Y. (2012). "In Vitro Comparison of Prototype Magnetic Tool with Conventional Nitinol Basket for Ureteroscopic Retrieval of Stone Fragments Rendered Paramagnetic with Iron-Oxide Microparticles," The Journal of Urology, vol. 187, Issue 4, pp. e857-858.
Tang, S. (2008). "Live Video Manipulator for Endoscopy and NOTES," Gastrointestinal Endoscopy 68:559-564.
Tillander, H. (1951). "Magnetic guidance of a catheter with articulated steel tip," Acta Radiologica pp. 62-64.
Wikipedia (2015). "Stainless Steel," retrieved from https://en.wikipedia.org/wiki/Stainless_steel, 13 pages.
Written Opinion of the International Searching Authority dated Jul. 30, 2014, for PCT Application No. PCT/US2014/021537, filed on Mar. 7, 2014, 5 pages.
Written Opinion of the International Searching Authority for International Application No. PCT/IB2009/054307 dated Feb. 8, 2010.
Written Opinion of the International Searching Authority dated Jul. 18, 2014, for PCT Application No. PCT/US2014/018307, filed on Feb. 25, 2014, 5 pages.
Written Opinion of the International Searching Authority dated May 4, 2015, for PCT Application No. PCT/US2015/012319, filed on Jan. 21, 2015, 5 pages.
Written Opinion of the International Searching Authority dated Jul. 15, 2016, for PCT Application No. PCT/US2016/027385, filed on Apr. 13, 2016, 11 pages.
Written Opinion of the International Searching Authority dated Aug. 22, 2016, for PCT Application No. PCT/US2016/027390, filed on Apr. 13, 2016, 9 pages.
Written Opinion of the International Searching Authority dated Apr. 3, 2017, for PCT Application No. PCT/US2017/012628, filed on Jan. 6, 2017, 7 pages.
Zeltser, I.S. et al. (2007). "Single trocar laparoscopic nephrectomy using magnetic anchoring and guidance system in the porcine model," J. of Urology 178:1-4.
U.S. Appl. No. 61/113,495, filed Nov. 25, 2008, by Fernandez et al.
Notice of Allowance dated Oct. 19, 2022, for U.S. Appl. No. 15/728,297, filed Oct. 9, 2017, 8 pages.

* cited by examiner

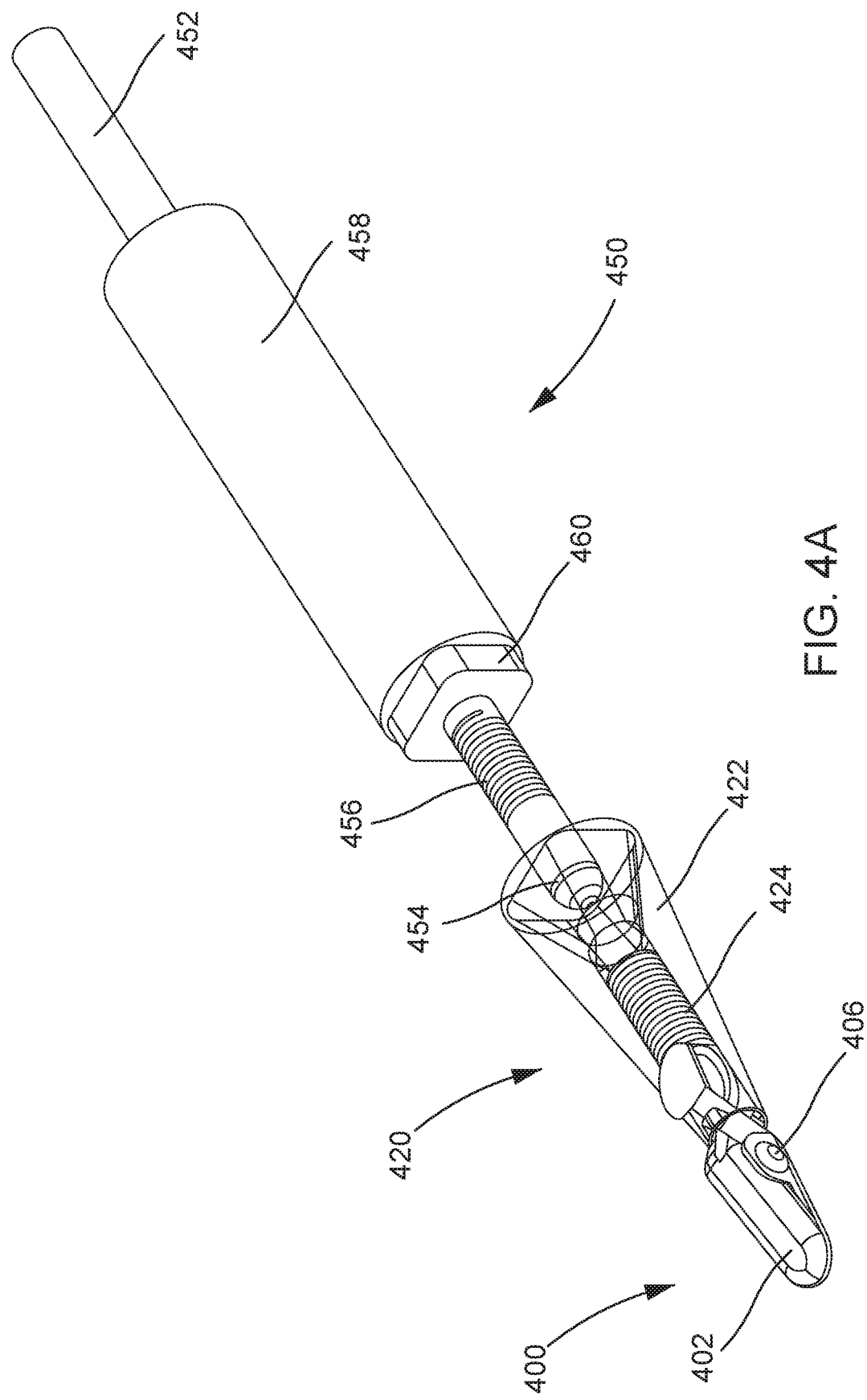

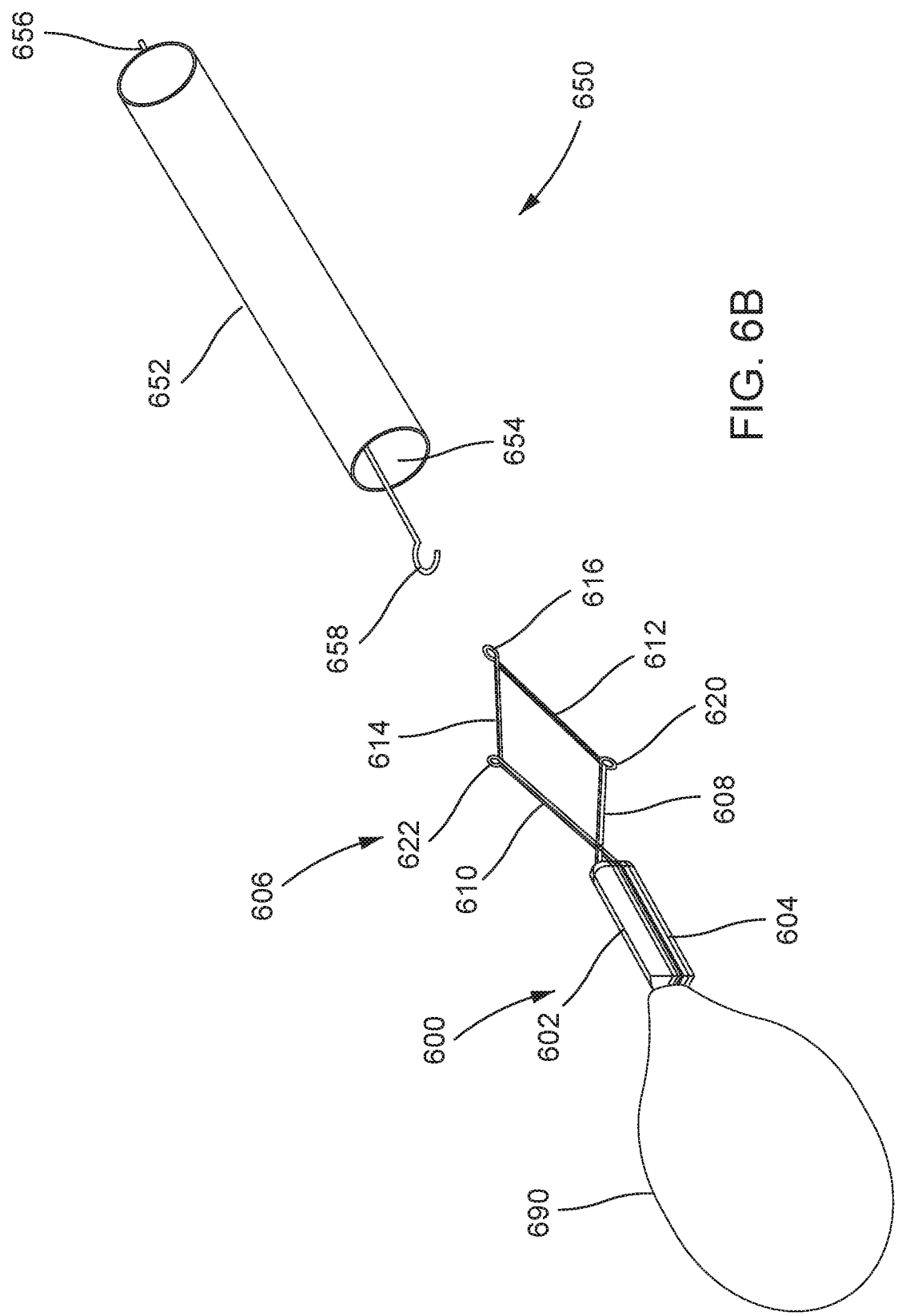

LAPAROSCOPIC GRASPERS AND SYSTEMS THEREFOR

CROSS-REFERENCE TO RELATED APPLICATIONS

This application is a divisional application of U.S. patent application Ser. No. 15/195,898, filed on Jun. 28, 2016, which is a continuation application of International Patent Application No. PCT/US2015/012319, filed on Jan. 21, 2015, which claims priority to U.S. Provisional Application Ser. No. 61/929,918, filed on Jan. 21, 2014, and titled "Laparoscopic Graspers and Systems Therefor," the contents of each of which are hereby incorporated in their entirety.

FIELD

The present invention is directed toward systems, devices, and methods for providing remote manipulation or traction to tissue using one or more graspers, delivery devices, and magnetic control assemblies.

BACKGROUND OF THE INVENTION

Many surgical procedures are shifting toward the use of minimally-invasive approaches that are configured to minimize the number and size of incisions that are made in a patient. Minimally-invasive procedures such as endoscopic and laparoscopic procedures may be associated with lower pain, quicker post-surgical recovery, shortened hospitalization, and reduced complications when compared to open surgical procedures. During minimally-invasive procedures it may be desirable to reposition or otherwise manipulate tissue. However, the introduction of additional devices to engage tissue may crowd the access sites provided by incisions, which may require the formation of larger or additional access sites. Accordingly, it may be desirable to provide one or more systems that allow for manipulation of tissue without the need to have a portion of the device present in an access site to the body.

BRIEF SUMMARY OF THE INVENTION

Described here are systems, devices, and methods for providing remote manipulation or traction to tissue. In some variations, the systems may comprise some combination of a grasper configured to be inserted into a patient, a delivery device, and a magnetic control element. The grasper may be configured for insertion into the patient during a minimally-invasive procedure, such as a laparoscopic operation. The graspers described here may be configured to releasably connect to tissue. In some embodiments, the grasper may comprise a clip, a clamp, a suction device, a coil, or the like, and may be configured to connect to any suitable tissue of the body (for example, including but not limited to tissue in the abdominal cavity, such as an appendix, a gallbladder, or the like). Accordingly, the grasper may be sized such that it may fit through a laparoscopic port (e.g., a 10 mm port or the like) or another incision formed in the body. In some instances, the grasper may be introduced into the body via an incision or port using a delivery device. The delivery device may be configured to releasably engage the grasper to deliver the grasper, remove it from the patient, or reposition it. The delivery device may additionally be configured to actuate the grasper to attach it to tissue and/or detach it from tissue. The grasper may be further configured to be manipulated by a magnetic control element positioned externally of the body to move, reposition, and/or hold the grasper.

The grasper may be any suitable device for releasably connecting to tissue, such as those described here. In some variations, the grasper may be a clip, clamp, or the like, which may attach to tissue by pressing or otherwise holding tissue between two surfaces. In other variations, the grasper may be a suction device, which may attach to tissue by creating a vacuum between the grasper and tissue. In yet other variations, the grasper may comprise a wire having a pre-formed shape such as a coil, which may attach to tissue by ensnaring it. The delivery devices may be any suitable device configured to deliver the grasper to the area of the tissue of interest, and the delivery device may be further configured to actuate the grasper to selectively connect the grasper to tissue or to detach the grasper from tissue.

The magnetic control element may be configured to be positioned outside the body and to provide a magnetic force to the grasper when the grasper is positioned inside the body. The magnetic field produced by the magnetic control assembly may provide one or more forces to the grasper to control the position of the grasper and the attached tissue. The magnetic control element may have any suitable configuration, and in some variations may comprise at least one magnet configured to generate a magnetic field and at least one force modulation device. The force modulation device may control the magnitude of the force applied to the magnetic device.

In some variations, the systems described herein comprise a system for manipulating tissue, comprising a grasper configured to be attached to tissue in a body of a patient, a delivery device configured to releasably engage the grasper and to actuate the grasper between a first configuration and a second configuration, and a magnetic control assembly comprising a magnet configured to generate a magnetic field and to apply a magnetic force to the grasper. In some variations, the grasper comprises a magnetic or ferromagnetic material. In some of these variations, the grasper further comprises two members connected by a pivot joint, wherein the two members are configured to attach to tissue by holding the tissue between the two surfaces. In some of these variations the delivery device comprises a cylindrical shaft having a lumen therethrough and a collet having a lumen therethrough and configured to be located at least partially within the lumen of the cylindrical shaft, wherein the grasper is configured to be located at least partially within the lumen of the collet and to be actuated by motion of the cylindrical shaft relative to the collet. In some of these variations, the grasper and delivery device each comprise a central longitudinal axis, and wherein the grasper is configured to be engaged by the delivery device when the central longitudinal axis of the delivery device is offset from the central longitudinal axis of the grasper by up to 90 degrees. In some variations, the grasper is configured to attach to tissue using suction. In some variations, the grasper comprises a wire having a coiled shape in the second configuration, and wherein the coiled shape is configured to ensnare tissue. In some variations, the grasper comprises two arms having an open configuration and a closed configuration, wherein the arms are configured to attach to tissue by holding the tissue between two surfaces in the closed configuration, and wherein the two arms are connected via a linkage assembly having an expanded configuration and a collapsed configuration and comprising a plurality of struts and a plurality of pivot joints. In some of these variations, the two arms can be moved from the open configuration to the closed configuration by moving the linkage assembly from the expanded configuration to the collapsed configuration. In some of these variations, the two arms can be moved from the open configuration to the closed configuration by moving the linkage assembly from the collapsed configuration to the expanded configuration.

In some variations, the methods described herein comprise a method of performing minimally invasive surgery, comprising positioning a grasper within a body of a patient using a delivery device, attaching the grasper to tissue within the body of the patient using the delivery device to actuate the grasper, disengaging the delivery device from the grasper, positioning a magnetic control assembly externally of the body, wherein the magnetic control assembly comprises a magnet configured to generate a magnetic field and apply a magnetic force to the grasper, and applying the magnetic force to the grasper to manipulate the magnetic device. In some variations, the methods further comprise reengaging the grasper with the delivery device. In some of these variations, the method further comprises using the delivery device to actuate the grasper to detach the grasper from the tissue. In some of these variations, the method further comprises repositioning the grasper to a new area of tissue.

BRIEF DESCRIPTION OF THE DRAWINGS

FIGS. 4A-4B depict perspective and side views, respectively, of a variation of the systems described here

FIGS. 6A-6B depict side and perspective views, respectively, of a variation of the systems described here.

DETAILED DESCRIPTION OF THE INVENTION

Described here are devices, systems, and methods for providing remote manipulation of tissue during minimally-invasive procedures. Generally, the systems described here include a grasper that is configured to be releasably connected to tissue. The grasper may be further configured to be attracted to one or more magnets positioned externally of the body. The systems described here may also comprise a delivery device. The delivery devices described here are generally configured to releasably carry the grasper, and may be further configured to actuate the grasper to selectively connect the grasper to tissue or detach the grasper from tissue. The delivery devices are typically further configured to release the grasper from the delivery device (e.g., after the grasper has been connected to tissue). In some variations, the system may further comprise a magnetic control element comprising one or more magnets, which may be configured to be positioned outside the body and to provide a magnetic force to the grasper when the grasper is positioned in the body. While illustrative examples of the graspers and delivery devices are described together herein, it should be appreciated that any of the graspers may be actuated and delivered using any suitable delivery device, and that that the delivery devices described here may be used to actuate and deliver any suitable grasper.

Generally, the methods described here comprise releasably connecting a grasper (such as one of the graspers described here) to a tissue, and providing a magnetic force to the grasper to move and/or hold the grasper and to provide traction of the tissue engaged by the grasper. The magnetic force may be provided by a magnetic control element configured to magnetically attract the grasper from a position outside the body. In some variations, the grasper may be releasably connected to a tissue inside of the body, and the magnetic control element may be positioned externally of the body to magnetically attract the grasper. To connect the grasper to the tissue, the grasper may be releasably coupled with a delivery device, wherein the delivery device is configured to actuate the grasper. The delivery device may actuate the grasper to releasably connect the grasper to tissue, and may decouple from the grasper after the grasper is connected to tissue. In some instances, the delivery device may be used to repositioned the grasper and reattached it to tissue (either the same tissue or a different tissue), or to remove the grasper and/or tissue from the body.

Devices and Systems

Figure 1A:
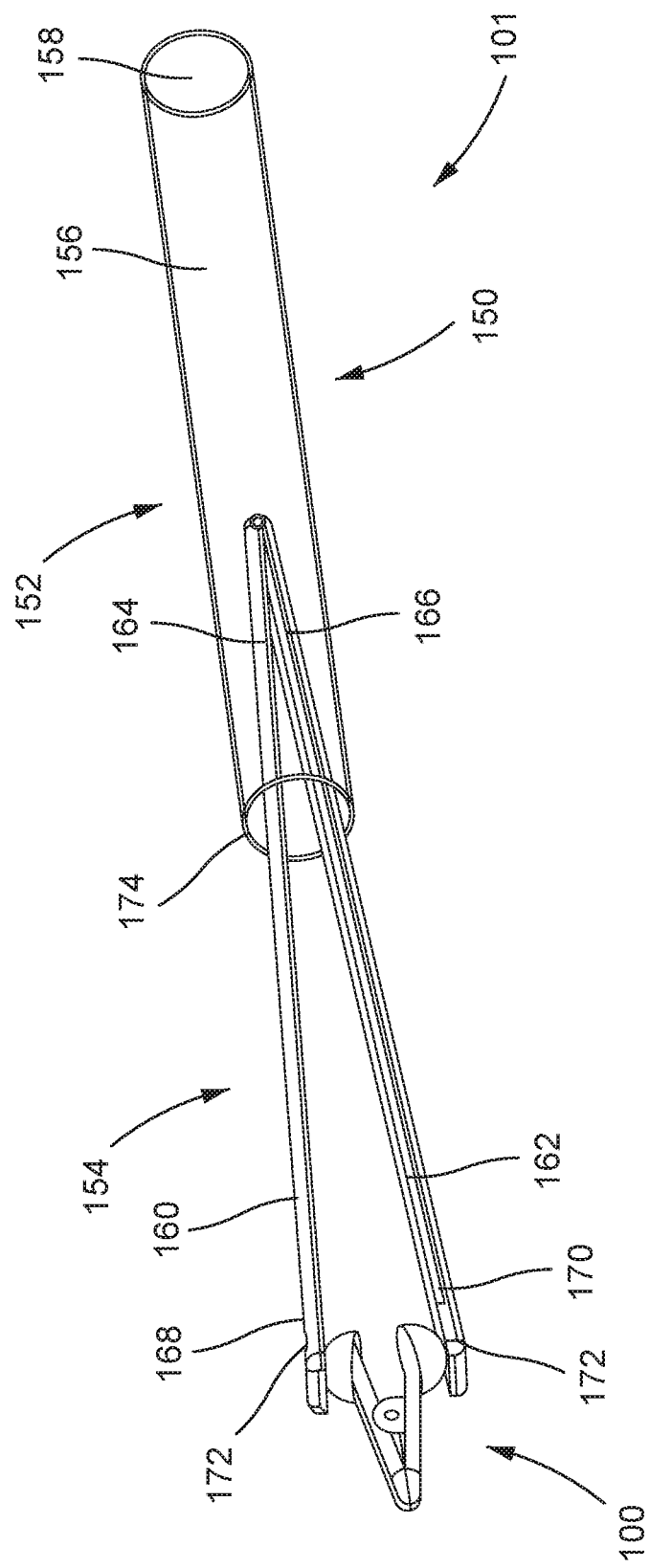
FIGS. 1A-1C depict perspective views of a variation of the systems described here having a grasper and a delivery device.
Figure 1B:
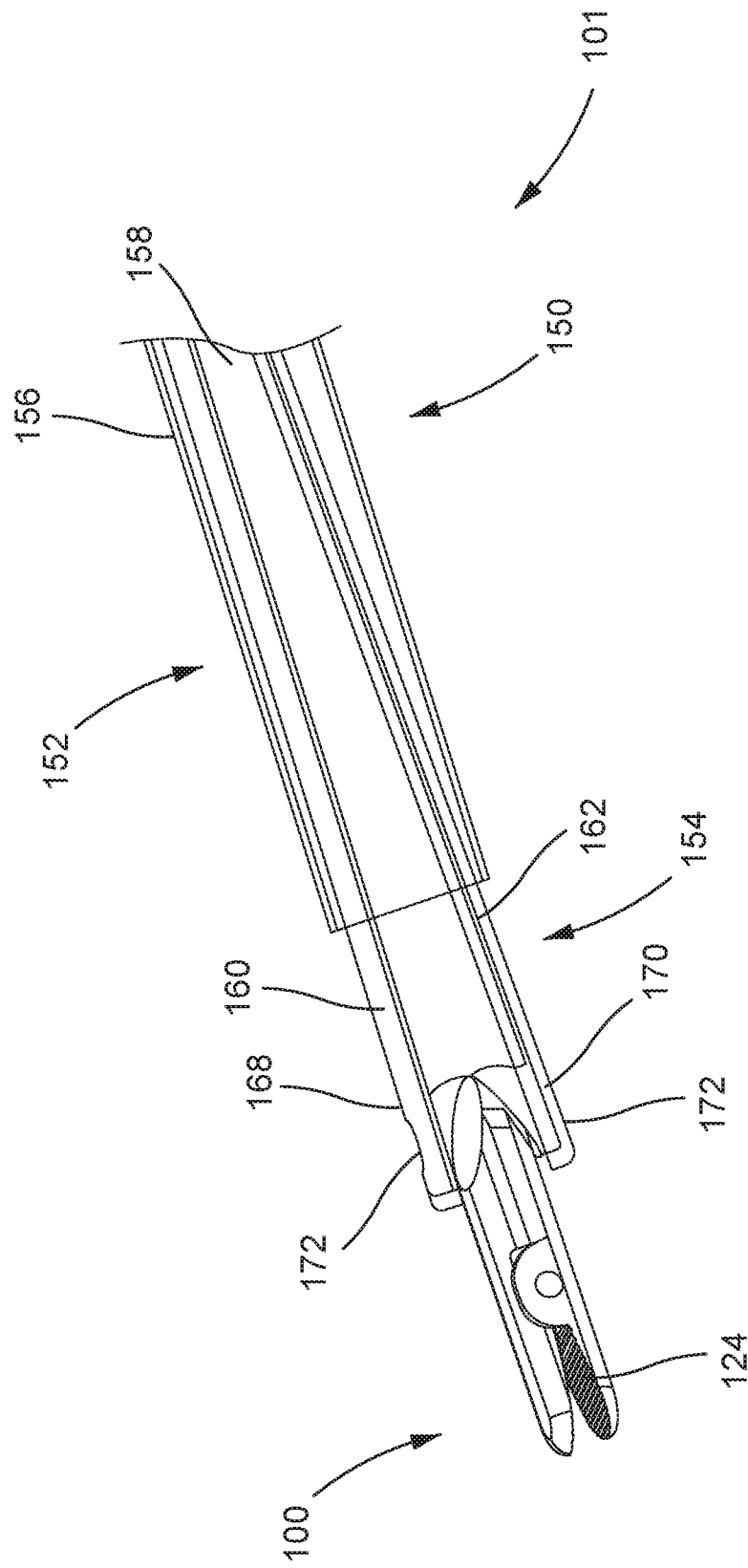
Figure 1C:
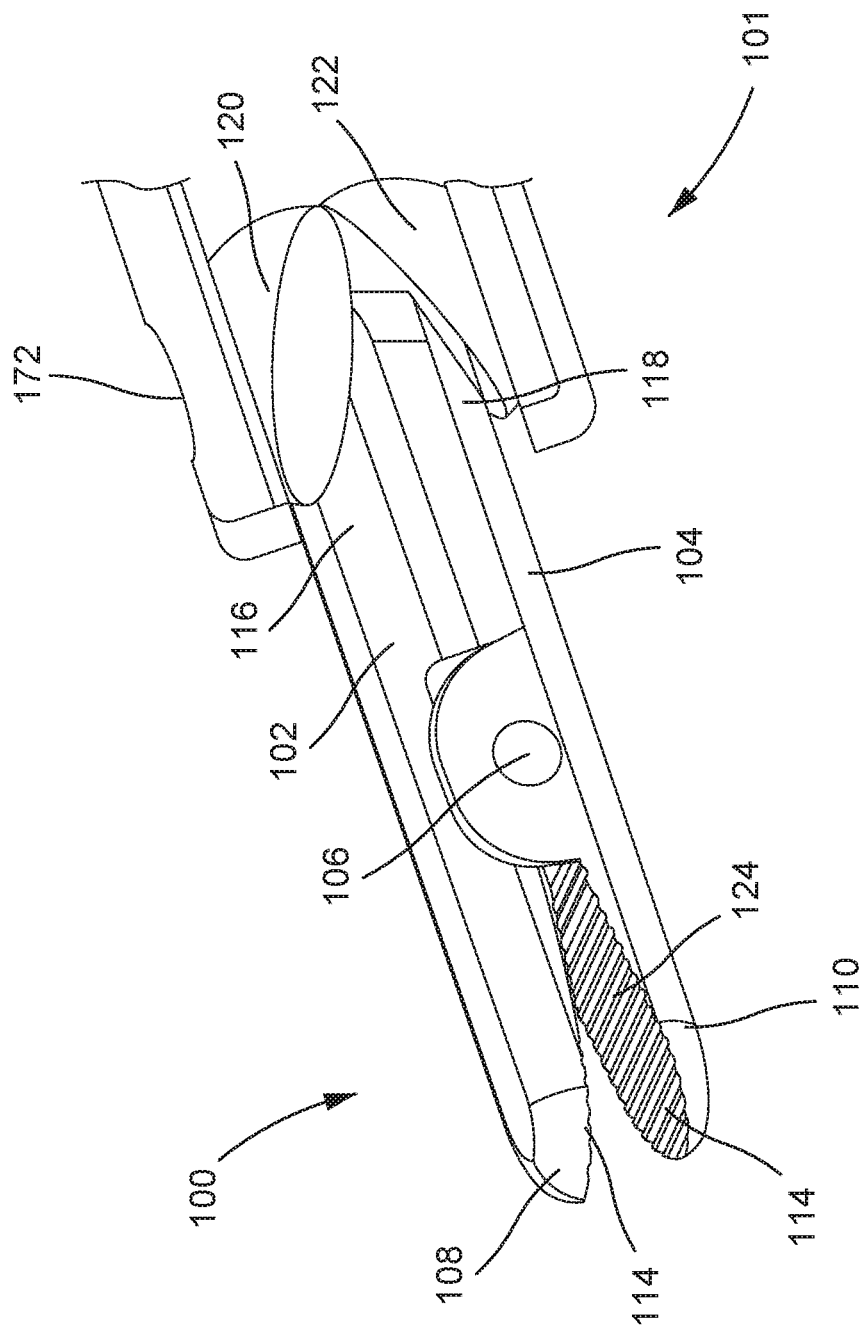

As mentioned above, the systems described here may comprise a grasper configured to be releasably connected to tissue. In some variations, the grasper may comprise a clip, clamp, or the like, which is configured to attach to tissue by pressing or otherwise holding tissue between two surfaces. FIGS. 1A-1C depict perspective views of one variation of a system 101 as described here. As shown there, the system 101 may comprise a grasper comprising a clip 100 and a delivery device 150. The clip 100 may be releasably coupled to the delivery device 150 (as shown in FIGS. 1A-1C), and may be decoupled from the delivery device. When the clip 100 is coupled to the delivery device 150, the delivery device 150 may actuate the clip 100 between an open configuration (as shown in FIGS. 1B and 1C) and a closed configuration (as shown in FIG. 1A) to connect the clip 100 to tissue or detach the clip 100 therefrom, as described in more detail herein.

In some variations, the delivery device 150 and the clip 100 may be configured for laparoscopic introduction into the body. In these variations, the clip 100 may be sized such that it may be advanced through a laparoscopic port. In some instances, the clip 100 may be sized such that it may fit through a laparoscopic port when the clip 100 is in the open configuration, in the closed configuration, or either the open or closed configuration. In some of these variations, the largest width of the clip 100 in a closed configuration may be less than or equal to about 10 mm, so that the clip 100 may be advanced through a 10 mm laparoscopic port when the clip is in the closed configuration. Similarly, a distal portion of the delivery device 150 may also be sized such that it may fit through a laparoscopic port. In some variations, the delivery device 150 may be configured such that the distal portion of the delivery device 150 (e.g., a cylindrical wall 156, as discussed in more detail herein) may have a diameter less than or equal to about 10 mm. The clip 100 and delivery device 150 may be formed from any suitable materials, such as one or more of medical grade, high-strength plastics or metals, such as stainless steel, cobalt chromium, nickel titanium, PEEK, one or more nylons, polyimide, or the like, and/or may at least partially be formed from magnetic materials, as described herein. Additionally, in some instances a portion of the delivery device (such as a shaft of the delivery device) may have a diameter of about 5 mm or less, such that additional devices may be introduced through a 10 mm port while the delivery device is positioned in the port.

The clip 100 illustrated in FIGS. 1A-1C may be configured to releasably pinch or grip tissue. As shown in FIG. 1C, the clip 100 may comprise a first lever arm 102 having a distal portion 108 and a second lever arm 104 having a distal portion 110 rotatably attached to each other by a pivot joint 106. The first lever arm 102 and the second lever arm 104 may be rotated relative to each other to actuate the clip 100 between closed and open configurations to releasably connect the clip 100 to tissue or release the clip 100 from tissue, respectively. In the open configuration, the distal portions 108 and 110 of the first lever arm 102 and the second lever arm 104, respectively, may be rotationally positioned away from each other to define a space between the distal portions 108 and 110 of the first lever arm 102 and second lever arm 104, such as shown in FIGS. 1B-1C. Similarly, when the clip 100 is in a closed configuration, the distal portions 108 and 110 of the first lever arm 102 and the second lever arm 104 may be rotationally biased toward each other to reduce or eliminate the space between the distal portions 108 and 110 of the first lever arm 102 and the second lever arm 104. While the distal portions 108 and 110 of the first lever arm 102 and the second lever arm 104 are shown in FIG. 1A as contacting each other, it should be appreciated that when clip 100 is connected to tissue, tissue positioned between the first and second lever arms 102 and 104 may prevent the distal portion 108 of the first lever arm 102 from contacting the distal portion 110 of the second lever arm 104 when the clip 100 is placed in the closed configuration. In some variations, the distal portions 108 and 110 of the first lever arm 102 and the second lever arm 104 may be rotationally biased toward each other. For example, in some variations the clip 100 may comprise a spring, such as a torsional spring, which may spring-bias the distal portions 108 and 110 of the first and second lever arms 102 and 104, respectively, toward each other, which in turn may bias the clip 100 into a closed position. The bias toward the closed configuration may act to hold tissue positioned between the distal portions 108 and 110 of the first lever arm 102 and the second lever arm 104.

The distal portions 108 and 110 of the first and second lever arms 102 and 104, respectively, may comprise one or more features that may promote engagement with tissue, but need not. In some variations, one or both of inner surfaces 112 and 114 of the distal portions 108 and 110, respectively, may be roughened or texturized, which may help to reduce slipping between the lever arms and tissue. Additionally or alternatively, the inner surfaces 112 and/or 114 may comprise teeth or ridges 124 (such as shown in FIGS. 1B-1C) or other projections that may facilitate engagement of the first and second lever arms 102 and 104 with tissue. In some variations of the clip described here, the clip may comprise one or more coatings that may help to smooth discontinuities in the contours of the clip and may act to provide one or more atraumatic surfaces of the clip. The one or more coatings may comprise silicone, urethane, one or more nylon blends, polyethylenes, fluoropolymers, combinations thereof, and the like.

The proximal ends 116 and 118 of the first and second lever arms 102 and 104, respectively, may be sized and configured to be engaged by a delivery device to releasably couple the clip 100 to a delivery device (such as delivery device 150, as described in more detail herein). In general, it may be desirable for the graspers described herein to comprise external features on exposed surfaces that may promote the ability of an external instrument (e.g., a delivery device) to remain engaged with the graspers while applying a compressive force to the graspers. For example, the graspers may comprise one or more flat surfaces, recesses, guides (e.g., ridges or channels), or gently curved convex surfaces, such that the instrument is less likely to slip or change positions during grasper actuation. In the variation shown in FIGS. 1A-1C, these features may comprise protrusions at the proximal ends 116 and 118 of the first and second lever arms 102 and 104, respectively. For example, in the variation shown in FIGS. 1A-1C, the proximal ends 116 and 118 of the first and second lever arms 102 and 104, respectively, may each comprise an outwardly facing hemispherical protrusion (labeled 120 and 122 in FIGS. 1A-1C). The hemispherical protrusions 120 and 122 may be configured to engage with features on a delivery device, as described in detail herein. While the protrusions 120 and 122 shown in FIGS. 1A-1C are depicted as hemispherical, in other variations one or both of the protrusions 120 and 122 may have another shape. In some variations, one or both of the protrusions 120 and 122 may be spherical. These features may improve the ability of a delivery device to reliably grip onto the clip 100 and to exert a force on the lever arms, as described in detail herein, but need not. In some variations, these features may additionally or alternatively enable the angle between the clip 100 and the delivery device to be adjusted while the clip 100 is engaged by a delivery device, as described in detail herein.

Generally, at least a portion of the clip 100 described here may be formed from one or more materials which may be attracted to a magnetic field, as described in more detail herein, but need not be. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. In variations in which the materials include steel alloys, the steel alloys may be in a martensitic state. In some variations, coldworking may be used to improve the magnetic permeability of the clip 100, for instance during the machining process. Having at least a portion of the clip 100 formed from one or more metallic or magnetic materials that may be attracted to a magnetic field may allow the clip 100 to be manipulated by a magnetic control assembly, as will be discussed in more detail herein. In some variations, the proximal ends and/or protrusions of the clip 100 may comprise magnetic or ferromagnetic materials to facilitate engagement by the delivery device (as described in more detail herein), but need not.

Turning to the variation of the delivery device 150 shown in FIGS. 1A-1C, the delivery device 150 may comprise a barrel portion 152 and an engagement portion 154. The barrel portion 152 may comprise a cylindrical wall 156 with a lumen 158 extending therethrough, which may be sized to at least partially hold the engagement portion 154. The barrel portion 152 and the engagement portion 154 may cooperate to hold and actuate a clip (such as the clip 100 shown in FIGS. 1A-1C), as will be discussed in more detail herein.

The engagement portion 154 may comprise a first elongate member 160 and second elongate member 162. The engagement portion 154 may have an open and a closed configuration. In some variations, the first elongate member 160 and second elongate member 162 may be rotatably connected or otherwise attached at their proximal ends 164 and 166, respectively, but need not be attached. In variations in which the elongate members are attached, the attachment mechanism may allow for the engagement portion 154 to be moved between the open and closed configurations. In some variations, the attachment mechanism may be a pivot joint. In other variations, the first elongate member 160 and second elongate member 162 may be joined, welded or otherwise fused together, and the members may be sufficiently flexible to allow the engagement portion 154 to flex between closed and open configurations.

When the engagement portion 154 is moved to the open configuration, the distal portions 168 and 170 of first elongate member 160 and second elongate member 162, respectively, may be spaced apart to define a space between the distal portions 168 and 170 of first elongate member 160 and second elongate member 162, as shown in FIG. 1A. In variations in which the elongate members are attached such that an attachment mechanism rotatably connects the first and second elongate members 160 and 162, in the open configuration, the distal portions 168 and 170 of the first and second elongate members 160 and 162 may be rotationally positioned away from each other to define a space between the distal portions 168 and 170 of first and second elongate members 160 and 162. In the closed configuration, the distal portions 168 and 170 of first elongate member 160 and second elongate member 162 may be moved closer than in the open configuration, as shown in FIGS. 1B-1C. In variations in which the elongate members are attached such that an attachment mechanism rotatably connects the first and second elongate members 160 and 162, in the closed configuration, the distal portions 168 and 170 of the first and second elongate members 160 and 162 may be rotationally positioned toward each other to reduce or eliminate space between the distal portions 168 and 170 of the first and second elongate members 160 and 162.

While it may be possible for the distal portion 168 of the first elongate member 160 to be moved into contact with the distal portion 170 of the second elongate member 162, this may not be necessary for the engagement portion 154 to releasably engage a clip. For example, when the engagement portion 154 releasably engages with the clip 100 depicted in FIGS. 1A-1C, the clip 100 may prevent the distal portions 168 and 170 of the first elongate member 160 and second elongate member 162 from contacting each other, and/or may prevent the first elongate member 160 and second elongate member 162 from fully closing.

In some variations, the first elongate member 160 and the second elongate member 162 may be configured such that their distal ends 168 and 170 are biased away from each other, which may in turn bias the engagement portion 154 toward an open configuration. For example, in some variations the engagement portion 154 may comprise a spring (not shown), such as a compression spring, which may spring-bias the engagement portion 154 toward an open position, such as shown in FIG. 1A. In variations where the first elongate member 160 and second elongate member 162 are welded together, they may be formed in an open configuration but may be sufficiently flexible to allow the first elongate member 160 and second elongate member 162 to be pressed toward each other into a closed configuration. In other variations, the first and second elongate members 160 and 162 may be spring-biased toward each other, for instance with an extension spring, leaf spring, or torsional spring, which may bias the engagement portion 154 toward a closed configuration. In some variations, the delivery device 150 may comprise a control that may be used to overcome the bias of an engagement portion (such as the engagement portion 154) toward a closed configuration, which may thus allow the engagement portion 154 to be moved into an open configuration.

As mentioned above, the engagement portion 154 of the delivery device 150 may be configured to releasably couple to and actuate a clip, such as the clip 100 shown in FIGS. 1A-1C. For example, in some instances the distal portions 168 and 170 of first elongate member 160 and second elongate member 162 may be configured to releasably engage the clip 100. The proximal ends 116 and 118 of the first and second lever arms 102 and 104, respectively, of clip 100 may be positioned between the distal ends 168 and 170 of the first and second elongate members 160 and 162, respectively, of the delivery device 150. The clip 100 may be held between the distal ends 168 and 170 of the first and second elongate members by a clamping force between the distal ends 168 and 170. For example, in variations in which the engagement portion 154 of the delivery device 150 is biased toward a closed configuration, the biasing force may create a clamping force.

In some variations, the distal portions 168 and 170 of the first and second elongate members 160 and 162, respectively, may comprise features that may improve the ability of the delivery device 150 to reliably grip onto a clip (such as clip 100) and to exert a force on the lever arms of a clip, but need not comprise such features. For example, the delivery device 150 may comprise apertures or recesses (e.g., apertures 172 shown in FIGS. 1A-1C) extending at least partially through the distal ends 168 and 170 of the first and second elongate members 160 and 162. When a clip is positioned between the distal ends 168 and 170 of first and second elongate members 160 and 162, at least a portion of the clip may be configured to sit within one or more of the apertures 172. For example, each of the hemispherical protrusions 120 and 122 of the clip 100 described with respect FIGS. 1A-1C may fit at least partially within a respective aperture 172. This may help to maintain engagement between the engagement portion 154 and the clip 100 by allowing a greater area of contact between the clip 100 and delivery device 150, and by the inner walls of the apertures 172 exerting inward forces on the hemispherical protrusions 120 and 122 that may tend to keep the hemispherical protrusions 120 and 122 within the apertures 172. In some variations, the hemispherical protrusions 120 and 122 may additionally be secured in the apertures 172 by a force biasing the first and second elongate members 160 and 162 toward each other, as described herein.

Additionally or alternatively, features of the proximal ends 116 and 118 of the first and second lever arms 102 and 104, respectively, of the clip 100, and/or features of the distal portions 168 and 170 of the first and second elongate members 160 and 162, respectively, of the delivery device 150 may enable a clip (such as clip 100) to be engaged by a delivery device (such as delivery device 150) from a broad range of angles (e.g. angles of approach wherein the central longitudinal axis of the grasper is offset from the central axis of the delivery device by up to 10°, 20°, 30°, 40°, 50°, 60°, 70°, 80°, 90°, or more), assist in delivery and/or retrieval of the grasper, and/or assist in locating the clip 100 for retrieval. For example, the outwardly facing hemispherical protrusions 120 and 122 on proximal ends 116 and 118 of the first and second lever arms 102 and 104 of clip 100 enable the clip to be accessed from a broad range of angles because the rounded surface creates a partially rotationally symmetric contact area for a delivery device. The outwardly facing hemispherical protrusions 120 and 122 may also enable the clip 100 to be more easily located because of the larger size of the hemispherical protrusions 120 and 122 as compared to the proximal ends 116 and 118 of the first and second lever arms 102 and 104.

In some variations, there may be an attractive force between distal portions 168 and 170 of first and second elongate members 160 and 162 and one or more portions of the clip 100 (e.g., the distal portions 116 and 118 and/or protrusions 120 and 122). In some variations, this attractive force may be magnetic. In variations in which the attractive force is magnetic, the magnetic force may be generated by the distal portions 168 and 170 of the first and second elongate members 160 and 162, and one or more portions of the clip 100, wherein each of these components comprises one or more magnetic or ferromagnetic materials. For example, in variations in which one or more portions of a clip (e.g., the distal portions 116 and 118 and/or protrusions 120 and 122 of the clip 100) comprise magnetic materials, the distal portions 168 and 170 of the elongate members 160 and 162 may comprise magnetic or ferromagnetic materials; in variations in which one or more portions of a clip (e.g., the distal portions 116 and 118 and/or protrusions 120 and 122 of the clip 100) comprise ferromagnetic materials and no magnetic materials, the distal portions 168 and 170 of the elongate members 160 and 162 may comprise magnetic materials.

When the delivery device 150 has engaged a clip (such as clip 100 shown in FIGS. 1A-1C), the delivery device 150 may additionally be configured to actuate the clip between open and closed configurations. To move the clip 100 between its open and closed configurations, the engagement portion 154 may be selectively moved between its open and closed configurations, respectively. For example, as the engagement portion 154 is moved toward its closed configuration (such as shown in FIG. 1B), the distal portions 168 and 170 of the first and second elongate members 160 and 162 may be moved toward each other. This may apply a compressive force to the proximal ends 116 and 118 of first and second lever arms 102 and 104 of clip 100, which may in turn cause the first and second lever arms 102 and 104 to rotate toward an open configuration. Conversely, moving the engagement portion 154 toward its open configuration may move the distal ends 168 and 170 of the first and second elongate members 160 and 162 away from each other. This may in turn allow the clip 100 to return to its closed configuration, such as shown in FIG. 1A.

The engagement portion 154 may be moved between its open and closed configurations in any suitable manner. In some variations, the engagement portion 154 may be actuated by advancing or retracting the engagement portion 154 through the lumen 158 of cylindrical wall 156 of the delivery device 150. Movement of the cylindrical wall 156 distally relative to the engagement portion 154 may cause the inner surface of cylindrical wall 156 at the distal end 174 to contact the outer surface of the first and second elongate members 160 and 162. Further movement of the cylindrical wall 156 distally relative to the engagement portion 154 may then cause the cylindrical wall 156 to press against the outer surfaces of the first and second elongate members 160 and 162, which may force the distance between the first and second elongate members 160 and 162 to stay substantially constant at the point where the first and second elongate members 160 and 162 contact the cylindrical wall 156. As a result, the movement of the cylindrical wall 156 distally relative to the engagement portion 154 may push the engagement portion 154 toward a closed configuration. When the engagement portion 154 is moved toward a closed configuration, distal ends 168 and 170 of the first and second elongate members 160 and 162 may be moved toward each other, which in turn may press the distal ends 116 and 118 of the lever arms 102 and 104, respectively, of the clip 100 toward each other. This may move the lever arms 102 and 104 of the clip 100 into an open configuration, as shown in FIGS. 1B-1C. Conversely, when the cylindrical wall 156 is moved proximally relative to the engagement portion 154, the cylindrical wall 156 may contact the engagement portion 154 at an increasingly proximal portion of the first and second elongate members 160 and 162, which may allow the first elongate member 160 and the second elongate member 162 to move away from each other, returning to an open configuration, as shown in FIG. 1A. This may release the pressure on the distal ends 116 and 118 of the first and second lever arms 102 and 104, respectively, of the clip 100, which in turn may cause the distal ends 116 and 118 of the first and second lever arms 102 and 104, respectively, of clip 100 to return move away from each other and to a closed configuration, as shown in FIG. 1A.

The delivery device 150 may be used to releasably attach a clip (such as clip 100 depicted in FIGS. 1A-1C) to tissue. The clip 100 may be engaged by the delivery device 150 (such as discussed in more detail herein), and the clip 100 and a distal portion of the delivery device 150 may be advanced into a patient (e.g., into a body cavity such as the abdominal cavity) through an access site (e.g., such as a laparoscopic port). Once the clip 100 is positioned within the body cavity, the delivery device 150 may be actuated to selectively move the clip 100 between its open and closed configurations in order to capture tissue between the lever arms of the clip 100, thereby allowing the clip 100 to be releasably connected to tissue. Once the clip 100 holds tissue between the first lever arm 102 and the second lever arm 104, the clip 100 may be controlled by the magnetic control assembly to manipulate the attached tissue, as discussed in more detail herein. The engagement portion 154 may then be disengaged from the clip 100 and removed from the anatomical cavity. If desirable, the delivery device 150 may subsequently reengage the clip 100 to disconnect the clip 100 from the tissue and/or reposition the clip 100.

Figure 2:
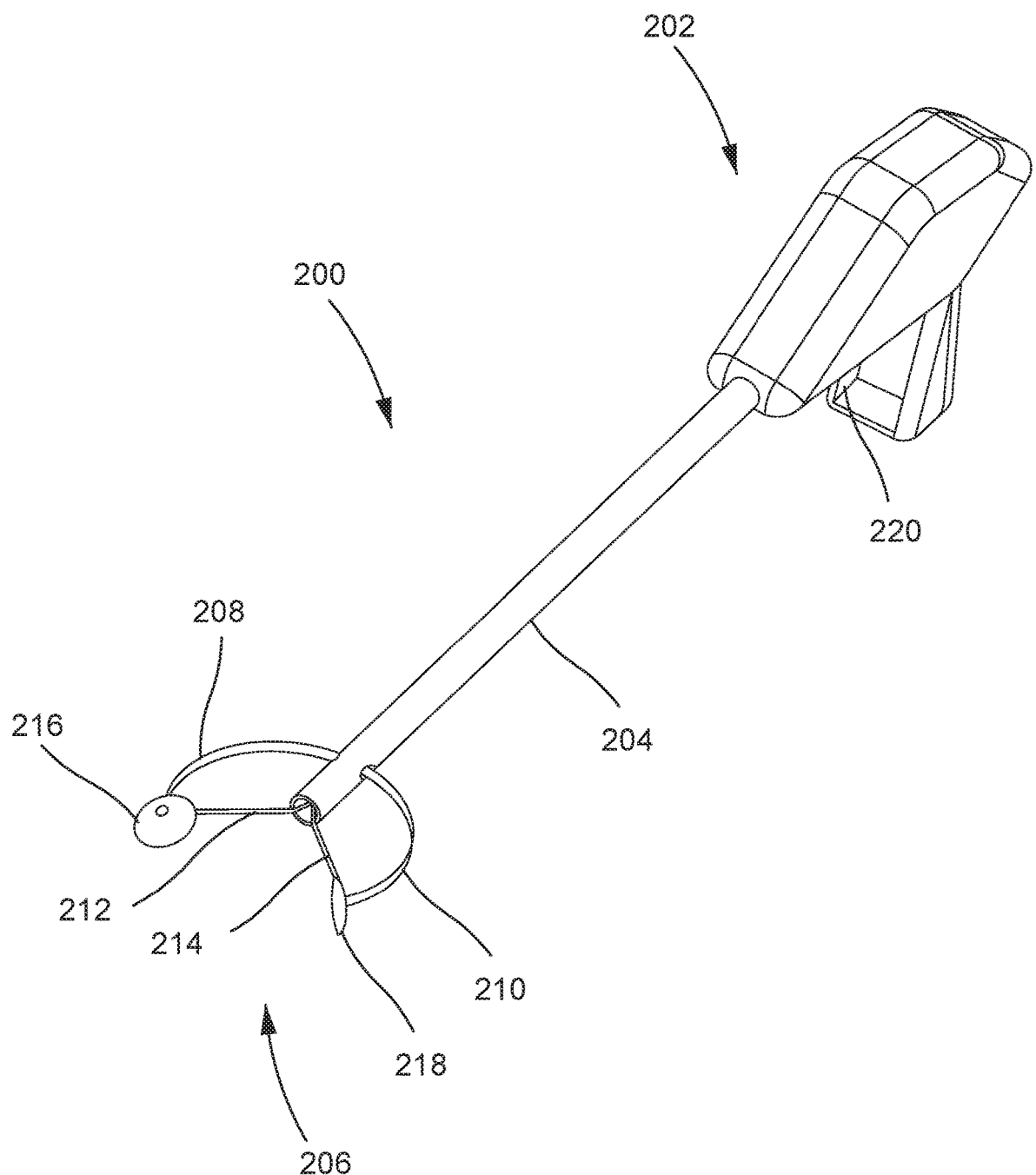
FIG. 2 depicts a perspective view of a variation of the delivery devices described here.

FIG. 2 shows another variation of a delivery device 200 that may be used to releasably engage one or more of the clips described here (such as the clip 100 described with respect to FIGS. 1A-1C). As shown there, the delivery device 200 may comprise a handle portion 202, a shaft 204 extending from the handle portion 202, and a distal engagement portion 206 at the distal end of the shaft 204.

In some variations, a distal portion of the delivery device 200 may be configured for laparoscopic introduction into the body, such as described in more detail herein. In some of these variations, the delivery device 200 may be configured for advancement through a 10 mm laparoscopic port. In some instances, the shaft 200 and the distal engagement portion 206 of the delivery device 200 may be sized such that they may fit through a laparoscopic port when the distal engagement portion 206 is in the open configuration, the closed configuration, or either the open or closed configuration. In some of these variations, the largest width of the shaft 204 and the distal engagement portion 206 in a closed configuration may be less than or equal to about 10 mm, so that at least a portion of the delivery device 200 may be advanced through a 10 mm laparoscopic port when the distal engagement portion 206 is in a closed configuration. In some of these variations, the largest width of the shaft 204 and the distal engagement portion 206 in an open configuration may be less than or equal to about 10 mm, so that at least a portion of the delivery device 200 may be advanced through a 10 mm laparoscopic port when the distal engagement portion 206 is in an open configuration. In some of these variations, the distal engagement portion 206 may have an outer diameter less than or equal to about 4 mm in the open configuration, the closed configuration, or either the open or closed configuration. In these variations, it may be possible to advance the distal engagement portion 206 through a 10 mm laparoscopic port, and to further advance a second device having a diameter of about 5 mm or less through the port while the shaft 204 is positioned in the port. It should be appreciated that the shaft 204 may have any suitable diameter (e.g., between about 1 mm and about 5 mm, between about 5 mm and about 10 mm, or the like). The shaft 204 and distal engagement portion 206 may be formed from any suitable materials, such as one or more medical-grade, high-strength plastics or metals, such as stainless steel, cobalt chromium, PEEK, one or more nylons, polyimide, or the like, and/or may at least partially be formed from materials that may be attracted to a magnetic field, as described herein.

The distal engagement portion 206 may comprise a first arm 208 and a second arm 210 having distal ends 216 and 218, respectively, which may be able to be actuated between an open configuration (as shown in FIG. 2) and a closed configuration. In some variations, the first and second arms 208 and 210 may be able to be actuated between open and closed configurations by at least one of the first and second arms 208 and 210 being configured to flex toward or away from the other. In other variations, the first and second arms 208 and 210 may be able to be actuated between open and closed configurations by at least one of the first and second arms 208 and 210 being pivotably attached to the shaft 204, such that it is configured to rotate relative to the shaft 204. In the open configuration, the first and second arms 208 and 210 may be positioned away from each other to define a space between their distal ends 216 and 218, such as shown in FIG. 2. In the closed configuration, the first and second arms 208 and 210 may be positioned closer toward each other to reduce or eliminate space between the distal portions 216 and 218 of the first and second arms 208 and 210.

Generally, the handle 202 may comprise an actuation control mechanism 220 that may be manipulated by a user to controllably actuate the distal engagement portion 206. The actuation control mechanism 220 may comprise any suitable configuration capable of actuating the distal engagement portion 206, such as but not limited to a trigger, slider, knob, or the like. The delivery device 200 may comprise actuation elements within the shaft 204, which may be connected to the actuation control mechanism 220 and/or the distal engagement portion 206. A user may selectively open and close the arms 208 and 210, as described herein, by moving the actuation control mechanism 220 between a first position and a second position. For example, when the actuation control mechanism 220 is in a first position (as shown in FIG. 2), the distal engagement portion 206 may be in a closed position. Similarly, when the actuation control mechanism 220 is in a second position, the distal engagement portion 206 may be in an open position. In some variations, once the arms (such as arms 208 and 210) are in a closed configuration, the arms may lock in the closed configuration. In variations in which there is a locking mechanism, the locking mechanism may be disabled to allow the arms to return to the open configuration.

In the variation shown in FIG. 2, the delivery device 200 may comprise two pull wires 212 and 214 that run within the shaft 204 and connect on their proximal ends to the actuation control mechanism 220 of the delivery device 200, and connect on their distal ends to the first and second arms 208 and 210. In variations in which the delivery device 200 comprises pull wires (such as pull wires 212 and 214), the pull wires may be used in any manner to move the arms (such as arms 208 and 210) between the open and closed positions. In some variations, such as the variation shown in FIG. 2, moving the actuation control mechanism from a first position to a second position may apply tension to the pull wires, which may move the arms from the closed position to the open position. The delivery device 200 may be further configured such that moving the actuation control mechanism from a second position to a first position may return the device to the closed position (e.g., the arms may be biased towards the closed position, and moving the actuation control mechanism from a second position to a first position may release the tension in the pull wires, which may allow the arms to return to the closed position).

In other instances, moving the actuation control mechanism from a first position to a second position may apply tension to the pull wires, which may move the arms from the open position to the closed position. The delivery device 200 may in these instances be further configured such that moving the actuation control mechanism from a second position to a first position may return the device to the open position (e.g., the arms may be biased towards the open position, and moving the actuation control mechanism from a second position to a first position may release the tension in the pull wires, which may allow the arms to return to the to the open position).

Accordingly, to engage the clip 100, a user may place the actuation control mechanism 220 in the second position (or an intermediate position between the first and second positions) to open (or partially open) the first and second arms 208 and 210, and the user may the move the actuation control mechanism 220 toward the first position to close the arms around the clip 100. The distal engagement portion 206 of the delivery device may be sized and configured to engage a clip (such as clip 100). In some variations, the distal portions 216 and 218 of the first and second arms 208 and 210 may comprise one or more features that may improve the ability of the delivery device 200 to reliably grip onto a clip (such as clip 100) and to exert a force on a clip, but need not comprise such features. For example, in variations in which the clip, such as clip 100, comprises protrusions at the proximal ends of the lever arms (such as proximal ends 116 and 118 of lever arms 102 and 104 of clip 100), the distal engagement portion 206 may be configured to engage the protrusions. More specifically, if the protrusions comprise outwardly facing hemispherical protrusions 120 and 122, as in clip 100 of FIGS. 1A-1C, the distal engagement portion 206 may comprise concave grips to engage the protrusions 120 and 122, respectively.

The actuation control mechanism 220 may be further moved toward the first position to press the clip 100 into an open configuration. The user may then manipulate the clip 100, using the delivery device 200, to position tissue between the first 102 and second 104 lever arms of the clip 100. With the tissue positioned between the arms, the actuation control mechanism may be moved back toward the second position to first allow the clip 100 to close, and then to release the clip 100 from the delivery device 200.

Figure 3A:
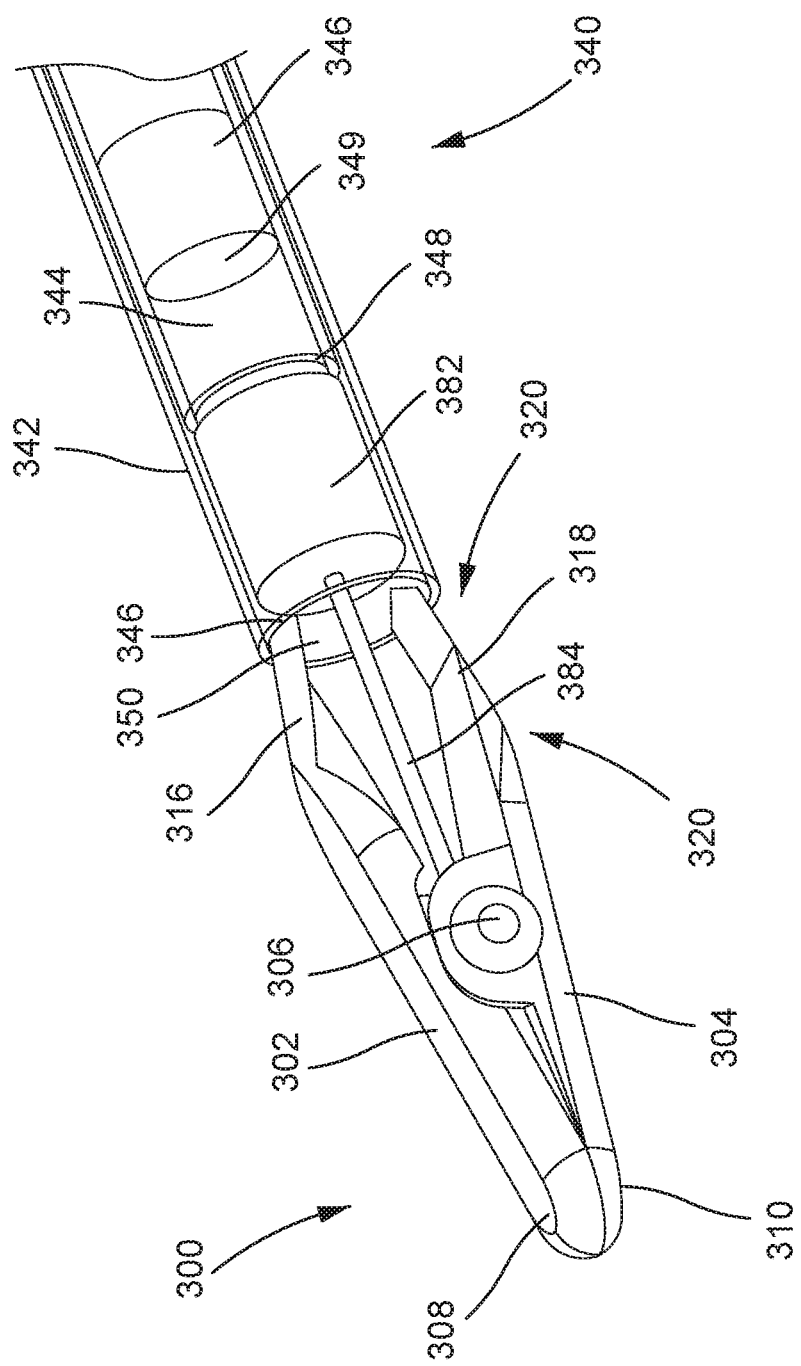
FIGS. 3A-3C depict perspective views of a variation of the systems described here.
Figure 3B:
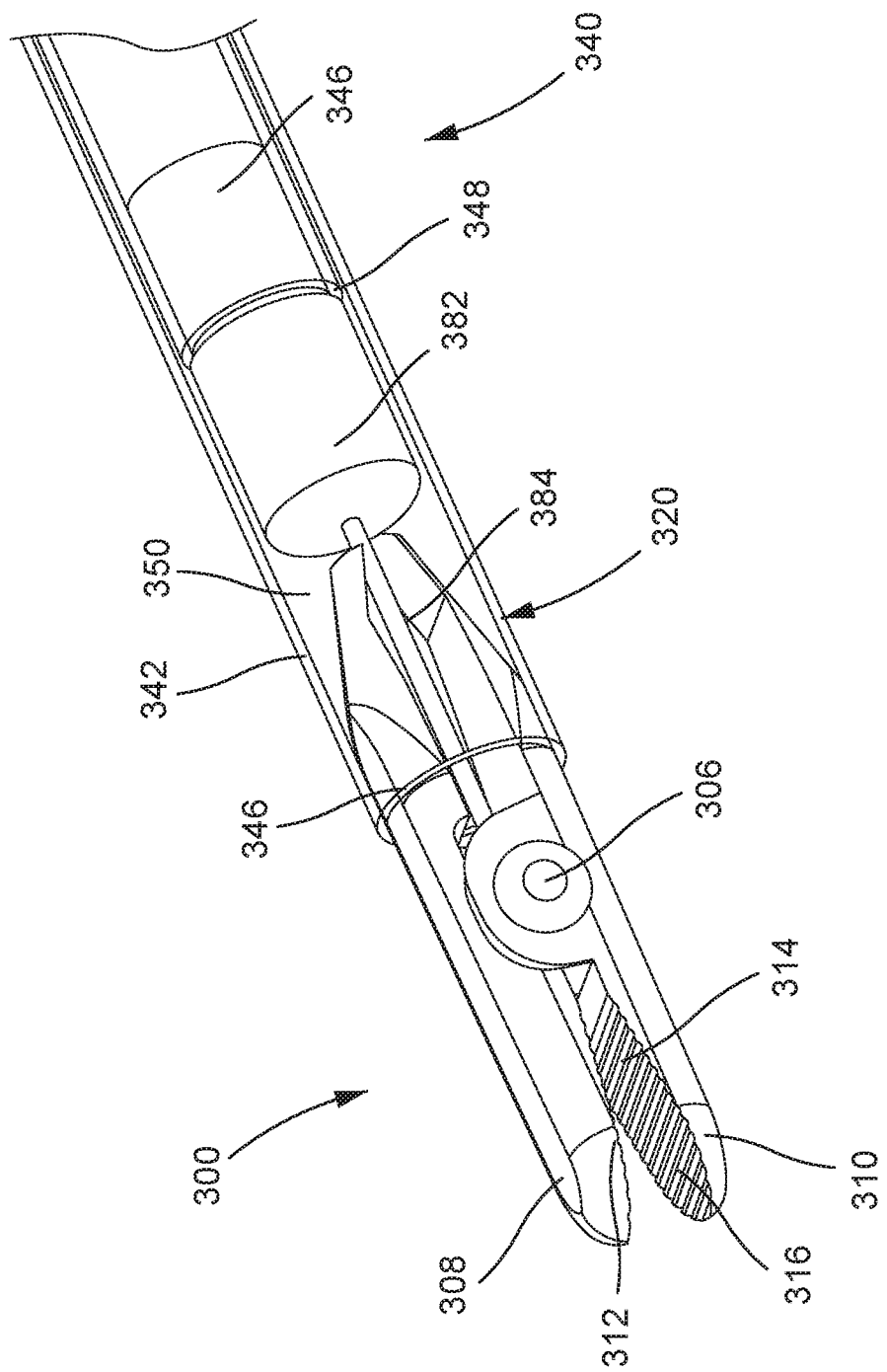
Figure 3C:
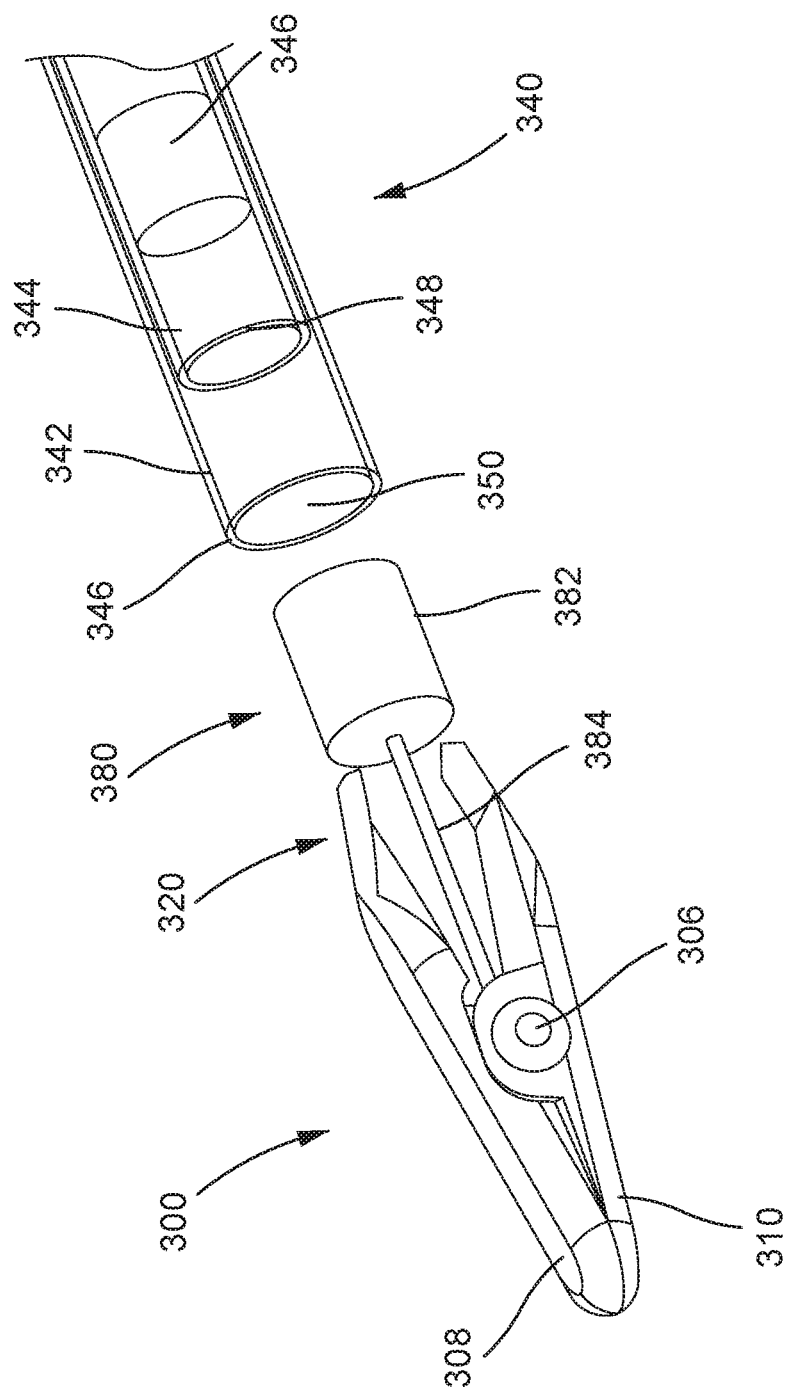

FIGS. 3A-3C depict another variation of a system in which the grasper comprises a clip. As shown there, the system may comprise a clip 300 and a delivery device 340. It should be appreciated that the clip 300 may be actuated and delivered using any suitable delivery device (such as those described here) and the delivery device 340 may be used to actuate and/or deliver any suitable grasper (such as those described here). Specifically, FIGS. 3A-3B show perspective views of the clip 300 and the delivery device 340. The clip 300 may comprise a coupling element 380, which may allow it to be releasably coupled to a delivery device 340. When the clip 300 is coupled to the delivery device 340, the delivery device 340 may actuate the clip 300 to connect the clip 300 to tissue or detach the grasper therefrom. The clip 300 and the delivery device 340 will each be discussed in more detail herein.

In some variations, the delivery device 340 and the clip 300 may be configured for laparoscopic introduction into the body, such as discussed herein. In these variations, the clip 300 may be sized such that it may be advanced through a laparoscopic port. In some instances, the clip 300 may be sized such that it may fit through a laparoscopic port when the clip 300 is in the open configuration, in the closed configuration, or in either the open or closed configuration. In some of these variations, the largest width of the clip 300 in a closed configuration may be less than or equal to about 10 mm, so that the clip 100 may be advanced through a 10 mm laparoscopic port when the clip is in the closed configuration. Similarly, a distal portion of the delivery device 340 may also be sized such that it may fit through a laparoscopic port. In some variations, the delivery device 340 may be configured such that the distal portion of the delivery device 340 may have a diameter less than or equal to about 10 mm. The clip 300 and delivery device 340 may be formed from any suitable materials, such as one or more of medical grade, high-strength plastics or metals, such as stainless steel, cobalt chromium, PEEK, one or more nylons, polyimide, or the like, and/or may be at least partially formed from materials that may be attracted to a magnetic field, as described herein.

The clip 300 illustrated in FIGS. 3A-3C may be configured to releasably pinch or grip tissue in a similar manner as the clip 100 described with respect to FIGS. 1A-1C. As shown in FIGS. 3A-3C, the clip 300 may comprise a first lever arm 302 and a second lever arm 304 attached at a pivot joint 306. The first and second lever arms 302 and 304 may be rotated relative to each other about pivot joint 306 to actuate the clip 300 between closed and open configurations to releasably connect the clip 300 to tissue or release the clip 300 from tissue, respectively. In the open configuration, the distal portions 308 and 310 of first and second lever arms 302 and 304, respectively, may be rotationally positioned away from each other to define a space between the distal portions 308 and 310 of the first and second lever arms 302 and 304, such as shown in FIG. 3B. Similarly, when the clip 300 is in a closed configuration, the distal portions 308 and 310 of the first and second lever arms 302 and 304 may be rotationally biased toward each other to reduce or eliminate space between the distal portions 308 and 310 of the first and second lever arms 302 and 304. While the distal portions 308 and 310 of the first and second lever arms 302 and 304 are shown in FIGS. 3A and 3C as contacting each other, it should be appreciated that when clip 300 is connected to tissue, tissue positioned between the first and second lever arms 302 and 304 may prevent the distal portion 308 of the first lever arm 302 from contacting the distal portion 310 of the second lever are 304 when the clip is placed in the closed configuration. In some variations, the distal portions 308 and 310 of the first and second lever arm 302 and 304 may be rotationally biased toward each other. For example, in some variations the clip 300 may comprise a spring, such as a torsional spring, which may spring-bias the distal portions 308 and 310 of the first and second lever arms 302 and 304, respectively, toward each other, which in turn may bias the clip 300 into a closed position. The bias of the lever arms toward the closed configuration may act to hold tissue positioned between the distal portions 308 and 310 of the first lever arm 302 and the second lever arm 304.

The distal portions 308 and 310 of first and second lever arms 302 and 304, respectively, may comprise one or more features which may promote engagement with tissue, but need not. In some variations, the inner surfaces 312 and/or 314 of the distal portions 308 and 310, respectively, may be roughened or texturized, which may help to reduce slipping between the lever arms and tissue. Additionally or alternatively, the inner surfaces 312 and/or 314 may comprise teeth or ridges 316 (such as shown in FIG. 3B) or other projections which may facilitate engagement of the first and second lever arms 302 and 304 with tissue. In some variations of the clip described here, the clip may comprise one or more coatings that may help to smooth discontinuities in the contours of the clip and may act to provide one or more atraumatic surfaces of the clip. The one or more coatings may comprise silicone, urethane, one or more nylon blends, polyethylenes, fluoropolymers, combinations thereof and the like.

The proximal ends 316 and 318 of lever arms 302 and 304, respectively, may be sized and configured to be engaged by a delivery device (such as delivery device 340, as described in more detail herein) to open the clip in order to engage tissue In some instances, as shown in FIGS. 3A-3C, the proximal ends 316 and 318 of lever arms 302 and 304, respectively, of the clip 300 have a tapered section 320, such that the overall diameter of the clip 300 may taper along the tapered section 320. This may facilitate actuation of the clip 300 by the delivery device 340, as described herein. In some instances, an external grasping device may also be used to actuate the clip 300 by gripping and compressing the tapered section 320.

Generally, at least a portion of the clip 300 described here may be formed from one or more materials which may be attracted to a magnetic field, as described in more detail herein, but need not be. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. In variations in which the materials include steel alloys, the steel alloys may be in a martensitic state. In some variations, coldworking may be used to improve the magnetic permeability of the clip 300, for instance during the machining process. Having at least a portion of the clip 300 formed from one or more metallic or magnetic materials that may be attracted to a magnetic field may allow the clip 300 to be manipulated by a magnetic control assembly, as will be discussed in more detail herein. In some variations, the proximal ends of the clip 300 may comprise magnetic or ferromagnetic materials to facilitate engagement by the delivery device (as described in more detail herein), but need not. In some variations, the at least a portion of the clip 300 formed from one or more materials which may be attracted to a magnetic field may be part of the coupling element 380 described below; in other variations, this magnetic portion may be distinct from the coupling element 380.

As mentioned above, the clip 300 may also comprise a coupling element 380. The coupling element 380 may facilitate engagement of the clip 300 to a delivery device (such as the delivery device 340), and may further facilitate actuation of the clip 300 between open and closed configurations, as described in detail herein. As shown in FIGS. 3A-3C, the coupling element may comprise a linking body 382 attached to the remainder of the clip 300 via a coupling rod 384. The linking body 382 may connect the clip 300 to the delivery device 340, as described in detail herein. In some variations, the linking body 382 may be configured to fit slidably within the delivery device 340. While the linking body 382 is shown as having a cylindrical shape in the variation shown in FIGS. 3A-3C, it should be appreciated that the linking body 382 may have other shapes. In some variations, such as the variation shown in FIGS. 3A-3C, the coupling rod 384 may attach to the clip 300 at or near pivot joint 306. The coupling rod 384 may be configured such that it does not interfere with the movement of lever arms 302 and 304 into an open configuration. For instance, as shown in FIGS. 3A-3C, the coupling rod 384 may comprise a rigid rod sized such that the first and second lever arms 302 and 304 do not contact the coupling rod 382 when the clip 300 is in an open configuration. At least a portion of the linking body 382 may comprise one or more materials which may be attracted to a magnetic field, which may facilitate temporary connection of the linking body 382 to a delivery device. These materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof.

Turning to the variation of the delivery device 340 shown in FIGS. 3A-3C, the delivery device 340 may comprise an outer sheath 342 having a lumen 350. At least a portion of the tapered section 320 of proximal ends 316 and 318 of the lever arms 302 and 304 may have an overall diameter that is less than that of the lumen 350 of outer sheath 342, which may allow at least a portion of the tapered section 320 to fit within the lumen 350. The clip 300 may be actuated between closed and open configurations by moving the clip 300 into and out of the lumen 350, respectively. As the clip 300 is moved into the lumen 350, the outer surfaces of the proximal ends 316 and 318 of first and second lever arms 302 and 304 may contact the inner surface of outer sheath 342. Once the outer surfaces of the proximal ends 316 and 318 contact the outer sheath 342, further movement of the clip 300 into the lumen 350 of outer sheath 342 may cause the proximal ends 316 and 318 to be pushed toward each other due to the constrained diameter of lumen 350. As the proximal ends 316 and 318 are pushed toward each other, the distal portions 308 and 310 of first and second lever arms 302 and 304 may be rotated away from each other, which may move the clip 300 into an open configuration, as shown in FIG. 3B. Conversely, movement of the clip 300 out of the lumen 350 frees the proximal ends 316 and 318 of first and second lever arms 302 and 304 from the constraint of the outer sheath 342. In variations in which the distal ends 308 and 310 of the first and second lever arms 302 and 304 are rotationally biased toward each other, this bias may help to return the clip 300 to the closed position once the proximal ends 316 and 318 of the first and second lever arms 302 and 304 are freed from the constraint of the outer sheath 342, as shown in FIG. 3A.

The clip 300 may be moved into and out of the lumen 350 of outer sheath 342 using any suitable mechanism. In the variation of the delivery device 340 shown in FIGS. 3A-3C, the clip 300 may be moved into and out of the lumen by an actuation rod 346 located slidably within lumen 350 of outer sheath 342. Actuation rod 346 may releasably engage coupling element 380 of the clip 300 by engaging with linking body 382. In some variations, the actuation rod may comprise one or more magnetic and/or ferromagnetic materials in at least its distal end 349, and thus actuation rod 346 may releasably engage linking body 382 via a magnetic attractive force when the actuation rod 346 and linking body 382 are in proximity to each other. When the actuation rod 346 and linking body 382 are engaged, retraction and advancement of the actuation rod 346 within the lumen 350 of outer sheath 342 may move the clip into and out of the lumen 350, which may in turn move the clip 300 between open and closed configurations, such as described in detail herein.

In order for releasable engagement of the actuation rod 346 and linking body 382, delivery device 340 may further comprise a depth stop that may prevent linking body 382 from moving within lumen 350 of outer sheath 342 beyond a certain point. Thus, if actuation rod 346 is moved beyond the depth stop, the force from the depth stop on the linking body 342 may overcome the engagement force connecting the actuation rod 346 and linking body 342 (e.g., magnetic attractive force), and actuation rod 346 may be disengaged from the linking body 382. In some variations, as shown in FIGS. 3A-3C, the depth stop may comprise an inner sheath 344. The inner sheath 344 may be slidably located within the outer sheath 342, and the actuation rod 346 may be slidably located within the inner sheath 344. The outer and inner sheaths 342 and 344 may be sized and configured such that the linking body 382 of the coupling element 380 may fit within the outer sheaths 342, but may be prevented from entering the inner sheath 344. The outer sheath 342, inner search 344, actuation rod 346, and linking body 382 may have a first configuration for engaging the linking body 382 with the actuation rod 346, a second configuration for moving the clip 300 into an open configuration, and a third configuration to release the linking body 382 from the actuation rod 346. In the first configuration for engaging the linking body 382 with the actuation rod 346, the distal end 349 of the actuation rod 346 may be aligned with the distal end 348 of the inner sheath 344, which may be located proximally to the distal end 346 of the outer sheath 342. The linking body 382 of clip 300 may be located within the outer sheath 342 adjacent to the distal ends 348 and 349 of inner sheath 344 and actuation rod 346, respectively, but such that the remainder of the clip 300 is located outside of the outer sheath 342. In other variations, the distal end 348 of inner sheath 344 may be located distally to the distal end 349 of actuation rod 346. In the second configuration, shown in FIG. 3B, the actuation rod 346, inner sheath 344, and clip 300 may be retracted within the outer sheath 342 relative to the first configuration, which may move the clip 300 into an open configuration, as described in detail herein. In the third configuration, the distal end 349 of the actuation rod 346 may be located proximally to the distal end 348 of the inner sheath 344, while the linking body 382 is located distally to the distal end 348 of the inner sheath 344, disengaging the actuation rod 346 and linking body 382. The positions of the inner shaft 344 and the actuation rod 346 may be controlled by any suitable mechanism or mechanisms, such as one or more trigger mechanisms on a handle portion (not shown) of the delivery device 340.

Thus, the system of FIGS. 3A-3C may be used to releasably attach the clip 300 to tissue. The clip 300 may be engaged by the delivery device 340 by the actuation rod 346 engaging with the linking body 382 of the coupling element 380. If the linking body 382 and the actuation rod 346 are engaged (e.g., held together by a magnetic attractive force), retraction and advancement of the actuation rod 349 and the clip 300 relative to the outer sheath may cause the delivery device 340 to actuate the clip 300 between open and closed configurations, respectively. As mentioned above, the proximal ends 316 and 318 of lever arms 302 and 304, respectively, of the clip 300 may have a tapered section 320. At least a portion of the tapered section 320 may have a diameter less than that of the lumen 350 of the outer sheath 342 and at least a portion may have a diameter greater than that of the outer sheath 342. Thus, when the clip 300 is coupled to the delivery device 340 via the coupling element 380, the clip 300 may be actuated between closed and open configurations by moving the actuation rod 346 proximally relative to the outer cylinder 342, which may cause the proximal ends 316 and 318 of lever arms 302 and 304 to be pushed toward each other due to the constrained diameter provided by the outer cylinder 342, as described herein. As the proximal ends 316 and 318 of lever arms 302 and 304 are pushed toward each other, the distal portions 308 and 310 of the lever arms 302 and 304 may be moved into an open configuration.

The clip 300 can then be releasably attached to tissue by moving the actuation rod distally relative to the outer cylinder 342, which may release the constraint on the proximal ends 316 and 318 of lever arms 302 and 304, which in turn may allow the distal ends 316 and 318 of lever arms 302 and 304 to be moved into a closed configuration. In variations in which the first lever arm 302 and the second lever arm 304 are rotationally biased toward each other, this bias may help to return the clip 300 to the closed position. Additionally, the bias of the lever arms toward the closed configuration may act to hold tissue positioned between the first lever arm 302 and the second lever arm 304. Once the clip 300 holds tissue between the first lever arm 302 and the second lever arm 304, the clip 300 may be controlled by the magnetic control assembly to manipulate the attached tissue, as described in more detail herein.

The clip 300 may then be decoupled from the delivery device 340. The clip 300 may be decoupled from the delivery device 340 by withdrawing the actuation rod 346 distally relative to the inner sheath 344 to a retracted position, as shown in FIG. 3C. As the actuation rod 346 is pulled proximally relative to the inner sheath 344, the clip 300 may be pulled in contact with the inner sheath 344, such as discussed herein. This engagement may prevent further proximal movement of the clip 300, and thus withdrawal of the actuation rod 346 proximally relative to the inner sheath 344 may increase the distance between linking body 382 of coupling element 380 and the actuation rod 346 of the delivery device 340. Because the force applied by a magnet decreases as a function of the distance from the magnet, moving the actuation rod 346 to a retracted position may decrease the magnetic attractive force felt by the linking body 382 of the coupling element 380. Eventually, the attractive force may be sufficiently diminished such that the coupling element 380 may decouple from the delivery device 340. In some instances, the outer sheath 342 may be withdrawn past the inner sheath 344, or the inner sheath 344 may be advanced past outer sheath, such that the diminished force allows the clip 300 to fall away from the delivery device 340. Conversely, if a portion of the clip 300 remains in the outer sheath 342, an additional force (e.g., gravity, resistance provided by the grasped tissue) may overcome the attractive force and pull the clip 300 out of the outer sheath 342. If desirable, the delivery device 340 may subsequently reengage the clip 300 to disconnect the clip 300 from tissue and/or reposition the clip 300.

Figure 3D:
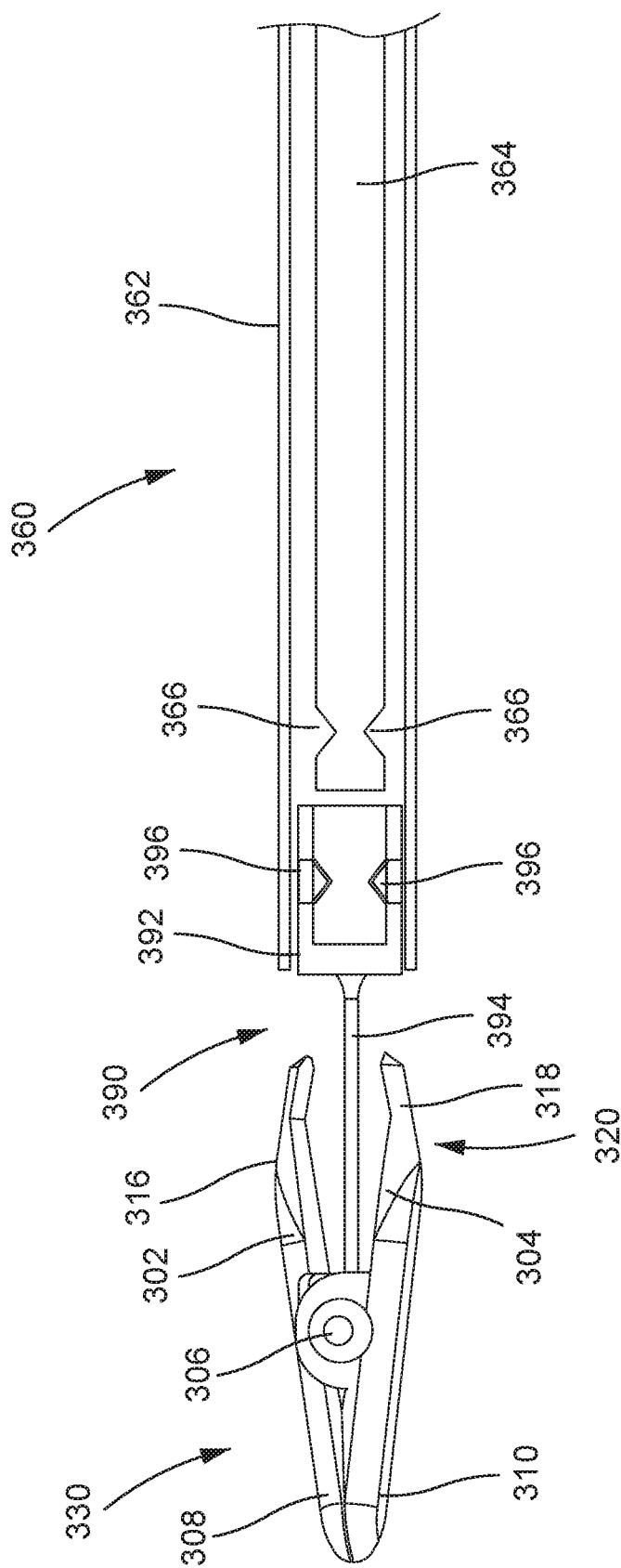
FIGS. 3D-3F depict cross-sectional side views of additional variations on the systems described here.
Figure 3E:
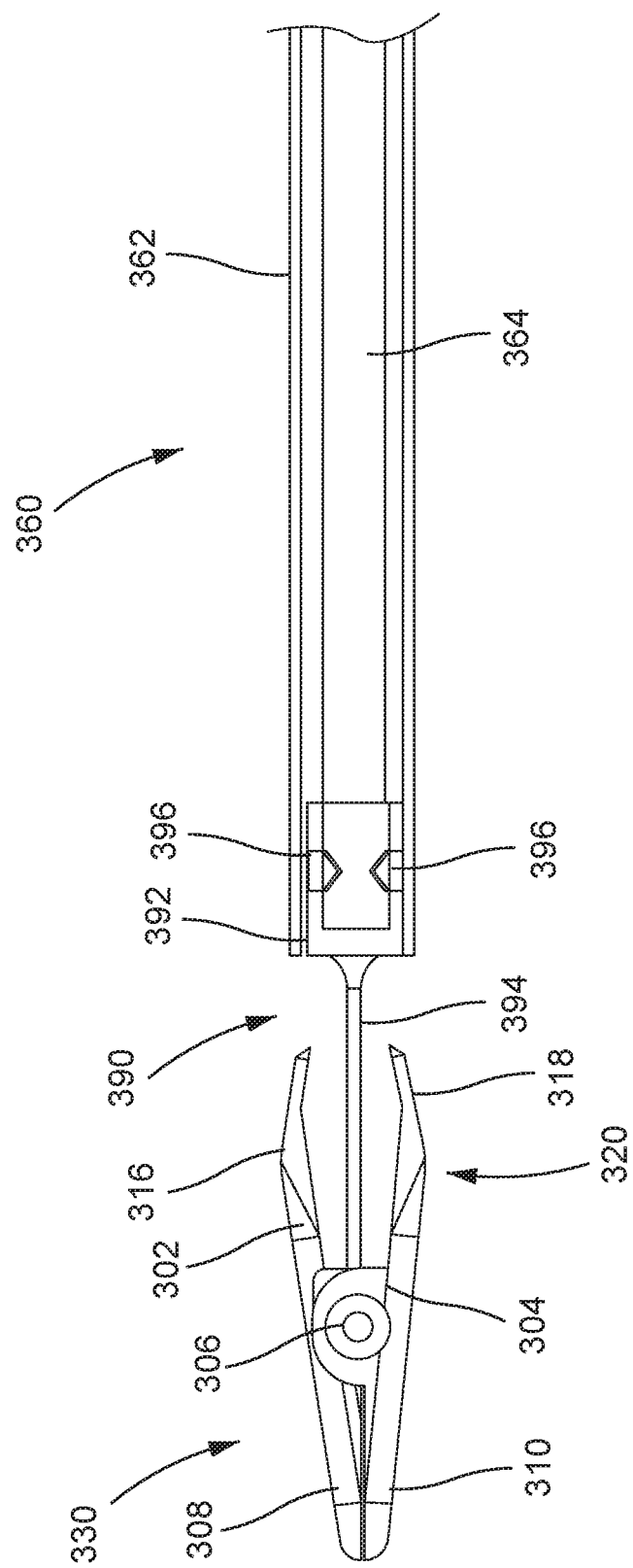

Although FIGS. 3A-3C show an actuation rod 346 configured to magnetically engage the clip 300, the actuation rod may be configured to engage the clip in any suitable manner. In some variations, for instance, the actuation rod may be configured to mechanically engage the clip. For example, FIGS. 3D-3E show cross-sectional side views of another variation of a system comprising a delivery device 360 and a clip 330. The clip 330 is similar to the clip of FIGS. 3A-3C (with identical components labeled as in FIGS. 3A-3C), but with different mechanisms for engagement by the actuation rod. The delivery device 360 may comprise an actuation rod, outer sheath, and in some variations an inner receiving cylinder.

In the variation shown in FIGS. 3D-3E, the delivery device 360 may comprise a shaft 362 and a control rod 364. The clip 330 may comprise a coupling element 390 having a receiving cylinder 392 which may be configured fit slidably within shaft 362 of the delivery device 360. The actuation rod 364 of the delivery device 360 may have a coupling element at its distal end, which mates with the locking mechanism of the clip 300. The coupling element and locking mechanism may have any design that allows the actuation rod 364 to be releasably coupled to the receiving cylinder 392. In the variation shown in FIGS. 3D-3E, the coupling element 390 may comprise a receiving cylinder 392 having a locking mechanism. The locking mechanism may comprise two spring-loaded triangular elements 396 located across from each other on the interior of receiving cylinder 392. The coupling portion of actuation rod 364 may comprise two corresponding triangular recesses 366 in the surface of control rod 364. When the actuation rod 364 is advanced distally within receiving cylinder 392, it may initially push the spring-loaded triangular elements 396 outward, and then the triangular elements 396 may snap into the recesses 366 of the actuation rod 364. When the triangular elements 396 are snapped into the recesses 366 of the actuation rod 364, the control rod 364 may resist withdrawal from the receiving cylinder 392, which may temporarily couple the coupling element 390, and in turn the clip 300, to the delivery device 360. In some variations, the distal end of actuation rod 364 may have a slightly tapered shape, so as to facilitate insertion into the open-ended cylinder 392. The delivery device 362 may comprise a release mechanism, such as a button or pull wire, which allows the locking mechanism to be released, which in turn may release the actuation rod 364 from within the receiving cylinder 392, releasing the coupling element 390 and thus the clip 300 from the delivery device 360, as shown in FIG. 3D. In some variations, the delivery device 362 may comprise an inner sheath that may allow the actuation rod 364 to be withdrawn relative to the receiving cylinder 392 to overcome the locking force provided by the spring-loaded triangular elements 396. When coupled to the clip 330, the system of FIGS. 3D-3E may be used to releasably attach, decouple, and/or reengage the clip 330 to tissue by retraction and advancement of the actuation rod 364 relative to the outer sheath 364, in a similar manner described with respect to FIGS. 3A-3C.

Figure 3F:
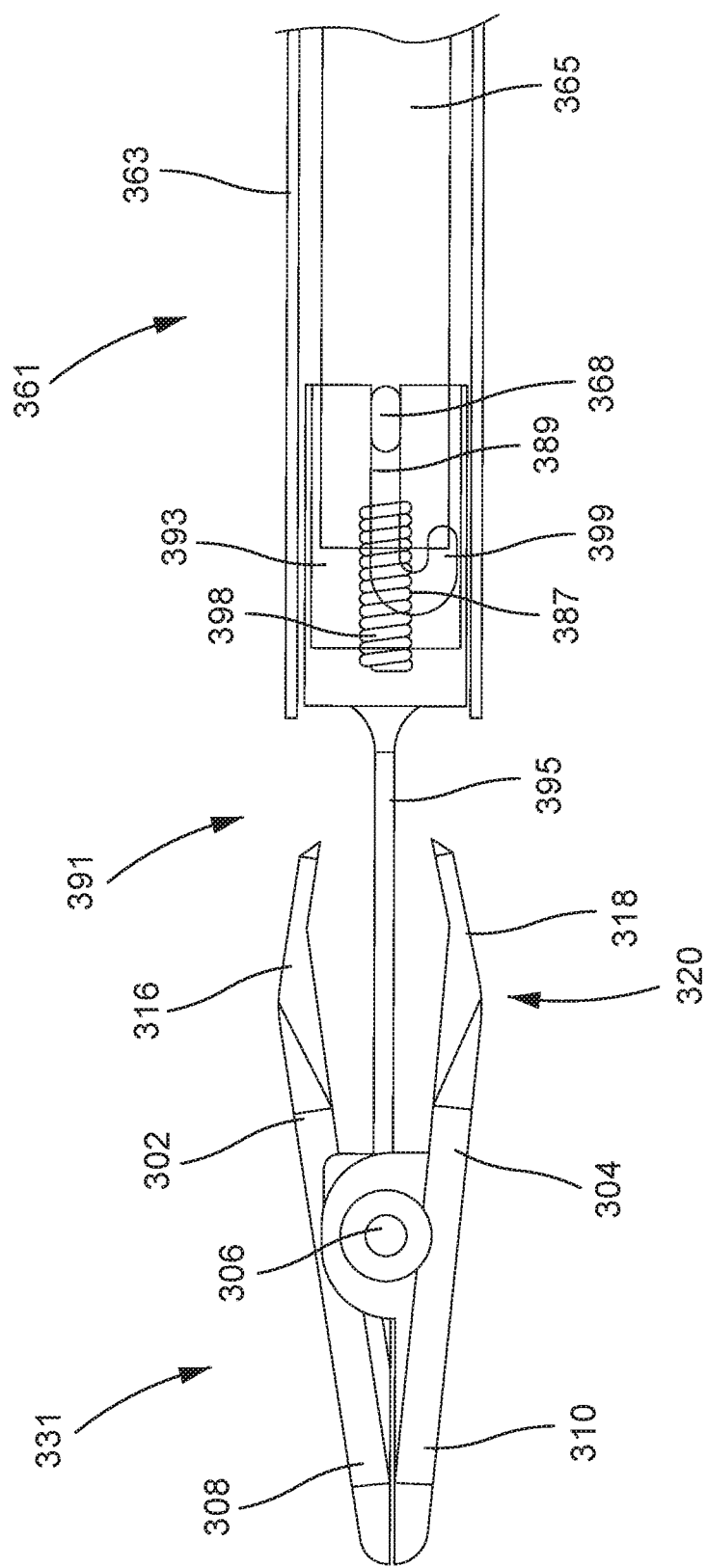

FIG. 3F shows another variation of a coupling portion and locking mechanism. Clip 331 is similar to the clip of FIGS. 3A-3C and FIGS. 3D-E (with identical components labeled as in FIGS. 3A-3E), but with a different mechanism for engagement by the actuation rod. The delivery device 361 may comprise an actuation rod, outer sheath, and an inner receiving cylinder. The locking mechanism of the coupling element 391 of clip 331 may comprise a compression spring 398 attached to the inside of the distal end of the receiving cylinder 393 and one or more substantially J-shaped tracks 399 extending from the inner lumen of the receiving cylinder 393 at least partially through the wall of the receiving cylinder 393. The receiving cylinder 393 of the coupling element 391 may be sized to fit slidably within outer shaft 363 of delivery device 361. The coupling portion of actuation rod 365 may comprise one or more tabs or protrusions 368 extending from a side surface of the actuation rod 365. Each tab/protrusion may be sized and shaped to fit within a corresponding track 399. When the actuation rod 364 is advanced distally within receiving cylinder 393, it may compress the compression spring 398, while the tab(s) or protrusion(s) 368 may follow the track 399. As the tab(s) or protrusion(s) 368 follow the track 399, they may move distally along the straight portion 389 of the cut-out(s) or recess(es) 399. The tab(s) or protrusion(s) 368 may then move around the curved portion 387 of the cut-out(s) or recess(es) 399. After having traveled proximally around the curve portion 387 of the cut-out(s) or recess(es) 399, the tab(s) or protrusion(s) 368 may be held in place by the spring 398, thus locking the actuation rod 365 into the receiving cylinder 393. In some variations, the distal end of actuation rod 365 may have a slightly tapered shape, so as to facilitate insertion into the receiving cylinder 393. The delivery device 361 may comprise a release mechanism, such as a button or pull wire, which may allow the locking mechanism to be released. In some variations, the button or pull wire may release the locking mechanism by withdrawing the tab(s) or protrusion(s) into the actuation rod 365. In other variations, the locking mechanism may be released by rotating the actuation rod 365 relative to the receiving cylinder 393. Releasing the locking mechanism may in turn may release the actuation rod 365 from within the receiving cylinder 393, which may release the coupling element 391 and thus the clip 300 from the delivery device 361. When coupled to the clip 331, the system of FIG. 3F may be used to releasably attach, decouple, and/or reengage the clip 331 to tissue by retraction and advancement of the actuation rod 364 relative to the outer sheath 365, in a similar manner described with respect to FIGS. 3A-3C.

Figure 4B:
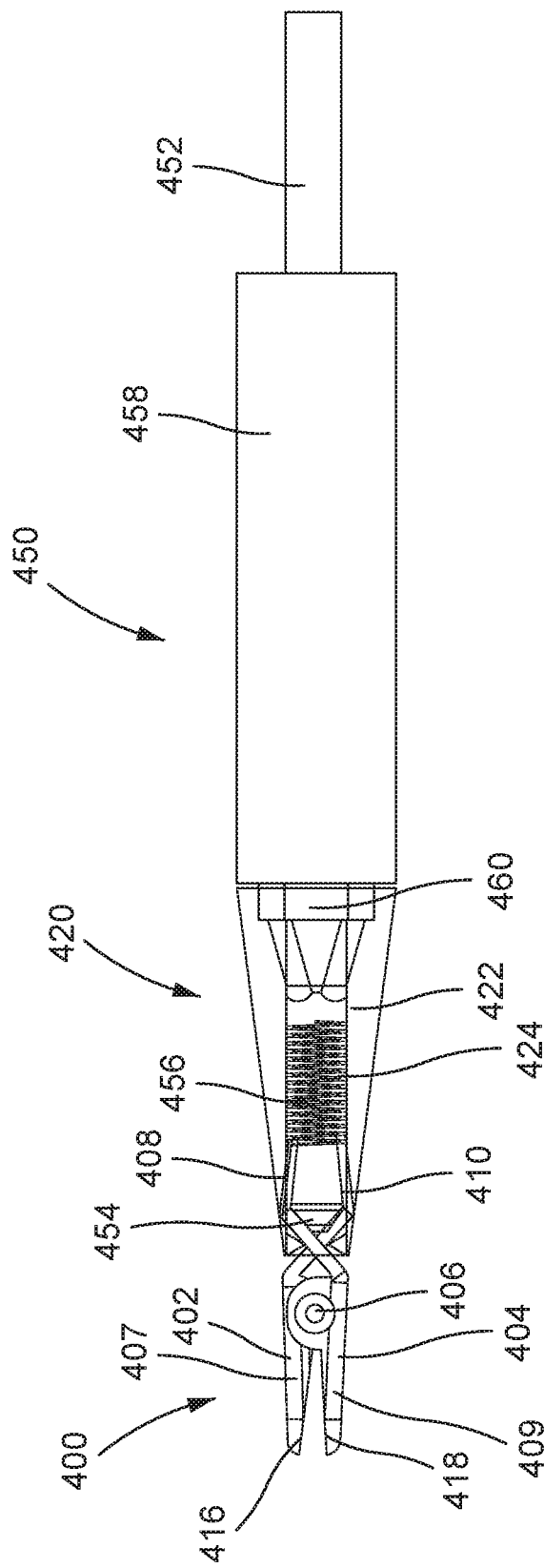

FIGS. 4A-4B depict another variation of a system as described here in which the grasper comprises a clip. Specifically, FIGS. 4A-4B show perspective and side views, respectively, of a system comprising a clip 400 and delivery device 450. The clip 400 may be releasably coupled to the delivery device 450 (as shown in FIG. 4B), and the delivery device 450 may actuate the clip 400 between open and closed configurations to connect the clip 400 to tissue or detach the grasper therefrom, respectively.

As in the other variations discussed herein, the delivery device 450 and the clip 400 may be configured for laparoscopic introduction into the body. In these variations, the clip 400 may be sized such that it may be advanced through a laparoscopic port. In some instances, the clip 400 may be sized such that it may fit through a laparoscopic port when the clip 400 is in the open configuration, the closed configuration, or either the open or closed configuration. In some of these variations, the largest width of the clip 400 in a closed configuration may be less than or equal to about 10 mm, so that the clip 400 may be advanced through a 10 mm laparoscopic port when the clip is in the closed configuration. Similarly, a distal portion of the delivery device 450 may also be sized such that it may fit through a laparoscopic port. In some variations, the delivery device 450 may be configured such that the distal portion of the delivery device 450 (e.g., actuation rod 452, as discussed in more detail herein) may have a diameter less than or equal to about 10 mm. The clip 400 and delivery device 450 may be formed from any suitable materials, such as one or more of medical grade, high-strength plastics or metals, such as stainless steel, cobalt chromium, PEEK, one or more nylons, polyimide, or the like, and/or may at least partially be formed from magnetic materials, as described herein.

Figure 4C:
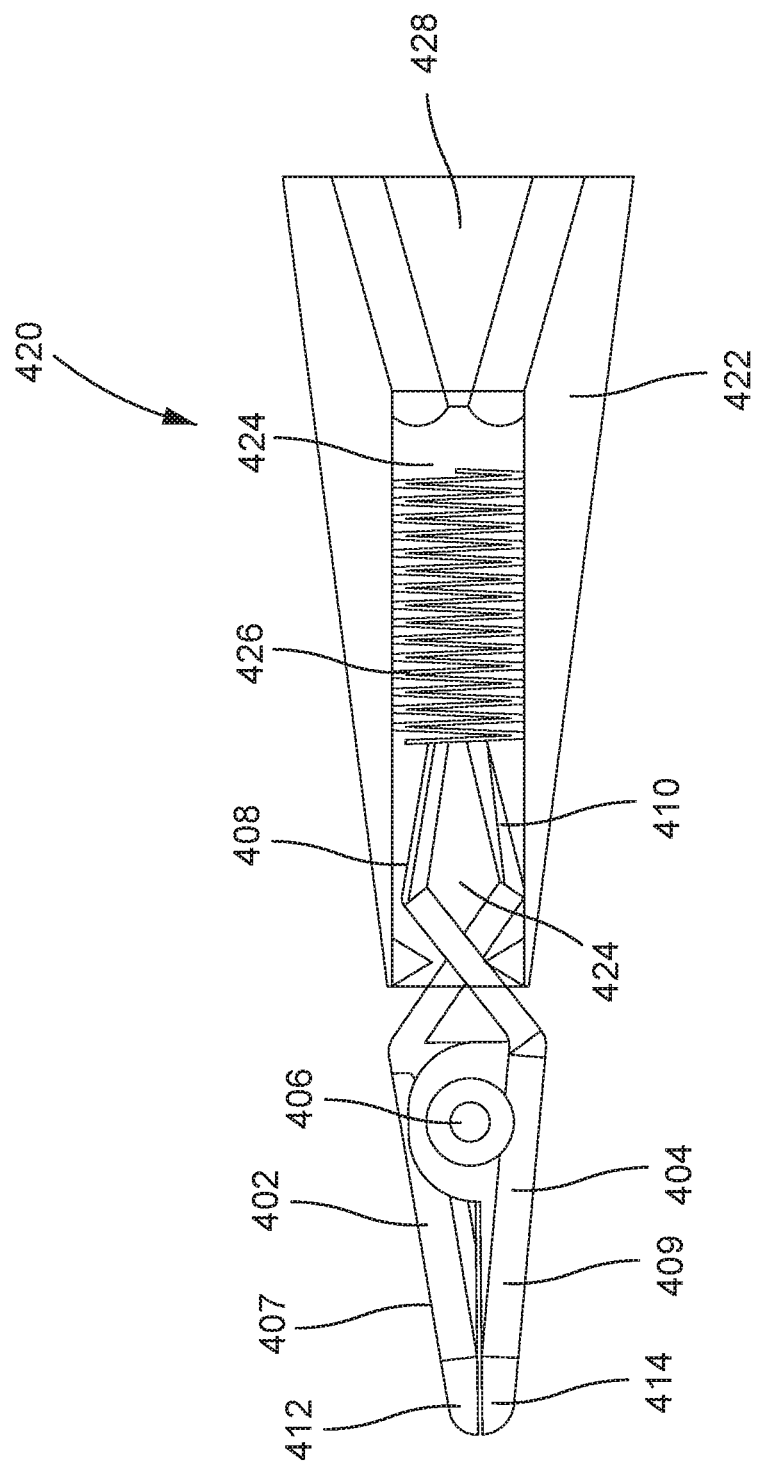
FIG. 4C depicts a side view of the graspers of the system of FIGS. 4A-4B.

FIG. 4C shows an enlarged side view of the clip 400. As shown there, the clip 400 may comprise a first arm 402 and a second arm 404 attached at pivot joint 406. The first and second arms 402 and 404 may have proximal portions 408 and 410, respectively, and distal portions 412 and 414, respectively, which may be configured to cross across pivot joint 406 such that rotation of the proximal portions 408 and 410 away from each other may correspond with rotation of the distal portions 412 and 414 away from each other, and similarly, rotation of the proximal portions 408 and 410 toward each other may correspond with rotation of the distal portions 412 and 414 toward each other. The clip 400 may be actuated between closed and open configurations to releasably connect the clip 400 to tissue or release the clip 400 from tissue, respectively. In the open configuration, the distal portions 412 and 414 of the first and second arms 402 and 404 may be rotationally positioned away from each other to define a space between the distal portions 412 and 414 of the first and second arms 402 and 404, such as shown in FIG. 4B. Similarly, when the clip 400 is in a closed configuration, the distal portions 412 and 414 of the first and second arms 402 and 404 may be rotationally biased toward each other to reduce or eliminate space between the distal portions 412 and 414 of the first and second arms 402 and 404. While the distal portions 412 and 414 of the first and second arms 402 and 404 are shown in FIGS. 4A and 4C as contacting each other, it should be appreciated that when clip 400 is connected to tissue, tissue positioned between the first and second arms 402 and 404 may prevent the distal portion 412 of the first arm 402 from contacting the distal portion 414 of the second arm 404 when the clip 400 is placed in the closed configuration. In some variations, the distal portions 412 and 414 of first and second arms 402 and 404 may be rotationally biased toward each other. For example, in some variations the clip 400 may comprise a spring, such as a torsional spring, which may spring-bias the distal portions 412 and 414 of the first and second arms 402 and 404 toward each other, which may in turn bias the clip 400 into a closed position. The bias toward the closed configuration may act to hold tissue positioned between the distal portions 412 and 414 of the first and second arms 402 and 404.

The distal portions 412 and 414 of the first and second arms 402 and 404, respectively, may comprise one or more features that may promote engagement with tissue, but need not. In some variations, the inner surfaces 416 and/or 418 of the distal portions 412 and 414, respectively, may be roughened or texturized, which may help to reduce slipping between the arms and tissue. Additionally or alternatively, the inner surfaces 416 and/or 418 may comprise teeth or ridges, or other projections that may facilitate engagement of the first and second arms 402 and 404 with tissue. In some variations of the clip described here, the clip may comprise one or more coatings that may help to smooth discontinuities in the contours of the clip and may act to provide one or more atraumatic surfaces of the clip. The one or more coatings may comprise silicone, urethane, one or more nylon blends, polyethylenes, fluoropolymers, combinations thereof, and the like.

Generally, at least a portion of the clip 400 described here may be formed from one or more materials which may be attracted to a magnetic field, as described in more detail herein, but need not be. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. In variations in which the materials include steel alloys, the steel alloys may be in a martensitic state. In some variations, coldworking may be used to improve the magnetic permeability of the clip 400, for instance during the machining process. Having at least a portion of the clip 400 formed from one or more metallic or magnetic materials that may be attracted to a magnetic field may allow the clip 400 to be manipulated by a magnetic control assembly, as will be discussed in more detail herein. In some variations, the proximal ends of the clip 400 may comprise magnetic or ferromagnetic materials to facilitate engagement by the delivery device (as described in more detail herein), but need not. In some variations, the at least a portion of the clip 400 formed from one or more materials which may be attracted to a magnetic field may be part of the coupling element 420 described herein; in other variations, this magnetic portion may be distinct from the coupling element 420.

As mentioned above, the clip 400 may further comprise a coupling element 420. The coupling element 420 may facilitate engagement of the clip 400 to a delivery device (such as the delivery device 450), and may further facilitate actuation of the clip 400 between open and closed configurations, as described in detail herein. As shown in FIGS. 4A-4C, the coupling element 420 may be configured to facilitate temporary coupling between the clip 400 and a delivery device. Generally, the coupling element 420 may comprise a body 422 and a bore 424 extending therethrough. In the variation shown in FIGS. 4A-4C, the body 422 may be shaped as a tapered cylinder, although it should be appreciated that the body may have any suitable shape (e.g., a cylinder, a box shape, or the like). Additionally, while the bore 424 is shown in FIGS. 4A-4C extending along a central axis of the body 422, it should be appreciated that in some variations the bore may be offset from the central axis of the body 422.

Generally, the bore may be configured to house the proximal ends 408 and 410 of the lever arms 402 and 404 to couple the coupling element 420 to the arms. The bore 424 may be sized to accommodate the proximal ends 408 and 410 of the lever arms 402 and 404, and a distal portion of the bore 424 may be sized such that remainder of the clip (i.e., the first and second lever arms 402 and 404) may be prevented from disengaging the coupling element 420 during use of the clip 400. Additionally, in some variations the bore may comprise a threaded portion 426, which may engage a portion of a delivery device, as will be described in more detail herein. Additionally or alternatively, the bore 424 may comprise a funnel portion 428 at a proximal end of the bore 424, such that the diameter of the bore 424 may increase from a distal end of a funnel portion 428 to a proximal end of the funnel portion 428. The larger diameter at the proximal end of the funnel portion may provide a larger entrance to receive a portion of a delivery device, and the decreasing diameter towards the distal end of the funnel portion may guide the received portion of the delivery device toward the remainder of the bore 424. In some variations, at least a portion of the funnel portion 428 may have a non-circular cross-section, which may facilitate actuation of the clip 400, as will be discussed in more detail herein.

As mentioned above, the coupling element 420 may be configured to facilitate temporary coupling between the clip 400 and a delivery device. For example, FIGS. 4A and 4B depict variations of a delivery device 450, which may be configured to couple to and actuate the clip 400. As shown there, the delivery device 450 shown in FIGS. 4A-4B may comprise an outer sheath 458 and an actuation rod 452 positioned at least partially within and slidable relative to the outer sheath 458. As shown there, the actuation rod 452 may comprise a threaded section 456, which may engage the threaded portion 426 of the bore. To do so, the actuation rod 452 may be advanced into the bore 424 of the coupling element 420. In some variations, the actuation rod 452 may have a tapered distal end 454, which may allow the actuation rod to more easily enter the bore. This may provide particular utility in instances where the actuation rod 452 is introduced to the bore 424 when the clip 400 is positioned within the body. Similarly, when the bore 424 comprises a funnel portion 428, the funnel portion 428 may help to guide the actuation rod 452 into the bore 424.

When the threaded portion 456 of the actuation rod 452 reaches the threaded portion 426 of the bore 424, the actuation rod 452 may be rotated relative to the coupling element 420 to screw the threaded portion 456 of the actuation rod into the threaded portion 426 of the bore 424 to engage the actuation rod 452 and the bore 424. When the threaded portions 426 and 456 of the bore 424 and the actuation rod 452, respectively, are engaged, rotation of the actuation rod 452 in a first direction relative to the coupling element 420 may advance the actuation rod 452 along the bore 424. Conversely, rotation of the actuation rod 452 in an opposite direction relative to the coupling element 420 may retract the actuation rod 452 relative to the bore 424.

When the actuation rod 452 engages the coupling element 424 as discussed herein, it may be desirable to hold or otherwise constrain the coupling element 424 such that rotation of the actuation rod 452 does not cause the clip 400 to rotate with the actuation rod 452. If the clip 400 is free to rotate with the actuation rod 452, the actuation rod 452 may not rotate relative to the clip 400, and thus may not be able to advance or withdraw relative to the clip 400. Accordingly, in some variations, the outer sheath 458 may comprise one or more projections 460 extending from a distal end of the outer sheath 458. The one or more projections 460 may be configured to engage a portion of the coupling element 420, such that the engagement between the one or more projections 460 and the coupling element 420 prevents rotation between the outer sheath 458 and the coupling element 420. For example, in variations where a portion of the bore 424 of the coupling element 420 comprises a non-circular cross-sectional shape (e.g., a square-shaped portion of a funnel portion 428), the outer sheath 458 may comprise a projection 460 having a corresponding shape (e.g., a square-shaped projection) that is configured to fit within the bore 424 and prevent rotation between the bore 424 and the projection 460. In these instances, the outer sheath may be advanced such that the projection 460 engages the coupling element 420. Since this engagement may prevent rotation between the outer sheath 458 and the clip 400, rotation of the actuation rod 452 relative to the outer sheath 458 may also result in rotation of the actuation rod 452 relative to the clip 400, which may cause threading between the actuation rod and the bore, as discussed herein.

The delivery device 450 may also be configured to actuate the clip 400. As mentioned above, rotation of the actuation rod 452 relative to the clip 400 may advance the actuation rod 452 through the bore 424 of the coupling element 420. As the actuation rod 452 is advanced, the tapered distal end 454 of the actuation rod 452 may be selectively advanced between the distal portions 408 and 410 of the first and second lever arms 402 and 404. Further advancement of the actuation rod 452 may rotate the proximal ends 407 and 409 of the first and second arms 402 and 404 away from each other, which may move the clip 400 into an open configuration, as shown in FIG. 4B and discussed herein. Conversely, when the actuation rod 452 is selectively retracted proximally relative to the clip 400 by rotation in the opposite direction relative to the threaded portion 426 of bore 424, the first and second lever arms 402 and 404 may rotate to return to a closed configuration, as shown in FIGS. 4A and 4C, allowing the clip 400 to be releasably connected to tissue. The actuation rod 452 may be rotated directly by the user, or the rotation may be actuated by any suitable mechanism, such as one controlled by the user at a remote proximal location via a handle or other interface. Once the clip 400 holds tissue between the first arm 402 and the second arm 404, the clip 400 may be controlled by the magnetic control assembly to manipulate the attached tissue. The delivery device 450 may be disengaged from the clip 400 and removed from the anatomical cavity. If desirable, the delivery device 450 may subsequently reengage the clip 400 to disconnect the clip 400 from the tissue and/or reposition the clip 400.

Figure 11A:
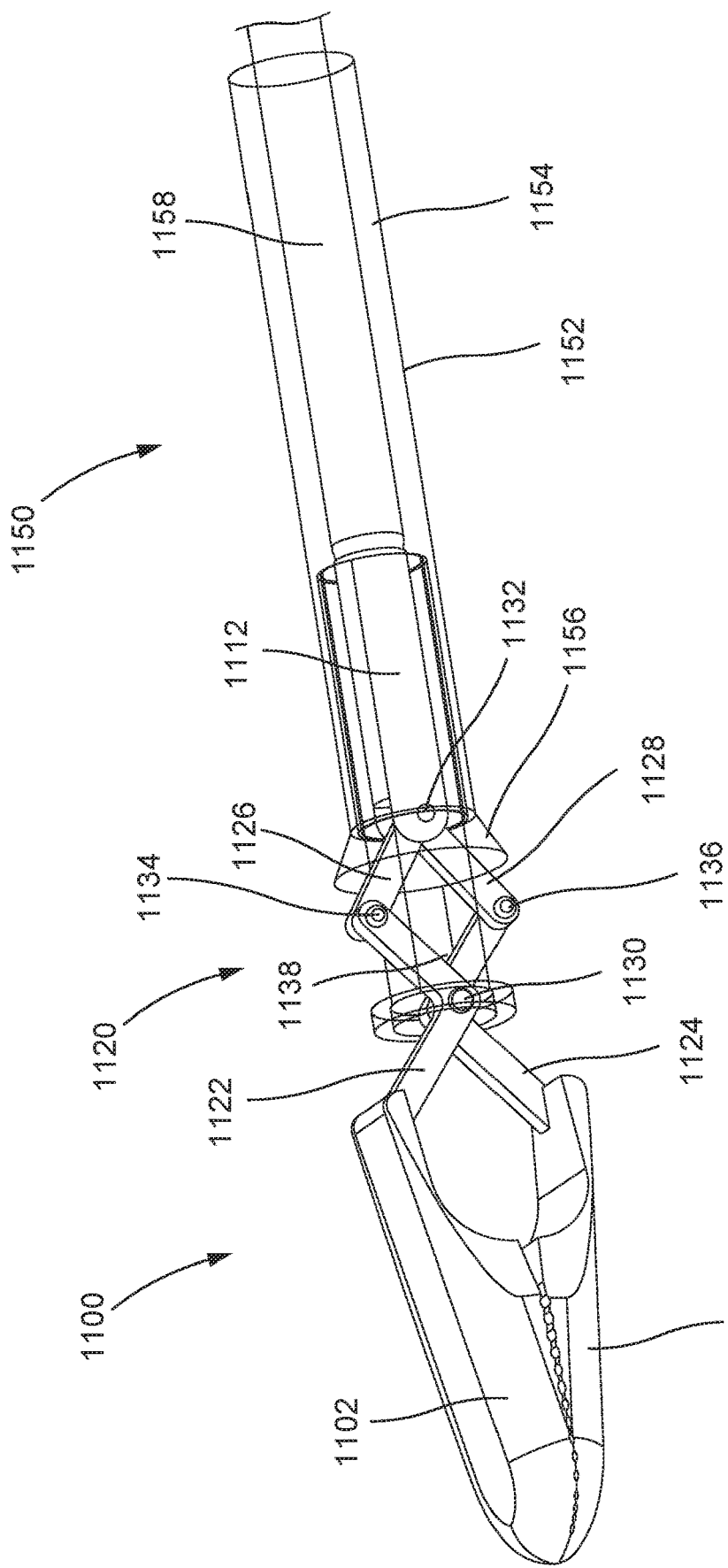
FIGS. 11A-11B depict perspective views of a variation of the systems described here.
Figure 11B:
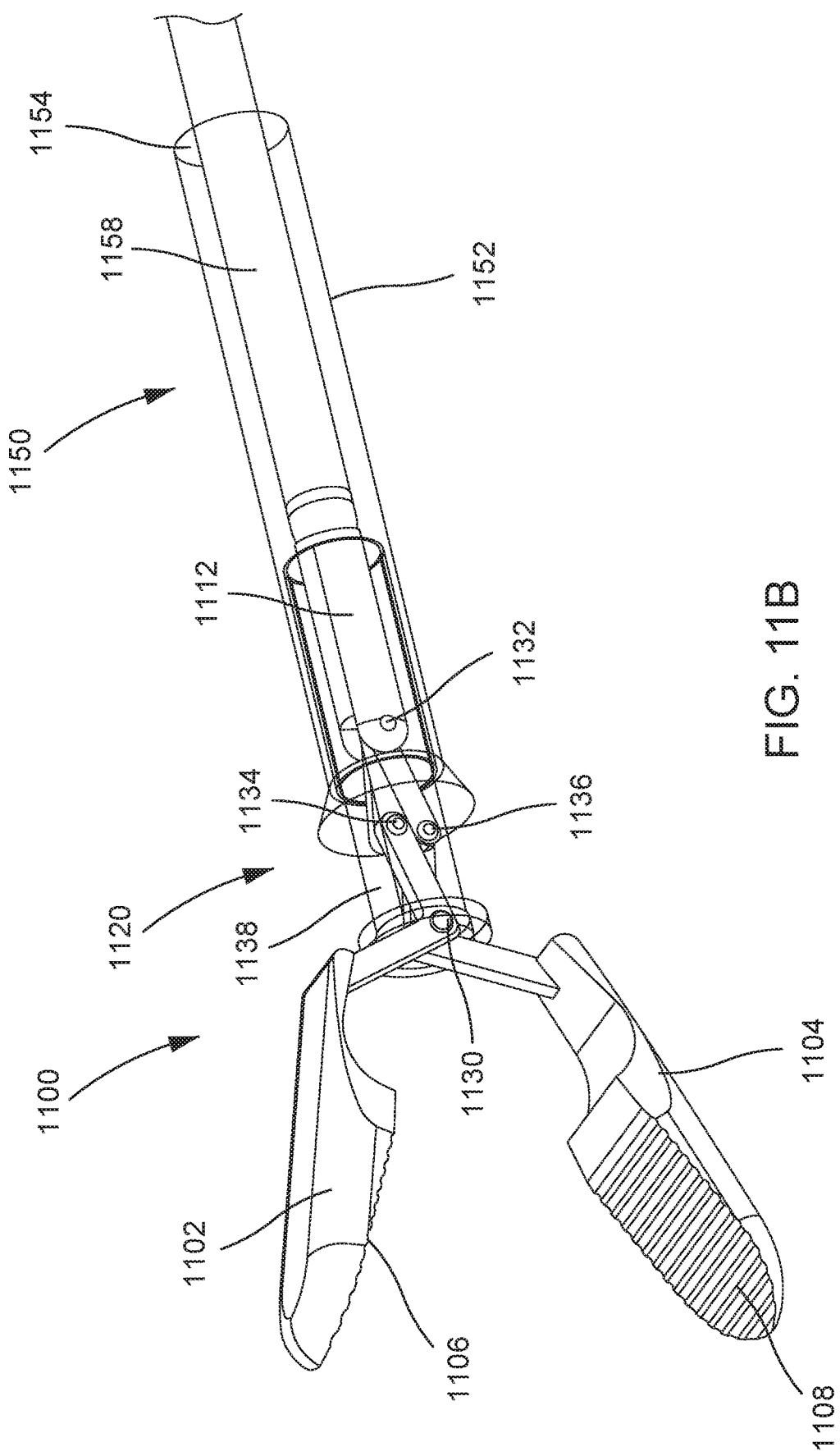
Figure 12A:
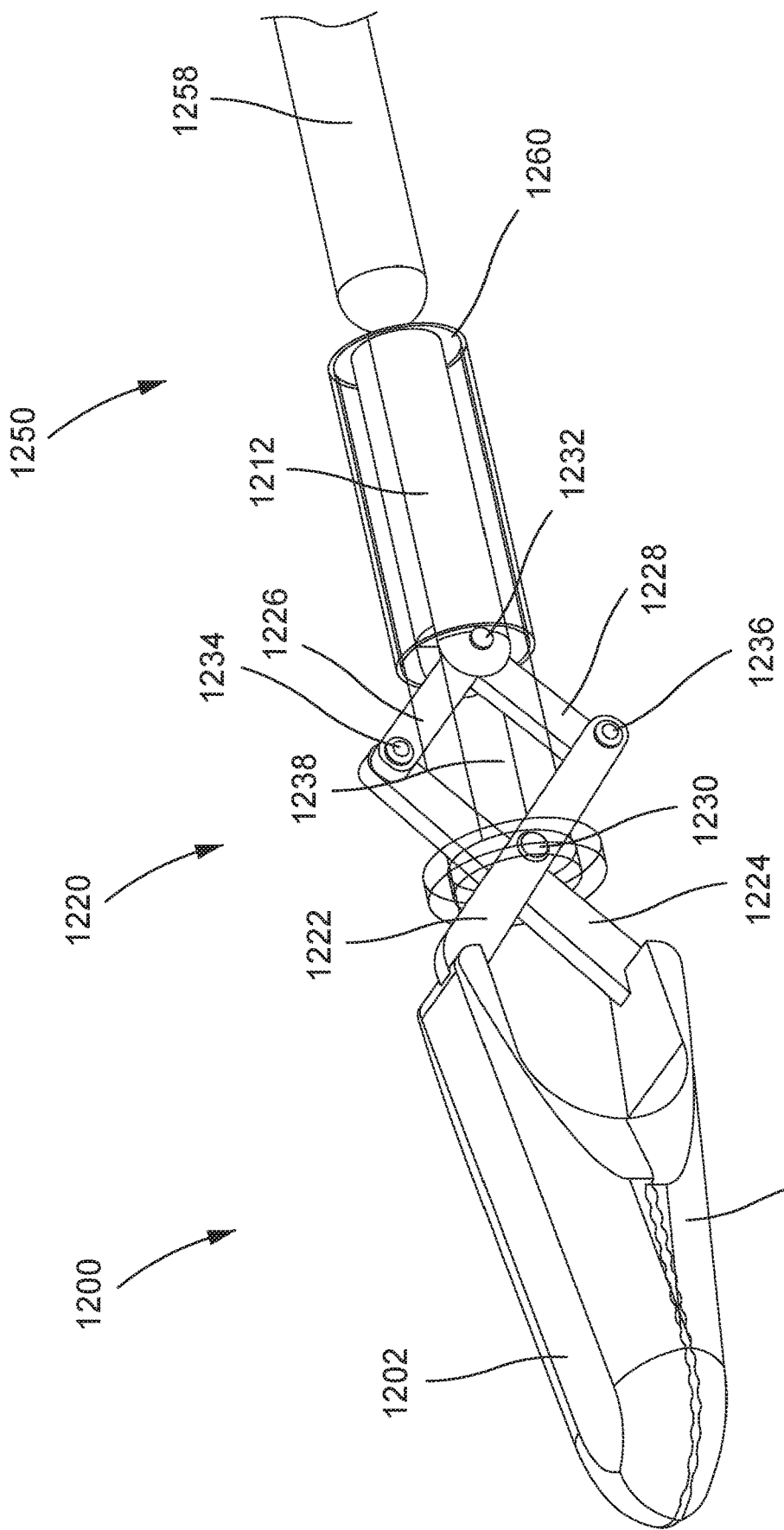
FIGS. 12A-12B depict perspective views of a variation of the systems described here.
Figure 12B:
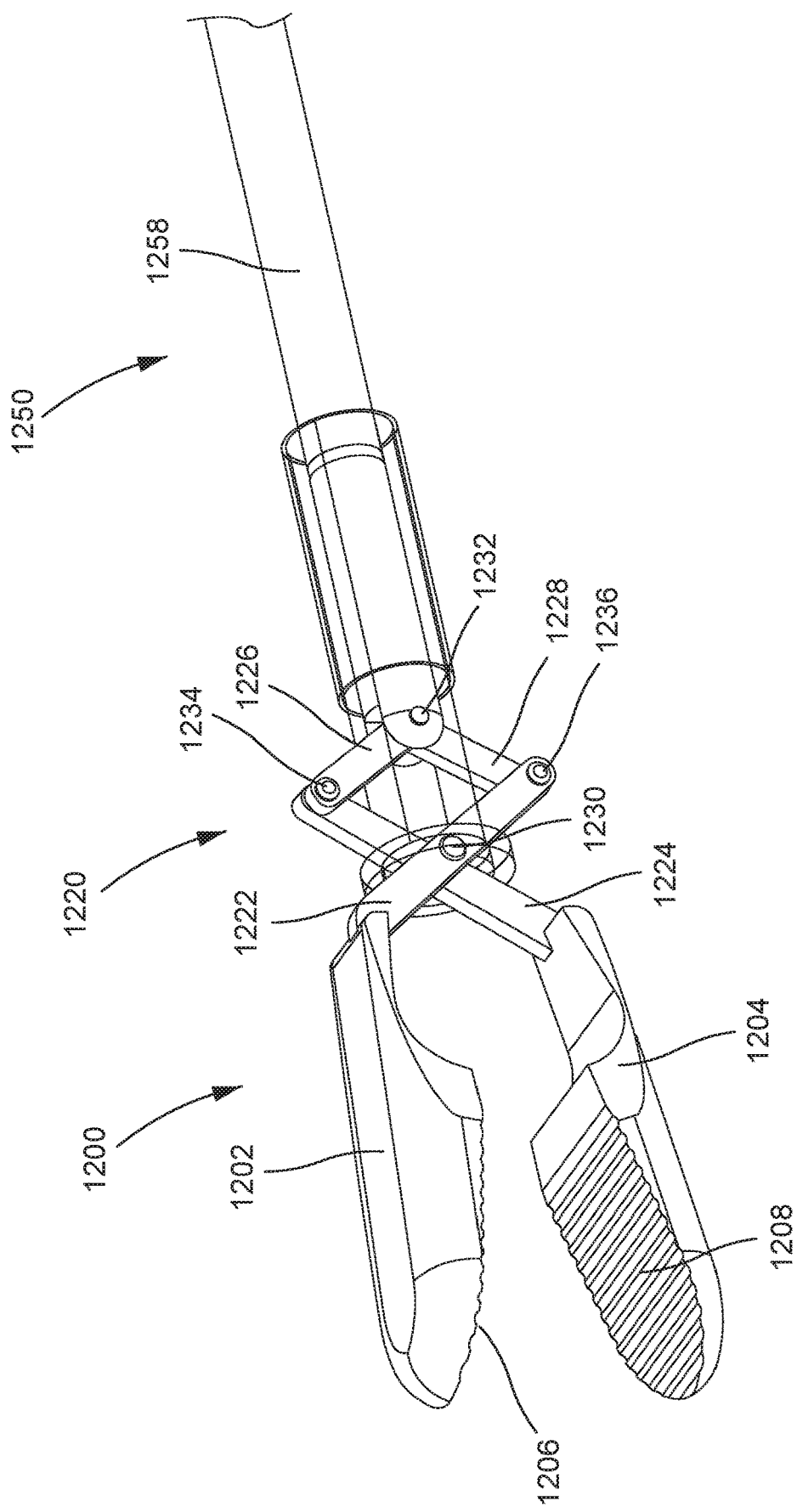

FIGS. 1A-11B and 12A-12B depict other variations of systems as described here in which the grasper comprises a clip. Specifically, FIGS. 11A-11B show perspective views of a system comprising a clip 1100 and a delivery device 1150, and FIGS. 12A-12B show perspective views of a system comprising a clip 1200 and a delivery device 1250. The clips 1100, 1200 may be releasably coupled to the delivery devices 1150, 1250 (as shown in FIGS. 11A-11B and 12A-12B), and the clips 1100, 1200 may be actuated between closed (FIGS. 11A and 12A) and open (FIGS. 11B and 12B) configurations by the delivery devices 1150, 1250 or by a separate device, as described in more detail herein.

As in the other variations discussed herein, the delivery devices 1150, 1250 and the clips 1100, 1200 may be configured for laparoscopic introduction into the body. In these variations, the clips 1100, 1200 may be sized such that they may be advanced through a laparoscopic port. In some instances, the clips 1100, 1200 may be sized such that they may fit through a laparoscopic port when the clips 1100, 1200 are in an open configuration, closed configuration, or either the open or closed configurations. In some of these variations, the largest width of the clips 1100, 1200 in a closed configuration may be less than or equal to about 10 mm, so that the clips 1100, 1200 may be advanced through a 10 mm laparoscopic port when the clips are in a closed configuration. Similarly, distal portions of the delivery devices 1150, 1250 may also be sized such that they may fit through a laparoscopic port. In some variations, the delivery devices 1150, 1250 may be configured such that the distal portions of the delivery devices 1150, 1250 may have diameters less than or equal to about 10 mm. The clips 1100, 1200 and delivery devices 1150, 1250 may be formed from any suitable materials, such as one or more of medical grade, high-strength plastics or metals, such as stainless steel, cobalt chromium, PEEK, one or more nylons, polyimide, or the like, and/or may at least partially be formed from magnetic materials, as described herein.

As shown in FIGS. 11A-11B and 12A-12B, the clips 1100, 1200 may comprise linkage assemblies 1120, 1220. Each linkage assembly may comprise a series of struts connected by pivot joints, such that force applied to one or more struts may cause the clip to move between the open and closed configurations. In some variations, such as the one shown in FIGS. 11A-11B, collapsing the linkage assembly (i.e., moving the struts toward each other by rotating them about the pivot joints) may cause the clip 1100 to move from a closed configuration to an open configuration, while expanding the linkage assembly (i.e., moving the struts away from each other by rotating them about the pivot joints) may cause the clip 1100 to move from an open configuration to a closed configuration. In other variations, such as the one shown in FIGS. 12A-12B, collapsing the linkage assembly (i.e., moving the struts toward each other by rotating them about the pivot joints) may cause the clip to move from an open configuration to a closed configuration. Conversely, expanding the linkage assembly (i.e., moving the struts away from each other by rotating them about the pivot joints) may cause the clip to move from a closed configuration to an open configuration.

It should be appreciated that force need not be applied to all struts in the linkage assembly in order to move the clip between the open and closed configurations; rather, force applied to a subset of the struts (e.g., one or two struts, such as two opposing struts, or at one or two pivot joints, such as two opposing pivot joints) may cause the clip to move between the open and closed configuration. While the linkage assemblies 1120, 1220 shown in FIGS. 11A-11B and 12A-12B have four struts connected by two central pivot joints and two end pivot joints, it should be appreciated that in other variations, the linkage assembly may comprise fewer or more struts and/or pivot joints. Furthermore the struts may be straight (as shown in FIGS. 12A-12B), bent, or a combination thereof (as shown in FIGS. 11A-11B, where struts 1122 and 1124 are bent and struts 1126 and 1128 are straight). It should also be appreciated that while the linkage assemblies 1120, 1220 are described herein as comprising struts and pivot joints, in other variations the linkage assembly may comprise other elements, such as struts comprising living hinges. In some variations, living hinges may limit the clip's lifetime, thereby encouraging replacement after a certain period or amount of use.

The clip 1100 may comprise a first arm 1102 and a second arm 1104 attached via struts 1122 and 1124. As shown in FIGS. 11A-11B, the struts 1122 and 1124 may have distal ends fixedly attached to the proximal ends of first and second arms 1102 and 1104, respectively. Struts 1122 and 1124 may be connected at a pivot joint 1130 and may have a bent shape, such that if the portions of the struts 1122 and 1124 proximal to the pivot joint 1130 are rotated toward each other, the portions of the struts 1122 and 1124 distal to the pivot joint 1130 may rotate away from each other, which in turn may move first and second arms 1102 and 1104 away from each other into an open configuration, as shown in FIG. 11B. Conversely, if the portions of the struts 1122 and 1124 proximal to the pivot joint 1130 are rotated away from each other, the portions of the struts 1122 and 1124 distal to the pivot joint 1130 may be rotated toward each other, which in turn may move first and second arms 1102 and 1104 toward each other into a closed configuration, as shown in FIG. 11A. The proximal ends of the struts 1122 and 1124 may be rotatably attached to struts 1126 and 1128, respectively, via pivot joints 1134 and 1136. The proximal ends of struts 1126 and 1128, in turn, may be rotatably connected via another pivot joint 1132.

Similarly, the clip 1200 may comprise a first arm 1202 and a second arm 1204 attached via struts 1222 and 1224. As shown in FIGS. 12A-12B, the struts 1222 and 1224 may have distal ends fixedly attached to the proximal ends of the first and second arms 1022 and 1024, respectively. Struts 1222 and 1224 may have a straight shape and may be connected at a middle pivot joint 1230, such that if the portions of the struts 1222 and 1224 proximal to the pivot joint 1230 are rotated away from each other, the portions of the struts 1222 and 1224 distal to the pivot joint 1230 may also rotate away from each other, which in turn may move the first and second arms 1202 and 1204 away from each other into an open configuration, as shown in FIG. 12B. Conversely, if the portions of the struts 1222 and 1224 proximal to the pivot joint 1230 are rotated toward each other, the portions of the struts 1222 and 1224 distal to the pivot joint 1230 may also be rotated toward each other, which in turn may move the first and second arms 1202 and 1204 toward each other into a closed configuration, as shown in FIG. 12A. The proximal ends of the struts 1222 and 1224 may be rotatably attached to struts 1226 and 1228, respectively, via pivot joints 1234 and 1236. The proximal ends of struts 1226 and 1228, in turn, may be rotatably connected via another pivot joint 1232.

As mentioned above, it should be appreciated that the clips 1100, 1200 may comprise other configurations than those described above. For example, the linkage assembly may have more or fewer struts and/or pivot joints, other types of joints, other strut shapes, or the like. Similarly, the clip may have other designs, such as the other grasper designs described herein. In some variations, for example, the first arm and second arm may be directly rotatably connected, such as via a pivot joint at their proximal ends, or via a pivot joint located at points on the first and second arms between their ends, so that if distal portions of the first and second arms rotate away from each other, proximal portions of the first and second arms rotate toward each other.

In some variations, clips 1100, 1200 may comprise protective sheaths 1138, 1238 located over at least a portion of the linkage assemblies 1120, 1220 and/or at least a portion of the coupling elements 1112, 1222, described in more detail herein. In these variations, the protective sheaths 1138, 1238 may comprise windows through which portions of the linkage assemblies 1120, 1220 may extend when the linkage assemblies 1120, 1220 are in an expanded configuration.

The clips 1100, 1200 may be actuated between closed and open configurations to releasably connect the clip to tissue or release the clip from tissue, respectively. In the open configuration, the first and second arms 1102 and 1104 of clip 1100, or first and second arms 1202 and 1204 of clip 1200, may be positioned away from each other to define a space between the arms, as shown in FIGS. 11B and 12B. Conversely, when the clips 1100, 1200 are in a closed configuration, the distal portion of the arms 1102 and 1104 of clip 1100, or distal portion of the arms 1202 and 1204 of clip 1200, may be near each other to reduce or eliminate space between the distal portions of the arms. While the distal portions of the arms are shown in FIGS. 11A and 12A as contacting each other, it should be appreciated that when clip is connected to tissue, tissue positioned between the first and second arms may prevent the distal portions of the arms from contacting each other when the clip is in the closed configuration.

In some variations, the clips 1100, 1200 may be biased toward a closed configuration by one or more biasing elements, which may act on the struts and/or pivot joints to rotationally bias the first and second arms toward each other. In other variations, the clip may be biased toward an open configuration by one or more biasing elements, which may act on the struts and/or pivot joints to rotationally bias the first and second arms away from each other. In some variations, the biasing elements may comprise springs, such as torsional, extension, and/or compression springs. For example, the clip 1100 may comprise a torsional spring at pivot joint 1130 that spring-biases the clip 1100 toward a closed configuration. As another example, the clip 1100 may comprise one or more compression springs proximal to pivot joint 1130 and/or one or more extension springs distal to pivot joint 1130 configured to collapse the linkage assembly, which may spring-bias the clip 1100 toward a closed configuration. When the clip 1100 is biased toward a closed configuration, this bias may act to hold tissue positioned between the distal portions of the arms 1102 and 1104.

In some variations, the one or more springs or other biasing elements, and/or the relative lengths of the struts, may be tailored to the desired force required to move the clip between open and closed configurations and/or the desired force applied by the clip in a closed configuration. For example, the relative lengths of the struts and location of pivot joints may be chosen to provide mechanical advantage to an actuation motion, for example to increase the distance between the arms of the clip for a given actuation force, or to increase the holding force between the arms. Additionally or alternatively, the relative lengths of the struts and/or springs or biasing elements may be tailored such that the amount of forced required to move the clip between open and closed configurations may depend on the strut or struts to which the force is applied.

The distal portions of the first and second arms 1102 and 1104 of clip 1100, or the first and second arms 1202 and 1204 of clip 1200, may comprise one or more features that may promote engagement with tissue, but need not. In some variations, the inner surfaces 1106, 1206 and 1108, 1208 may be roughened or texturized, which may help to reduce slipping between the arms and tissue. Additionally or alternatively, the inner surfaces 1106, 1206 and 1108, 1208 may comprise teeth or ridges, or other projections that may facilitate engagement of the first and second arms 1102, 1202 and 1104, 1204 with tissue. In some variations, the clips 1100, 1200 may comprise one or more coatings that may help to smooth discontinuities in the contours of the clip and may act to provide one or more atraumatic surfaces of the clip. The one or more coatings may comprise silicone, urethane, one or more nylon blends, polyethylenes, fluoropolymers, combinations thereof, and the like.

Generally, at least a portion of the clips 1100, 1200 described here may be formed from one or more materials which may be attracted to a magnetic field, as described in more detail herein, but need not be. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. In variations in which the materials include steel alloys, the steel alloys may be in a martensitic state. In some variations, coldworking may be used to improve the magnetic permeability of the clips 1100, 1200, for instance during the machining process. Having at least a portion of the clips 1100, 1200 formed from one or more metallic or magnetic materials that may be attracted to a magnetic field may allow the clips 1100, 1200 to be manipulated by a magnetic control assembly, as will be discussed in more detail herein. In some variations, the proximal ends of the clips 1100, 1200 may comprise magnetic or ferromagnetic materials to facilitate engagement by the delivery device (as described in more detail herein), but need not be. In some variations, the at least a portion of the clips 1100, 1200 formed from one or more materials that may be attracted to a magnetic field may be part of the coupling elements 1112, 1212 described herein; in other variations, this magnetic portion may be distinct from the coupling elements 1112, 1212.

As mentioned above, the clips 1100, 1200 may further comprise coupling elements 1112, 1212, respectively. The coupling elements 1112, 1212 may facilitate engagement of the clips 1100, 1200 to a delivery device (such as the delivery devices 1150, 1250), and may further facilitate actuation of the clips between open and closed configurations, as described herein. The coupling elements 1112, 1212 may be configured to facilitate temporary coupling between the clips 1100, 1200 and a delivery device. Generally, the linkage assemblies 1120, 1220 may be rotatably attached to the distal end of the coupling elements 1112, 1212, as shown in FIGS. 11A-11B and 12A-12B (as shown there, via pivot joints 1132, 1232). At least a portion of the coupling element may comprise one or more materials that may be attracted to a magnetic field, which may facilitate temporary connection of the clip to a delivery device. The materials may include one or more magnetic or ferromagnetic materials, such as, for example, stainless steel, iron, cobalt, nickel, neodymium iron boron, samarium cobalt, alnico, ceramic ferrite, alloys thereof, and/or combinations thereof.

Turning to the variation of delivery device 1150 shown in FIGS. 11A-11B and delivery device 1250 shown in FIGS. 12A-12B, the delivery device 1150 may comprise an actuation rod 1158, which may releasably engage the coupling element 1112. Delivery device 1250 may similarly comprise an actuation rod 1258, which may releasably engage the coupling element 1212. In some variations, the actuation rods 1158, 1258 may comprise one or more magnetic and/or ferromagnetic materials in at least its distal end, and thus the actuation rods may releasably engage the bodies of the coupling elements via magnetic attractive force when the actuation rods and the bodies are in proximity to each other.

As described above, the clip 1100 may be actuated between closed and open configurations by expanding or collapsing the linkage assembly 1120. In some variations, the delivery device 1150 may be used to expand or collapse the linkage assembly 1120. As shown in FIGS. 11A-11B, the delivery device 1150 may further comprise an outer sheath 1152 having a lumen 1154. The outer sheath 1152 may comprise a distal lip 1156, which may have a tapered or funnel shape, such that the diameter of the lumen 154 at the distal end of the delivery device 1150 decreases from the distal to proximal ends of the lip 1156. At least a portion of the linkage assembly 1120 of the clip 1100 may have an overall diameter when expanded that is less than that of the lumen 1154 of the outer sheath 1152. The clip 1100 may be actuated between closed and open configurations by moving the linkage assembly 1120 into and out of the lumen 1154.

For example, in the variation shown in FIGS. 11A-11B, as the clip 1100 is moved into the lumen 1154, the outer surfaces of a portion of the linkage assembly 1120 (e.g., struts 1126 and 1128) may contact the inner surface of the outer sheath 1152. Further movement of the linkage assembly 1120 may cause it to be compressed (i.e., may cause the struts to be rotatably moved toward each other), due to the constrained diameter of the lumen 1154. As the linkage assembly 1120 is compressed, in the variation shown in FIGS. 11A-11B, the arms 1102 and 1104 may be rotated away from each other, which may move the clip 1100 into an open configuration, as shown in FIG. 1B. Conversely, movement of the clip 1100 out of the lumen 1154 may free the linkage assembly 1120. In variations in which the clip 1100 is biased toward a closed configuration, the bias may then help to return the clip 1100 to a closed position, as shown in FIG. 11A.

The clip 1100 may be moved into and out of the lumen 1154 using any suitable mechanism. In the variation of the delivery device 1150 shown in FIGS. 11A-11B, the clip 1100 may be moved into and out of the lumen by the actuation rod 1158 located slidably within the lumen 1154. When the actuation rod 1158 and the coupling element 1112 are engaged, retracting and advancement of the actuation rode 1158 within the lumen 1154 may move the linkage assembly 1120 into and out of the lumen, which in turn may move the clip 1100 between open and closed configurations. It should be appreciated that in order for the actuation rod 1158 to remain coupled to the clip 1100 during actuation, the engagement force between the coupling element 1112 and the actuation rod 1158 may need to be greater than the longitudinal component of the force required to actuate the clip 1100. In some variations, this force balance may be achieved through selection of biasing elements (e.g., springs), strut lengths in the linkage assembly 1120, and attractive force between the coupling element 1112 and the actuation rod 1158. Once the clip 1100 holds tissue between the first and second arms 1102 and 1104, the clip 1100 may be controlled by the magnetic control assembly to manipulate the attached tissue. The delivery device 1150 may be disengaged from the clip 1100 and removed from the anatomical cavity. If desirable, the delivery device 1150 may subsequently reengage the clip 1150 to disconnect the clip 1150 from the tissue and/or reposition the clip 1150.

Additionally or alternatively, the clip 1100 may be moved between open and closed configurations by a tool separate from the delivery device 1150. For example, a grasping tool (not shown) may be used to apply force to the linkage assembly 1120 (e.g., on two or more opposing struts, or one two or more opposing pivot joints) to move them toward a collapsed configuration. In variations in which the clip 1100 comprises a protective sheath 1138 located over at least a portion of the linkage assembly 1120 and/or at least a portion of the coupling element 1112, force may be applied to the portions of the linkage assembly 1120 extending through windows in the protective sheath 1138.

In the variation shown in FIGS. 12A-12B, the clip 1200 may similarly be actuated between closed and open configurations by expanding or collapsing the linkage assembly 1220. In some variations, the delivery device 1250 may be used to expand or collapse the linkage assembly 1220. As shown in FIGS. 12A-12B, the protective sheath 1238 of the clip 1200 may comprise a lumen 1260 configured to allow the coupling element 1212 and actuation rod 1258 to move proximally and distally relative to the arms 1202 and 1204. When the actuation rod 1258 is moved distally relative to the arms 1202 and 1204, the linkage assembly 1220 may be expanded (i.e., the struts may be rotatably moved away from each other), which may in turn move the clip 1200 into an open configuration, as shown in FIG. 12B. Conversely, when the actuation rod 1258 is moved proximally relative to the arms 1202 and 1204, the linkage assembly 1220 may be compressed (i.e., the struts may be rotatably moved toward each other), which may in turn move the clip 1200 into a closed configuration, as shown in FIG. 12A. It should be appreciated that in order for the actuation rod 1258 to remain coupled to the clip 1200 (as shown in FIG. 12B) during actuation, the engagement force between the coupling element 1212 and the actuation rod 1258 may need to be greater than the longitudinal component of the force required to actuate the clip 1200. In some variations, this force balance may be achieved through selection of biasing elements (e.g., springs), strut lengths in the linkage assembly 1220, and attractive force between coupling element 1212 and actuation rod 1258. Once the clip 1200 holds tissue between the first and second parts 1202 and 1204, the clip 1200 may be controlled by the magnetic control assembly to manipulate the attached tissue. The delivery device 1250 may be disengaged from the clip 1200 (as shown in FIG. 12A) and removed from the anatomical cavity. If desirable, the delivery device 1250 may subsequently reengage the clip 1250 to disconnect the clip 1250 from the tissue and/or reposition the clip 1250.

Figure 5A:
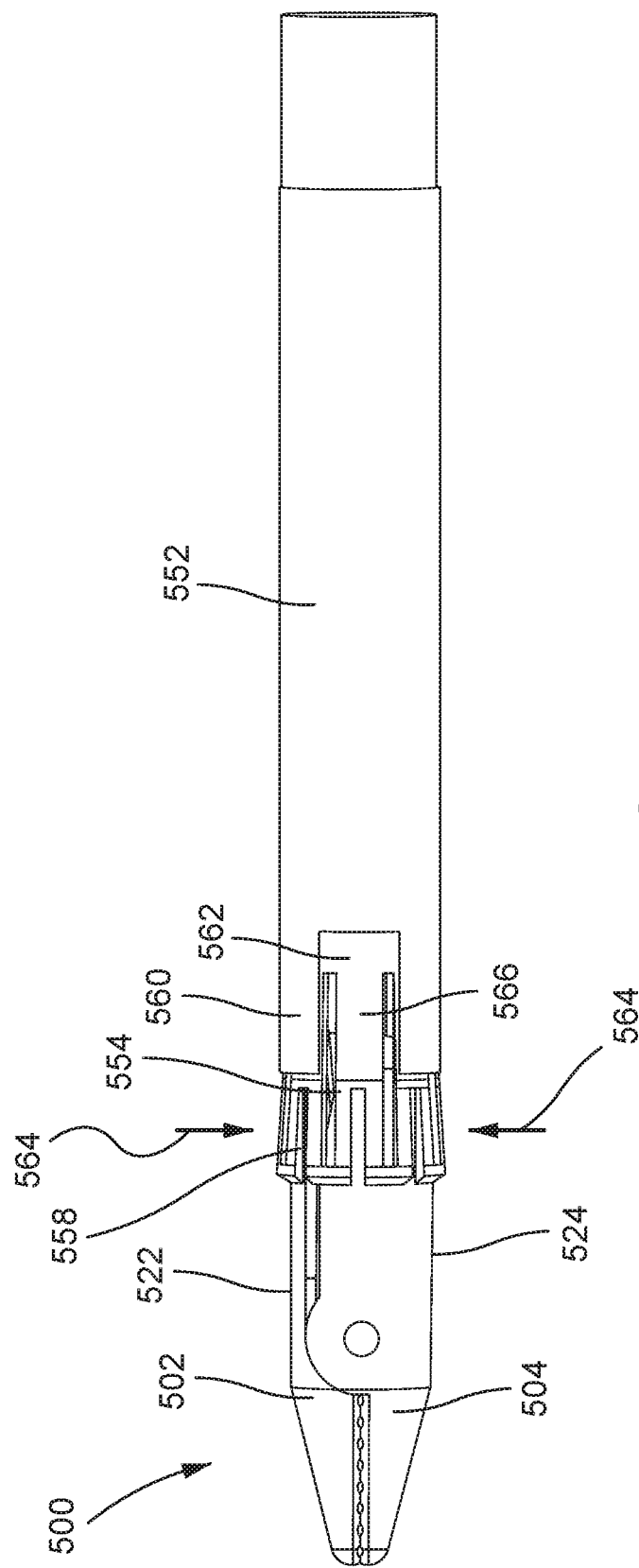
FIG. 5A depicts a side view of a variation of systems described here.
Figure 5C:
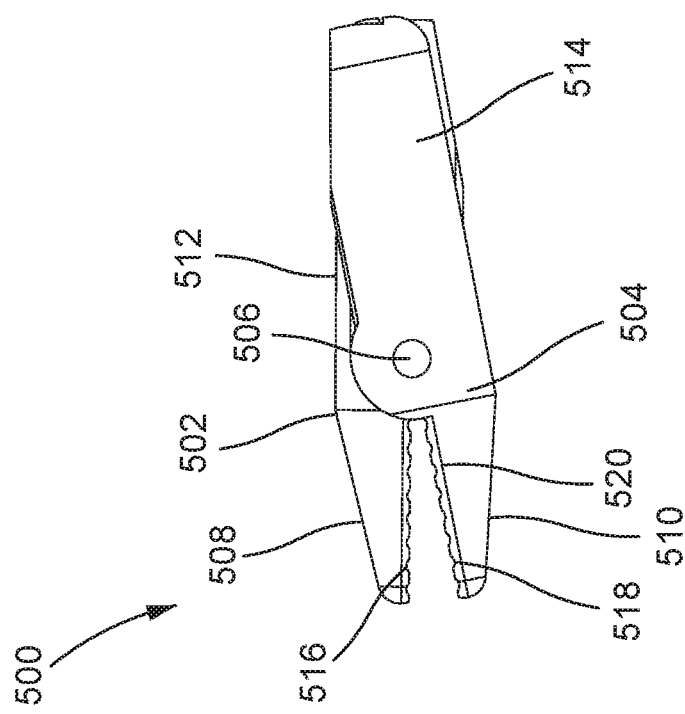
FIGS. 5B-5C depict side views of the graspers of the system of FIG. 5A.
Figure 5B:
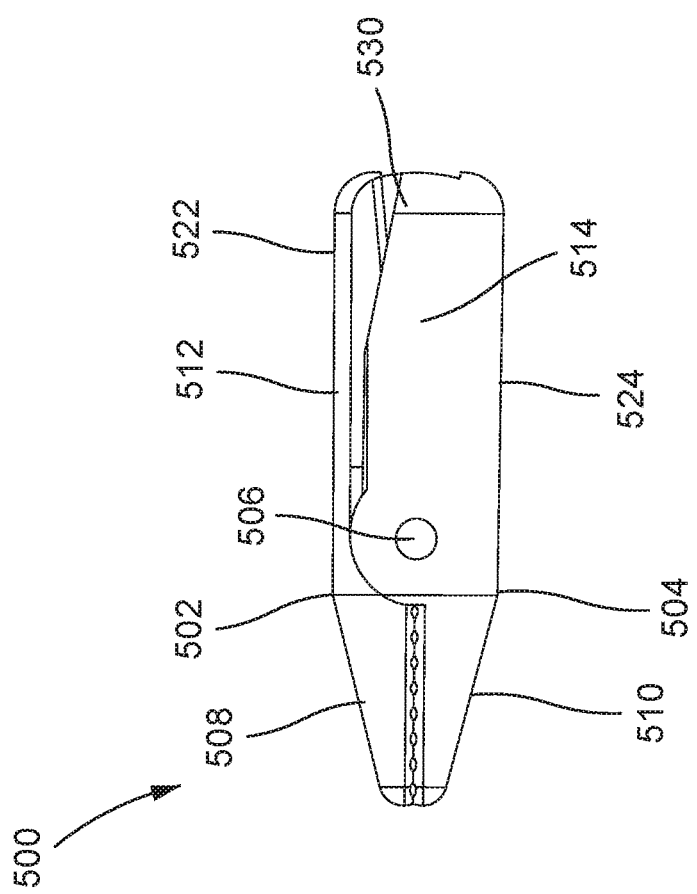
Figure 5E:
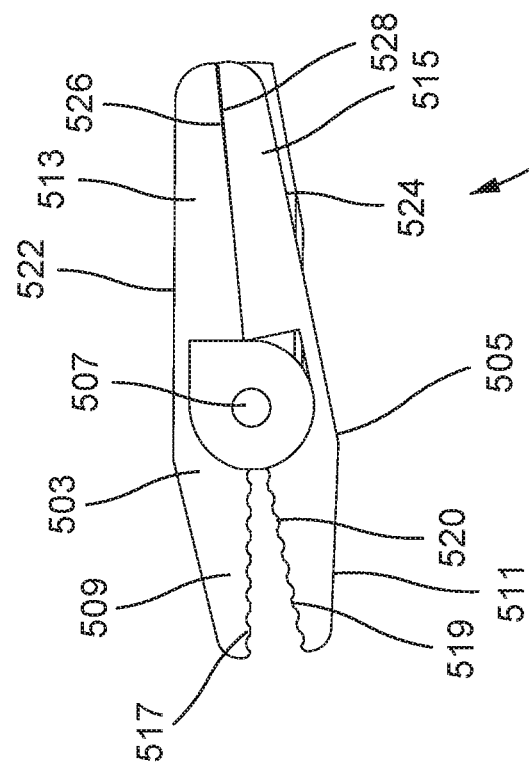
FIGS. 5D-5E depict side views of an additional variation of graspers described here.
Figure 5D:
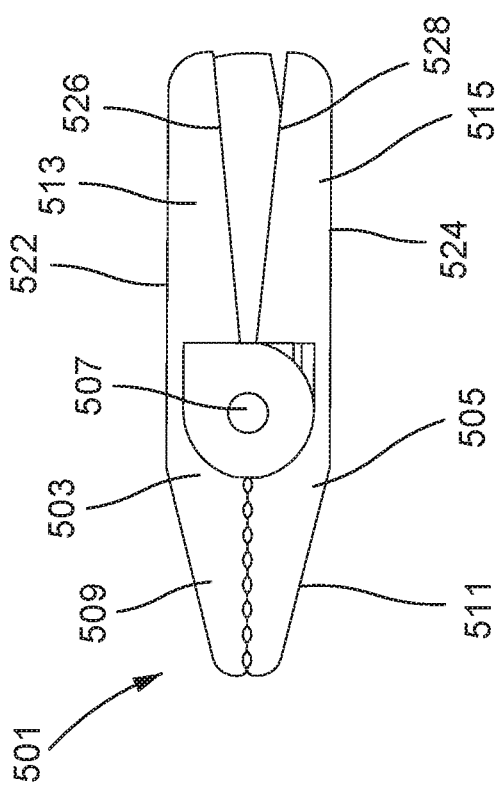

FIG. 5A depicts another variation of a system in which the grasper comprises a clip. Specifically, FIG. 5A shows a side view of a system comprising a clip 500 and an illustrative variation of a delivery device 550 that may be used to actuate the clip 500. FIGS. 5B and 5C show side views of the clip 500, while FIGS. 5D and 5E show cross-sectional side views of the clip 500. The clip 500 may be releasably coupled and decoupled from the delivery device 550. When the clip 500 is coupled to the delivery device 550, the delivery device 550 may actuate the clip 500 to connect the clip 500 to tissue or to detach the clip 500 therefrom.

As in the other variations discussed herein, in some variations depicted in FIGS. 5A-5E, the delivery device 550 and the clip 500 may be configured for laparoscopic introduction into the body. In these variations, the clip 500 may be sized such that it may be advanced through a laparoscopic port. In some of instances, the clip 500 may be sized such that it may fit through a laparoscopic port when the clip 500 is the open configuration and in the closed configuration. In some of these variations, the largest width of the clip 500 may be less than or equal to about 10 mm, so that the clip 500 may be advanced through a 10 mm laparoscopic port. Similarly, a distal portion of the delivery device 550 may also be sized such that it may fit through a laparoscopic port. In some variations, the delivery device 550 may be configured such that the distal portion of the delivery device 550 (e.g., collet 554, as discussed in more detail herein) may have a diameter less than or equal to about 10 mm. The clip 500 and delivery device 550 may be formed from any suitable materials, such as one or more of medical grade, high-strength plastics or metals, such as stainless steel, cobalt chromium, PEEK, one or more nylons, polyimide, or the like, and/or may at least partially be formed from magnetic materials, as described herein.

The clip illustrated in FIGS. 5A-5E may be configured to releasably pinch or grip tissue. As shown in FIGS. 5A-5E, the clip 500 may comprise a first jaw 502 and a second jaw 504, rotatably attached to each other by a pivot joint 506. The first and second jaws 502 and 504 may be rotated relative to each other to actuate the clip 500 between closed and open configurations to releasably connect the clip 500 to tissue or release the clip 500 from tissue, respectively. In the open configuration, the distal portions 508 and 510 of the first and second jaws 502 and 504, respectively, may be rotationally positioned away from each other to define a space between the distal portions 508 and 510 of the first and second jaws 508 and 510, as shown in FIGS. 5C and 5E. Similarly, while the clip 500 is in a closed configuration, the distal portions 508 and 510 of the first and second jaws 502 and 504 may be rotationally biased toward each other to reduce or eliminate space between the distal portions 508 and 510 of the first and second jaws 502 and 504. While the distal portions 508 and 510 of the first and second jaws 502 and 504 are shown in FIGS. 5A, 5B, and 5D as contacting each other, it should be appreciated that when clip 500, tissue positioned between the jaws 502 and 504 may prevent the distal portion 508 of the first jaw 502 from contacting the distal portion 510 of the second jaw 504 when the clip 500 is placed in the closed configuration.

In some variations, the distal ends 508 and 510 of the first jaw 502 and the second jaw 504, respectively, may be rotationally biased toward each other. For example, in some variations the clip 500 may comprise a spring, such as a torsional spring, that may spring-bias the distal ends 508 and 510 of the first and second jaws 502 and 504 toward each other, biasing the clip 500 into a closed position. In other variations, the clip 500 may comprise a spring, such as a compression spring, that may spring-bias the proximal ends 512 and 514 of the first and second jaws 502 and 504, respectively, away from each other, biasing the clip 500 into a closed position. The bias toward the closed configuration may act to hold tissue positioned between the distal portions 508 and 510 of the first and second jaws 502 and 504.

In some variations, the jaws 502 and 504 of the clip 500 may be shaped such that when the clip 500 is in the closed configuration, the proximal portions 512 and 514 of the first jaw 502 and second jaw 504, respectively, define a substantially cylindrical shape, having a substantially constant diameter. This may reduce the overall profile of the clip 500. The distal portions 508 and 510 may also form a tapered cylindrical or conical shape in the closed configuration. The substantially cylindrical shape of the proximal end of clip 500, with rounded, convex surface contours, may also help to make the clip 500 less traumatic to surrounding anatomy.

Additionally, the substantially cylindrical shape of the proximal end of clip 500 may also facilitate actuation of the clip 500 by both the delivery devices described here and standard laparoscopic tools, as described in detail herein. The jaws 502 and 504 of the clip 500 may also have a ramped shape, such that in the closed configuration, the distal portions 512 and 514 of the clip 500 define cylindrical shape, while in the open configuration, the distal portions 512 and 514 of the clip 500 define a tapered cylindrical shape due to the ramp angle of the proximal portions (labeled as 530), such that the bottom surface of the first jaw 502 does not extend past the bottom surface of the second jaw 504, and the top surface of the second jaw 504 does not extend past the top surface of the first jaw 502, when in an open configuration, as shown in FIGS. 5C and 5E. Moreover, the inner portions of jaws 502 and 504 may have ramped surfaces 526 and 528, which are rotationally separated in a closed configuration, which may allow rotation between the jaws 502 and 504. This ramped shaped allows the jaws to rotate about pivot joint 506 into an open configuration, even though the proximal portions of the jaws may define a substantially cylindrical shape in a closed configuration. The ramps may be made of varying angles: larger angles of ramping at edge 526, 528, and 530 allow for greater freedom of rotation of the jaws, and thus greater separation between the first jaw 502 and second jaw 504 in the open configuration, while smaller angles of ramping allow for less freedom of rotation of the jaws, and thus less separation between the first jaw 502 and the second jaw 504.

The distal ends 508 and 510 of the first and second jaws 502 and 504, respectively, may comprise one or more features that may promote engagement with tissue, but need not. In some variations, the inner surfaces 516 and/or 518 of the distal ends 508 and 510, respectively, may be roughened or texturized, which may help to reduce slipping between the jaws and tissue. Additionally or alternatively, the inner surfaces 516 and/or 518 may comprise teeth or ridges 520 (such as shown in FIGS. 5C and 5E) or other projections that may facilitate engagement of the first and second jaws 502 and 504 with tissue. In some variations of the clip described here, the clip may comprise one or more coatings that may help to smooth discontinuities in the contours of the clip and may act to provide one or more atraumatic surfaces of the clip. The one or more coatings may comprise silicone, urethane, one or more nylon blends, polyethylenes, fluoropolymers, combinations thereof, and the like. Additionally or alternatively, the proximal portion of the clip 500 may comprise a coating to increase the ability of a delivery device to engage and actuate the clip 500.

Generally, at least a portion of the clip 500 described here may be formed from one or more materials which may be attracted to a magnetic field, as described in more detail herein, but need not be. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. In variations in which the materials include steel alloys, the steel alloys may be in a martensitic state. In some variations, coldworking may be used to improve the magnetic permeability of the clip 500, for instance during the machining process. Having at least a portion of the clip 500 formed from one or more metallic or magnetic materials that may be attracted to a magnetic field may allow the clip 500 to be manipulated by a magnetic control assembly, as will be discussed in more detail herein. In some variations, the proximal ends and/or protrusions of the clip 500 may comprise magnetic or ferromagnetic materials to facilitate engagement by the delivery device (as described in more detail herein), but need not.

As mentioned above, the delivery device 550 may be releasably coupled and actuate the clip 500 shown in FIGS. 5A-5E. As shown in FIG. 5A, the delivery device 550 may comprise and outer sheath 552 and a collet 554. The collet 554 may be at least partially housed within a lumen of the outer sheath 552, and may be connected to an actuation rod 566. The actuation rod 566 in turn may be slidably disposed within the outer sheath 552 such that advancement and retraction of the actuation rod 566 relative to the outer sheath 552 also advances and retracts, respectively, the collet 554 relative to the outer sheath 552. The collet 554 may have an increased thickness at its distal end 558, and may be configured to fit within the lumen at the distal end 560 of outer sheath 552. Specifically, the actuation rod 566 may move the collet 554 between an advanced position (as shown in FIG. 5A) in which the collet 554 extends from a distal end of the outer sheath 552 and a retracted position in which the collet 554 is withdrawn into the outer sheath. In some variations, the thickness of the collet 554 may increase from a proximal portion of the collet 554 to a distal portion of the collet 554. When the collet 554 is in the advanced position, the collet 554 may radially expand or otherwise be radially expanded such that a lumen of the collet 554 has a first diameter. In some variations, the first diameter may be large enough to accommodate the clip 500 when the clip is in the closed configuration. As the collet 554 is retracted into the outer sheath 552, the outer sheath 552 may constrain the outer diameter of the collet (e.g., providing a radially-inward force to collet 554 to allow the collet to fit inside the outer sheath 552). As the outer diameter of the collet 554 is limited by the outer sheath 552, the increasing thickness of the collet 554 may reduce the diameter of the lumen of the collet 554. For example, the lumen of the collet may be reduced to a second diameter that is smaller than the first diameter. In some instances, this second diameter may be sufficiently small to actuate the clip 500 from a closed to an open configuration, as discussed in more detail herein. In some variations, the distal end 560 of the outer sheath 552 may have two slots 562 on opposing sides on the distal end 560 of outer sheath 552. In these variations, as the collet 554 is moved to the retracted position, the outer sheath 552 may constrain the collet 554 in a first direction (as indicated by arrows 564), but not in a second direction (e.g., in a direction perpendicular to the page). This may allow the collet 554 to apply a force to the clip 500 in a first direction without needing to apply a force to the clip 500 in a second direction.

As mentioned above, the collet 554 may be configured to receive a proximal portion of the clip 500 when the collet 554 is in an advanced position, as shown in FIG. 5A. In some variations, the first diameter mentioned above may be slightly smaller than an outer diameter of the proximal portion of the clip 500, such that the collet 554 is slightly expanded by the clip 500. In these variations, the collet 554 may apply inward normal force to the clip that is sufficient to temporarily hold the clip 500, but that does not move the jaws 502 and 504 into an open configuration. When the collet 554 is moved to a retracted position (e.g., when the outer sheath 552 is advanced relative to the collet 554), the reduction of diameter of the lumen of the collet 554 may apply inward force on the proximal ends 512 and 514 of jaws 502 and 504, respectively. This may cause the proximal ends 512 and 514 to move toward each other, and in turn cause the distal portions 508 and 510 to move away from each other and into an open configuration, as shown in FIGS. 5C and 5E. In variations where the outer sheath 552 includes slots 562, the clip 500 may be aligned with the slots 562 of the outer sheath 552 such that the plane of rotation of the jaws is parallel to the first direction 552, which may allow the force provided in the first direction 552 by the collet 554 to actuate the clip 500.

Conversely, when the outer sheath 552 is retracted proximally relative to the collet 554, the clip may return to a closed configuration (e.g., by virtue of a spring bias toward the closed configuration), as the constraining force provided by the outer sheath may be removed as the shaft is retracted. When tissue is positioned between the distal portions of the jaws, moving the clip 500 to the closed configuration may cause the clip 500 to releasably connect to the tissue. Once the clip 500 holds tissue between the first jaw 502 and the second jaw 504, the location of the clip 500 may be controlled by a magnetic control assembly to manipulate the attached tissue. The delivery device 550 may then be disengaged from the clip 500 and removed from the anatomical cavity. If desirable, the delivery device 550 may subsequently reengage the clip 500 to disconnect the clip 500 from the tissue and/or to reposition the clip 500.

Figure 6A:
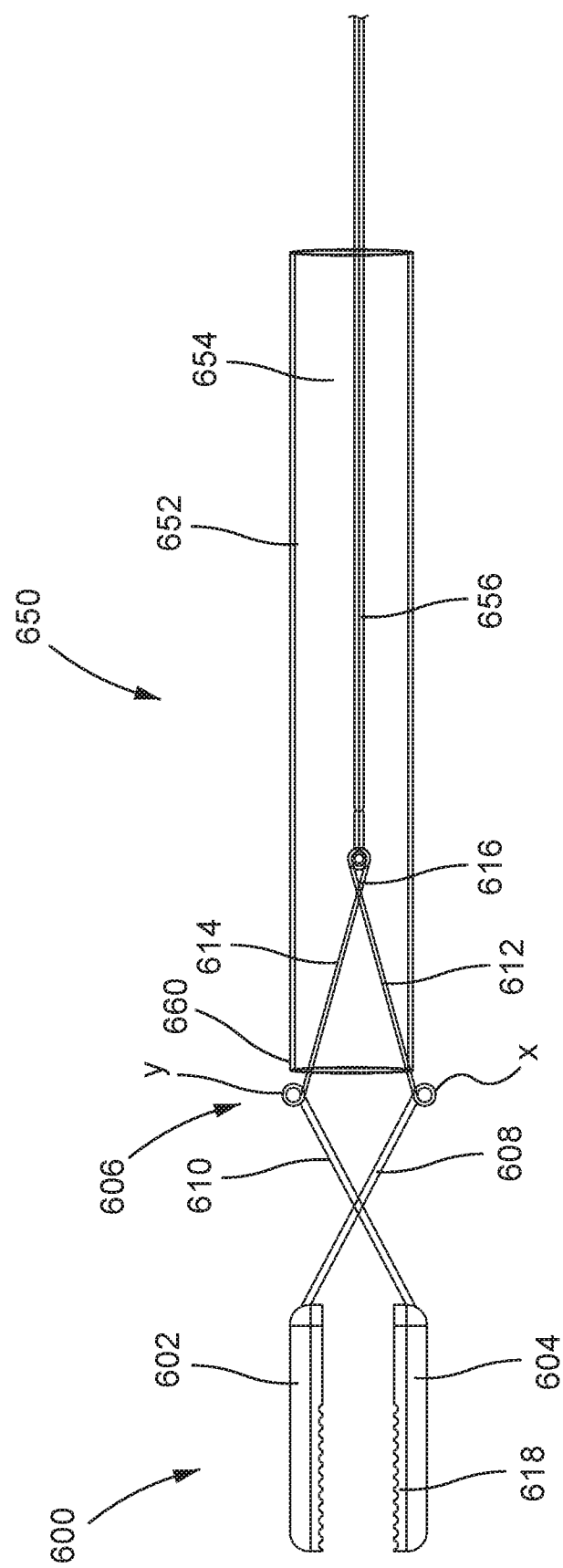

FIGS. 6A and 6B depict side and perspective views, respectively, of another variation of a system in which the grasper comprises a clamp. As shown there, the system may comprise a clamp 600 and a delivery device 650. The clamp 600 may be releasably coupled to and decoupled from the delivery device 650, as shown in FIGS. 6A and 6B, respectively. When the clamp 600 is coupled to the delivery device 650, the delivery device 650 may actuate the clamp 600 to connect the clamp 600 to tissue or to detach the clamp 600 therefrom.

As in the variations discussed above, in some variations, the delivery device 650 and the clip 600 may be configured for laparoscopic introduction into the body. In these variations, the clamp 600 may be sized such that it may be advanced through a laparoscopic port. In some instances, the clamp 600 may be sized such that it may fit through a laparoscopic port when the clamp 600 is in the open configuration, the closed configuration, or either the open or closed configuration. In some of these variations, the largest width of the clamp 600 in a closed configuration may be less than or equal to about 10 umm, so that the clamp 600 may be advanced through a 10 mm laparoscopic port when the clip is in the closed configuration. Similarly, a distal portion of the delivery device 650 may also be sized such that it may fit through a laparoscopic port. In some variations, the delivery device 650 may be configured such that the distal portion of the delivery device 650 (e.g., an outer sheath 652, as discussed in more detail herein) may have a diameter less than or equal to about 10 mm. The clamp 600 and delivery device 650 may be formed from any suitable materials, such as one or more of medical grade, high-strength plastics or metals, such as stainless steel, cobalt chromium, nickel titanium, PEEK, one or more nylons, polyimide, or the like, and/or may at least partially be formed from magnetic materials, as described herein.

The clamp 600 may comprise a first gripping pad 602, a second gripping pad 604, and a wire 606 connecting the first pad 602 and the second pad 604. The wire 606 may have a scissor-like configuration, manipulation of which may allow the clamp 600 to be actuated between closed and open configurations. This in turn may allow the clamp 600 to releasably connect to tissue. When the clamp 600 is in an open configuration, the first pad 602 and the second pad 604 may be separated to define a space between the first pad 602 and the second pad 604, such as shown in FIG. 6A. When the clamp 600 is moved to the closed configuration, the distance between the pads 602 and 604 may be reduced. In some instances, the pads may be positioned in contact with each other when the clamp is in its closed configuration. When tissue is positioned between the pads 602 and 604 (such as tissue 690 shown in FIG. 6B), the tissue may prevent the first pad 602 from contacting the second pad 604 when the clamp 600 is in a closed configuration.

In the variation shown in FIGS. 6A and 6B, the wire 606 may comprise first and second distal portions (labeled 608 and 610, respectively) and first and second proximal portions (labeled 612 and 614, respectively), and may have a diamond-like shape. A distal end or portion of the first distal portion 608 may be connected to the first jaw 602, and a proximal end or portion of the first distal portion 608 may be connected to the first proximal portion 612. Similarly, a distal end or portion of the second distal portion 610 may be connected to the second jaw 604, and a proximal end or portion of the second distal portion 610 may be connected to the first proximal portion 614. The first and second proximal portions 612 and 614 may connected at their proximal ends, and the two distal portions 608 and 610 may cross each other to cause the wire 606 to define a substantially diamond shape.

In some variations, the wire 606 may be formed with loops at the junctions between the first distal portion 608 and first proximal portion 612, between second distal portion 610 and second proximal portion 614, and between first and second proximal portions 612 and 614 (these loops are labeled as 620, 622, and 616, respectively). Each loop may comprise one or more coils. Each loop may act as a torsion spring, such that rotation between two portions from a resting position may store energy in the loop connecting them, thereby providing a biasing force toward the resting position. Accordingly, the loops 620, 622, and 616 may bias the wire 606 toward a closed configuration (such as shown in FIG. 6B), and may press the first 602 and second 604 pads together in the closed configuration. While shown in FIGS. 6A and 6B as being formed from one continuous wire, the wire 606 need not be. In other variations, the wire 606 may be comprised of two or more segments of wire that may be joined together. Additionally or alternatively, although the first and second distal portions 608 and 610 and the first and second proximal portions 612 and 614 of the wire 606 are shown in FIGS. 6A and 6B as being substantially straight segments, all or some of these wire segments may be comprise one or more curves. Additionally or alternatively, while shown in FIGS. 6A and 6B as having loops at each of the junctions between the first proximal portion 608 and the first distal portion 612, the second proximal portion 610 and the second distal portion 614, and between the first and second distal portions 612 and 614, the wire 606 may be configured such that it has loops at only some or none of these junctions.

The wire may have any suitable properties to have a desired torsion coefficient, and in turn a desired clamping force on tissue. For example, the wire diameter, loop diameter, and number of coils in each loop may affect the torsion. Increasing the wire diameter, decreasing the loop diameter, and/or decreasing the number of coils per loop may increase the torsion coefficient, and in turn the clamping force on tissue. Conversely, decreasing the wire diameter, increasing the loop diameter, and/or increasing the number of coils per loop may decrease the torsion coefficient, and in turn the clamping force on tissue. In some variations, the wire diameter may be between about 0.015 inches and about 0.030 inches. In other variations, the wire diameter may be between about 0.01 inches and about 0.02 inches, about 0.02 inches and about 0.04 inches, about 0.04 inches and about 0.05 inches, about 0.05 inches and about 0.06 inches, or greater. It should be appreciated that in some variations the wire may have a constant diameter along its length, while in other variations the wire may have a variable diameter along its length. In some variations, the loop diameters may be between about 1 mm to about 5 mm (e.g., between about 1 mm and about 2 mm, about 2 mm and about 3 mm, about 3 mm and about 4 mm, about 4 mm and about 5 mm). In other variations, the loop diameters may be between about 5 mm and about 6 mm, about 6 mm and about 7 mm, about 7 mm and about 8 mm, about 8 mm and about 9 mm, about 9 mm and about 10 mm, or greater. The loop diameters may be sized such that they are configured to fit within delivery device 650. It should be appreciated that each loop may have a different diameter than the other loops, or two or more loops (including all loops) may have the same diameter. In some variations, the loops may comprise a single coil. In other variations, the loops may comprise multiple coils (e.g., two, three, four, five, six, or more). The number of coils may be such that the loops may be configured to fit within delivery device 650. It should be appreciated that each loop may have a different number of coils, or two or more loops (including all loops) may have the same number of coils.

All or part of the inner surfaces 610 and 612 of the pads 602 and 604, respectively, may comprise one or more features that may promote engagement with tissue, but need not. In some variations, all or part of the inner surfaces 610 and 612 of the pads 602 and 604, respectively, may be roughened or texturized, which may help to reduced slipping between the pads and tissue. Additionally or alternatively, the all or part of the inner surfaces 610 and 612 may comprise teeth or ridges 618 (as shown in FIG. 6A) or other projections that may facilitate engagement of the pads 602 and 604 with tissue. In some variations of the clamp described here, the clamp may comprise one or more coatings that may help to smooth discontinuities in the contours of the grasper and may act to provide one or more atraumatic surfaces of the grasper.

The one or more coatings may comprise silicone, urethane, one or more nylon blends, polyethylenes, fluoropolymers, combinations thereof, and the like.

Generally, at least a portion of the clamp 600 described here may be formed from one or more materials which may be attracted to a magnetic field, as described in more detail herein, but need not be. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. In variations in which the materials include steel alloys, the steel alloys may be in a martensitic state. In some variations, coldworking may be used to improve the magnetic permeability of the clamp 600, for instance during the machining process. Having at least a portion of the clamp 600 formed from one or more metallic of magnetic materials that may be attracted to a magnetic field may allow the clamp 600 to be manipulated by a magnetic control assembly, as will be discussed in more detail herein.

The clamp 600 may be manipulated, actuated, and or delivered by a delivery device. For example, FIGS. 6A and 6B depict a variation of a delivery device 650 which may be used to actuate the clamp 600. As shown there, the delivery device 650 may comprise a an outer sheath 652 having a lumen 654 and a pull wire 656 having a distal hook 658 extending through the outer sheath 652. While the outer sheath 652 is shown as having a constant diameter in FIGS. 6A and 6B, in other variations the outer sheath may have a tapered shape, such that the diameter of the outer sheath increases or decreases from the distal to proximal ends.

To releasably couple the clamp 600 to the delivery device 650, the distal hook 658 may engage a portion of the wire 606, and the distal hook 658 may be withdrawn relative to the outer sheath 652 (e.g., by withdrawing the pull wire 656) to pull the clamp 600 into contact with the outer sheath 652. Holding the clamp 600 in contact with the outer sheath 652 using the distal hook 658 may temporarily keep the clamp 600 engaged with the delivery device 650. In some instances, to engage the wire 606, the distal hook 658 may be placed into the loop 616 between the first and second proximal portions 612 and 614 of the wire 606. The position of the pull wire 656 and the distal hook 658 relative to the outer sheath 652 may be controlled by any suitable mechanism, such as a triggering mechanism that may be manipulated by the user at a proximal portion of the delivery device (e.g., a handle or the like).

The distal hook 658 and pull wire 656 may also be manipulated to actuate the clamp 600. When the distal hook 658 is retracted relative to the outer sheath 652 to pull the clamp 600 into contact with the outer sheath 652, further retraction of distal hook 658 may cause a distal end 660 of the cylinder 652 to contact and press against the first and second proximal portions 612 and 614 of the wire 606. This may cause the first and second proximal portions 612 and 614 to rotate towards each other, which in turn may push the pads 602 and 604 away from each other to move the clamp 600 into an open configuration, as shown in FIG. 6A.

Conversely, the distal hook 658 may be advanced (or the outer sheath 652 may be moved proximally) to advance the clamp 600 relative to the outer sheath 652. As the clamp 600 is advanced relative to the outer sheath 652, the constraining forces provided by the outer sheath may be removed, and the first and second proximal portions 612 and 614 may rotate away from each other (e.g., via mechanical energy stored in the loop 616), which may move the first and second pads 602 and 604 toward each other, thereby returning the clamp 600 to a closed configuration. When a tissue (such as tissue 690 shown in FIG. 6B) is positioned between the first and second pads 602 and 604 when the clamp 600 is in an open configuration, moving the clamp 600 to a closed configuration may releasably connect the clamp 600 to tissue 690. Once the clamp 600 holds tissue between the first pad 602 and the second pad 604, the clamp 600 may be controlled by the magnetic control assembly to manipulate the attached tissue, as discussed herein. The hook 648 may then be disengaged from the clip loop 616 to disconnect the grasper 600, which can then be removed from the anatomical cavity. If desirable, the delivery device 650 may subsequently reengage the clamp 600 to disconnect the clamp 600 from the tissue and/or reposition the clamp 600.

Figure 7A:
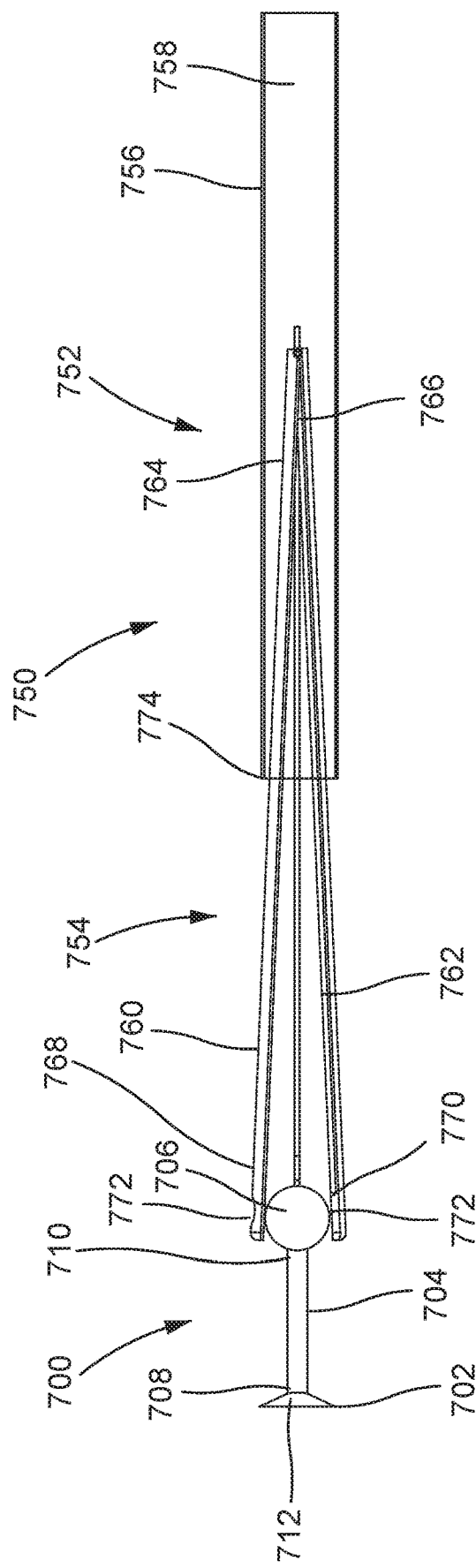
FIGS. 7A-7B depict side views of a variation of the systems described here.
Figure 7B:
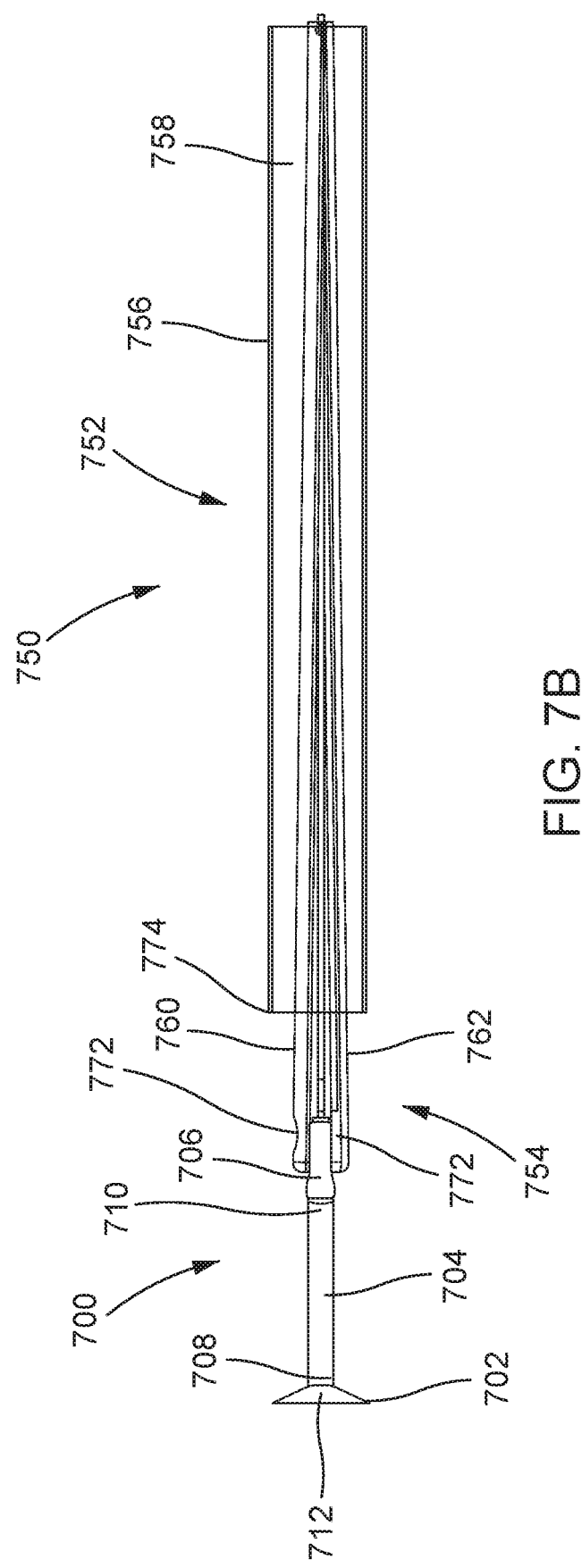

In some variations of the systems described here, the system may comprise a grasper configured to attach to tissue using a vacuum between the grasper and the tissue. FIGS. 7A and 7B depict one such variation of a system comprising a grasper 700 and a delivery device 750. It should be appreciated that the grasper 700 may be actuated and delivered using any suitable delivery device (such as those described here) and the delivery device 750 may be used to actuate and/or deliver any suitable grasper (such as those described here). When the grasper 700 is coupled to the delivery device 750, the delivery device 750 may actuate the grasper 700 to connect the grasper 700 to tissue or to detach the grasper 700 therefrom. The grasper 700 and the delivery device 750 will each be discussed in more detail herein.

As in other variations discussed herein, in some variations, the delivery device 750 and the grasper 700 may be configured for laparoscopic introduction into the body, such as discussed in more detail herein. In these variations, the grasper 700 may be sized such that it may be advanced through a laparoscopic port. In some instances, the grasper 700 may be sized such that it may fit through a laparoscopic port when the grasper 700 is in the open configuration, the closed configuration, or either the open or closed configuration. In some of these variations, the largest width of the grasper 700 in a closed configuration may be less than or equal to about 10 mm, so that the grasper 700 may be advanced through a 10 mm laparoscopic port when the clip is in the closed configuration. Similarly, a distal portion of the delivery device 750 may also be sized such that it may fit through a laparoscopic port. In some variations, the delivery device 750 may be configured such that the distal portion of the delivery device 750 may have a diameter less than or equal to about 10 mm.

In the embodiment of the grasper 700 shown in FIGS. 7A and 7B, the grasper 700 may be configured to releasably adhere to tissue using suction. As shown in FIGS. 7A and 7B, the grasper 700 may comprise a suction cup 702, a tube 704, and a bladder 706. Generally, the tube 704 may have a lumen extending between a distal opening 708 and a proximal opening 710 of the tube 704, which may fluidly connect the suction cup 702 and the bladder 706. Specifically, the distal opening 708 of the tube 704 may connect to an opening 712 through the suction cup 702, which may allow the bladder 706 to displace air from or draw air through the suction cup 702. Specifically, compression of the bladder 706 may push air out of the bladder 706, which in turn may drive the air through the tube 704 and out of the suction cup 702.

To connect the grasper 700 to tissue, the bladder 706 may be compressed to evacuate air from the bladder 706 out of the suction cup 702, and the suction cup 702 may be positioned against tissue. With the suction cup 702 positioned against tissue, the compressive force applied to the bladder 706 may be at least partially released. Due to the tendency of the bladder 706 to return to an uncompressed configuration, the bladder 706 may attempt to draw air into the bladder 706, but the presence of the tissue in the suction cup 702 may prevent air from passing into the bladder 706 through the suction cup 702. Accordingly, the bladder 706 may instead provide a vacuum force to the tissue via the tube 704 and the opening 712 in the suction cup 702. This vacuum force may hold the grasper 700 against the tissue. To release the grasper 700 from tissue, the bladder 706 may again be compressed to remove the vacuum force.

Generally, the suction cup 702 may be configured to promote connection of the grasper 700 to tissue. For example, the suction cup 702 may be formed from a shape that defines a cavity configured to at least partially receive tissue. In some variations, the suction cup 702 may have a hemispherical or a conical shape. Additionally or alternatively, the suction cup 702 may comprise one or more tabs or other protrusions that may be configuration to at least partially wrap around tissue. In these variations, the tabs/protrusions may engage tissue and may help to hold it temporarily in place.

While the bladder 706 is shown in FIGS. 7A and 7B as having a generally spherical shape, it should be appreciated that the bladder may have any suitable shape, such as, for example, a bulbous shape, a cylindrical shape, a box shape, or the like. The size of the bladder 706 and suction cup 702 may be chosen based on the desired suction strength. For example, a larger bladder and/or suction cup may allow the grasper 700 to provide a larger vacuum force to tissue, which may more strongly adhere the grasper 700 to the tissue.

The grasper 700 and delivery device 750 may be formed from any suitable materials, such as one or more of medical grade, high-strength plastics or metals, such as stainless steel, cobalt chromium. PEEK, one or more nylons, polyimide, or the like, and/or may be at least partially formed from materials that may be attracted to a magnetic field, as described herein. In some variations, the bladder 706 may be formed from one or more resilient materials, such as one or more rubbers (e.g., silicon, one or more thermoset elastomers) or urethanes such that the bladder 706 has a tendency to return to an uncompressed configuration. In these variations, as the bladder 706 returns to an uncompressed configuration, the bladder 706 may draw air into the bladder 706 through the suction cup 702 and the tube 704. Additionally, in some variations, the suction cup 702 may be formed from a deformable or flexible material, which may allow the suction cup 702 to deform to accommodate irregular tissue. For example, in some variations the suction cup 702 may be formed from one or more rubbers (e.g., silicon, one or more thermoset elastomers) or urethanes. It should be appreciated that the suction cup 702 and bladder 706 may be formed from the same material or combination of materials, or may be formed from different materials.

Generally, at least a portion of the grasper 700 described here may be formed from one or more materials which may be attracted to a magnetic field, as described in more detail herein, but need not be. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. In variations in which the materials include steel alloys, the steel alloys may be in a martensitic state. In some variations, coldworking may be used to improve the magnetic permeability of the grasper 700, for instance during the machining process. Having at least a portion of the grasper 700 formed from one or more metallic or magnetic materials that may be attracted to a magnetic field may allow the grasper 700 to be manipulated by a magnetic control assembly, as will be discussed in more detail herein. In some variations, at least a portion of the bladder may comprise magnetic or ferromagnetic materials to facilitate engagement by the delivery device (as described in more detail herein), but need not.

One or more delivery devices may be configured to compress and/or release the bladder 706 to releasably connect the grasper 700 to tissue. For example, FIGS. 7A and 7B show one such variation of a delivery device 750. As shown there, the delivery device 750 may comprise an elongate sheath 752 and an engagement portion 754. The elongate sheath 752 may comprise a lumen 758 extending at least partially therethrough, which may be sized to at least partially hold the engagement portion 754. The elongate sheath 752 and the engagement portion 754 maybe cooperate to hold and actuate a grasper (such as the grasper 700 shown in FIGS. 7A-7B), as will be discussed in more detail herein.

The engagement portion 754 may comprise a first elongate member 760 and second elongate member 762. The engagement portion 754 may have an open and a closed configuration. In some variations, the first elongate member 760 and second elongate member 762 may be rotatably connected or otherwise attached at their proximal ends 764 and 766, respectively, but need not be attached. In variations in which the elongate members are attached, the attachment mechanism may allow for the engagement portion 754 to be moved between the open and closed configurations. In some variations, the attachment mechanism may be a pivot joint. In other variations, the first elongate member 760 and second elongate member 762 may be welded, fused, or otherwise joined together, and the members may be sufficiently flexible to allow the engagement portion 754 to move between closed and open configurations.

When the engagement portion 754 is moved to the open configuration, the distal portions 768 and 770 of first elongate member 760 and second elongate member 762, respectively, may be spaced apart to define a space between the distal portions 768 and 770 of first elongate member 760 and second elongate member 762, as shown in FIG. 7A. In variations in which the elongate members are attached such that an attachment mechanism rotatably connects the first and second elongate members 760 and 762, in the open configuration, the distal portions 768 and 770 of the first and second elongate members 760 and 762 may be rotationally biased away from each other to define a space between the distal portions 768 and 770 of first and second elongate members 760 and 762. In the closed configuration, the distal portions 768 and 770 of first elongate member 760 and second elongate member 762 may be moved closer than in the open configuration, as shown in FIG. 7B. In variations in which the elongate members are attached such that an attachment mechanism rotatably connects the first and second elongate members 760 and 762, in the closed configuration, the distal portions 768 and 770 of the first and second elongate members 760 and 762 may be rotationally biased toward each other to reduce or eliminate space between the distal portions 768 and 770 of the first and second elongate members 760 and 762.

While it may be possible for the distal portion 768 of the first elongate member 760 to be moved into contact with the distal portion 770 of the second elongate member 762, this may not be necessary for the engagement portion 754 to releasably engage a grasper. For example, when the engagement portion 754 releasably engages with the grasper 700 depicted in FIGS. 7A-7B, the grasper 700 may prevent the distal portions 768 and 770 of the first elongate member 760 and second elongate member 762 from contacting each other, and/or may prevent the first elongate member 760 and second elongate member 762 from fully closing.

In some variations, the first elongate member 760 and the second elongate member 762 may be configured such that their distal ends 768 and 770 are biased away from each other, which may in turn bias the engagement portion 754 toward and open configuration. For example, in some variations the engagement portion 754 may comprise a spring (not shown), such as a compression spring, which may spring-bias the engagement portion 204 toward an open position, such as shown in FIG. 7A. In variations where the first elongate member 760 and second elongate member 762 are welded together, they may be welded in an open configuration but may be sufficiently flexible to allow the first elongate member 760 and second elongate member 762 to be pressed toward each other into a closed configuration. In other variations, the first and second elongate members 760 and 762 may be spring-biased toward each other, for instance with an extension spring, leaf spring, or torsional spring, which may bias the engagement portion 754 toward a closed configuration. In some variations, the delivery device 750 may comprise a control that may be used to overcome the bias of an engagement portion (such as the engagement portion 754) toward a closed configuration, which may thus allow the engagement portion 754 to be moved into an open configuration.

As mentioned above, the engagement portion 754 of the delivery device 750 may be configured to releasably couple to and actuate a grasper, such as the grasper 700 shown in FIGS. 7A-7B. For example, in some instances the distal portions 768 and 770 of first elongate member 760 and second elongate member 762 may be configured to releasably engage the grasper 700. The bladder 706 of grasper 700 may be positioned between the distal ends 768 and 770 of the first and second elongate members 760 and 762, respectively, of the delivery device 750. The grasper 700 may be held between the distal ends 768 and 770 of the first and second elongate members by a clamping force between the distal ends 768 and 770. For example, in variations in which the engagement portion 754 of the delivery device 750 is biased toward a closed configuration, the biasing force may create a clamping force.

In some variations, the distal portions 768 and 770 of the first and second elongate members 760 and 762, respectively, may comprise features that may improve the ability of the delivery device 750 to reliably grip onto a grasper (such as grasper 700), but need not comprise such features. For example, the delivery device 750 may comprise apertures or recesses (e.g., apertures 772 shown in FIGS. 7A-7B) extending at least partially through the distal ends 768 and 770 of the first and second elongate members 760 and 762. When the grasper 700 is positioned between the distal ends 768 and 770 of first and second elongate members 760 and 762, the bladder 706 may be configured to sit within one or more of the apertures 772. This may help to maintain engagement between the engagement portion 754 and the grasper 700 by allowing a greater area of contact between the bladder 706 and delivery device 750, and by the inner walls of the apertures 772 exerting inward forces on the bladder 706 that may tend to keep the bladder 706 within the apertures 772. In some variations, the bladder 706 may additionally be secured in the apertures 772 by a force biasing the first and second elongate members 760 and 762 toward each other, as described herein.

In some variations, there may be an attractive force between distal portions 768 and 770 of first and second elongate members 760 and 762 and one or more portions of the grasper 700 (e.g., the bladder 706). In some variations, this attractive force may be magnetic. In variations in which the attractive force is magnetic, the magnetic force may be generated by the distal portions 768 and 770 of the first and second elongate members 760 and 762, and one or more portions of the grasper 700, comprising magnetic or ferromagnetic materials. In variations in which one or more portions of a grasper (e.g., the bladder 706 of grasper 700) comprise magnetic materials, the distal portions 768 and 770 of the elongate members 760 and 762 may comprise magnetic or ferromagnetic materials; in variations in which one or more portions of a grasper (e.g., the bladder 706 of grasper 700) comprise ferromagnetic materials and no magnetic materials, the distal portions 768 and 770 of the elongate members 760 and 762 may comprise magnetic materials.

When the delivery device 750 has engaged a grasper (such as grasper 700 shown in FIGS. 7A-7B), the delivery device 750 may additionally be configured to actuate the grasper between uncompressed and compressed configurations. To move the grasper 700 between its uncompressed and compressed configurations, the engagement portion 754 may be selectively moved between its open and closed configurations, respectively. For example, as the engagement portion 754 is moved toward its closed configuration (such as shown in FIG. 7B), the distal portions 768 and 770 of the first and second elongate members 760 and 762 may be moved toward each other. This may apply a compressive force to the bladder 706 of grasper 700, which may cause the grasper 700 to move into a compressed configuration. Conversely, moving the engagement portion 754 toward its open configuration may release the compressive force on bladder 706 of grasper 700, which may allow the grasper 700 to return to its uncompressed configuration, such as shown in FIG. 7A.

The engagement portion 754 may be moved between its open and closed configurations in any suitable manner. In some variations, the engagement portion 754 may be actuated by advancing or retracting the engagement portion 754 through the lumen 758 of elongate sheath 752 of the delivery device 750. Movement of the elongate sheath 752 distally relative to the engagement portion 754 may cause the inner surface of elongate sheath 752 at the distal end 774 to contact the outer surface of the first and second elongate members 760 and 762. Further movement of the elongate sheath 752 distally relative to the engagement portion 754 may then cause the elongate sheath 752 to press against the outer surfaces of the first and second elongate members 760 and 762, which may force the distance between the first and second elongate members 760 and 762 to stay constant at the point where the first and second elongate members 760 and 762 contact the elongate sheath 752. As a result, the movement of the elongate sheath 752 distally relative to the engagement portion 754 may push the engagement portion 754 toward a closed configuration. When the engagement portion 754 is moved toward a closed configuration, distal ends 768 and 770 of the first and second elongate members 760 and 762 may be moved toward each other, which in turn may compress the bladder 706 of grasper 700. This may move the grasper 700 into a compressed configuration, as shown in FIG. 7B. Conversely, when the elongate sheath 752 is moved proximally relative to the engagement portion 754, the elongate sheath 752 may contact the engagement portion 754 at an increasingly proximal portion of the first and second elongate members 760 and 762, which may allow the first elongate member 760 and the second elongate member 762 to move away from each other, returning to an open configuration, as shown in FIG. 7A. This may release the pressure on the bladder 706 of grasper 700, which in turn may cause the bladder 706 of 700 to return to an uncompressed configuration, as shown in FIG. 7A.

The delivery device 750 may be used to releasably attach a grasper (such as grasper 700 depicted in FIGS. 7A-7B) to tissue. The grasper 700 may be engaged by the delivery device 750 (such as discussed in more detail herein), and the grasper 700 and a distal portion of the delivery device 750 may be advanced into a patient (e.g., into a body cavity such as the abdominal cavity) through an access site (e.g., such as a laparoscopic port). Once the grasper 700 is positioned within the body cavity, the delivery device 750 may be actuated to selectively move the grasper 700 between its compressed and uncompressed configurations in order to create a vacuum force to adhere the suction cup 702 of the grasper 700 to tissue. Once the grasper 700 is adhered to the tissue, the grasper 700 may be controlled by the magnetic control assembly to manipulate the attached tissue, as discussed herein. The engagement portion 754 may then be disengaged from the grasper 700 and removed from the anatomical cavity. If desirable, the delivery device 750 may subsequently reengage the grasper 700 to disconnect the grasper 700 from the tissue and/or reposition the grasper 700.

Figure 8A:
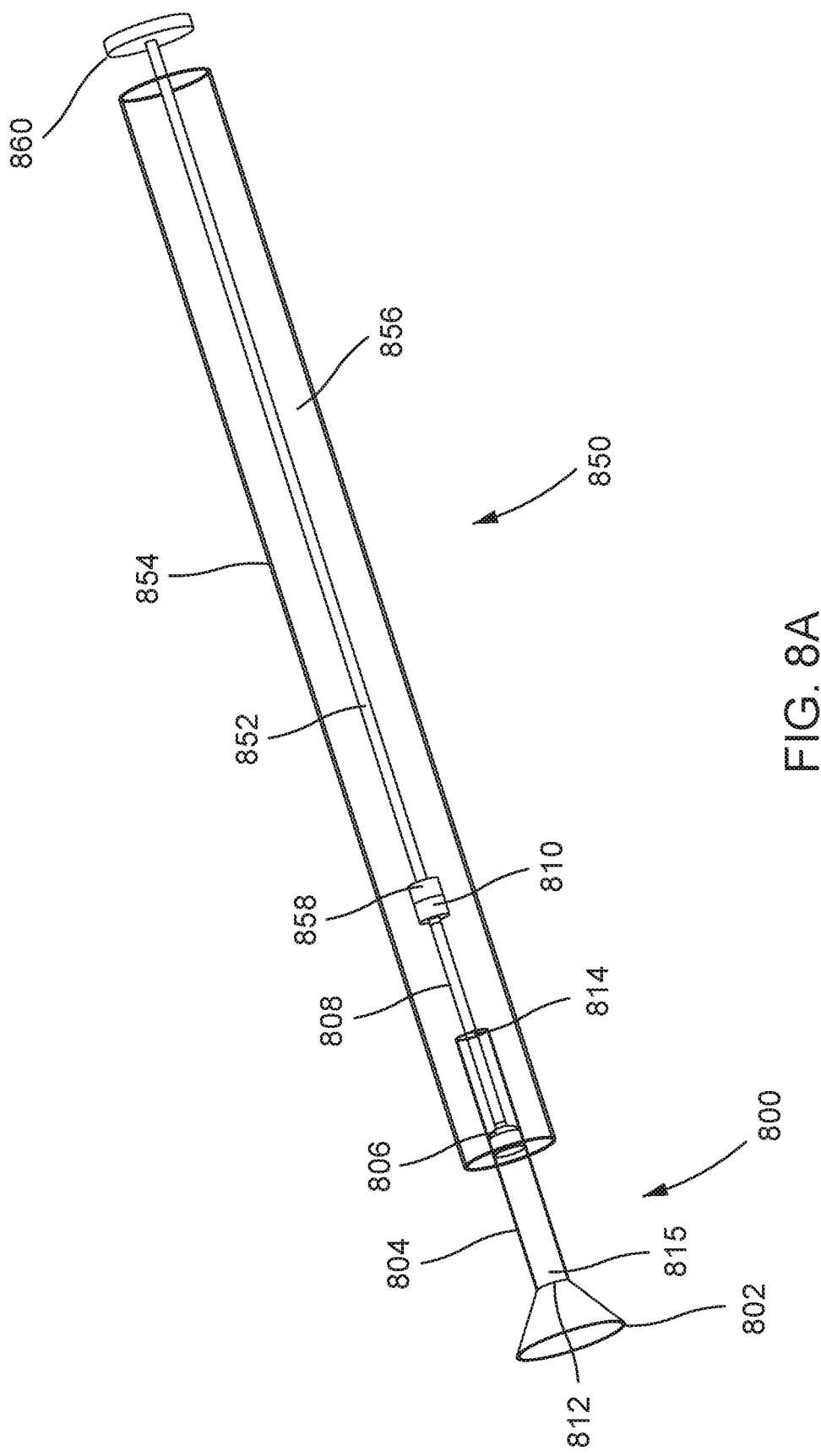
FIGS. 8A-8B depict perspective views of a variation of the systems described here.
Figure 8B:
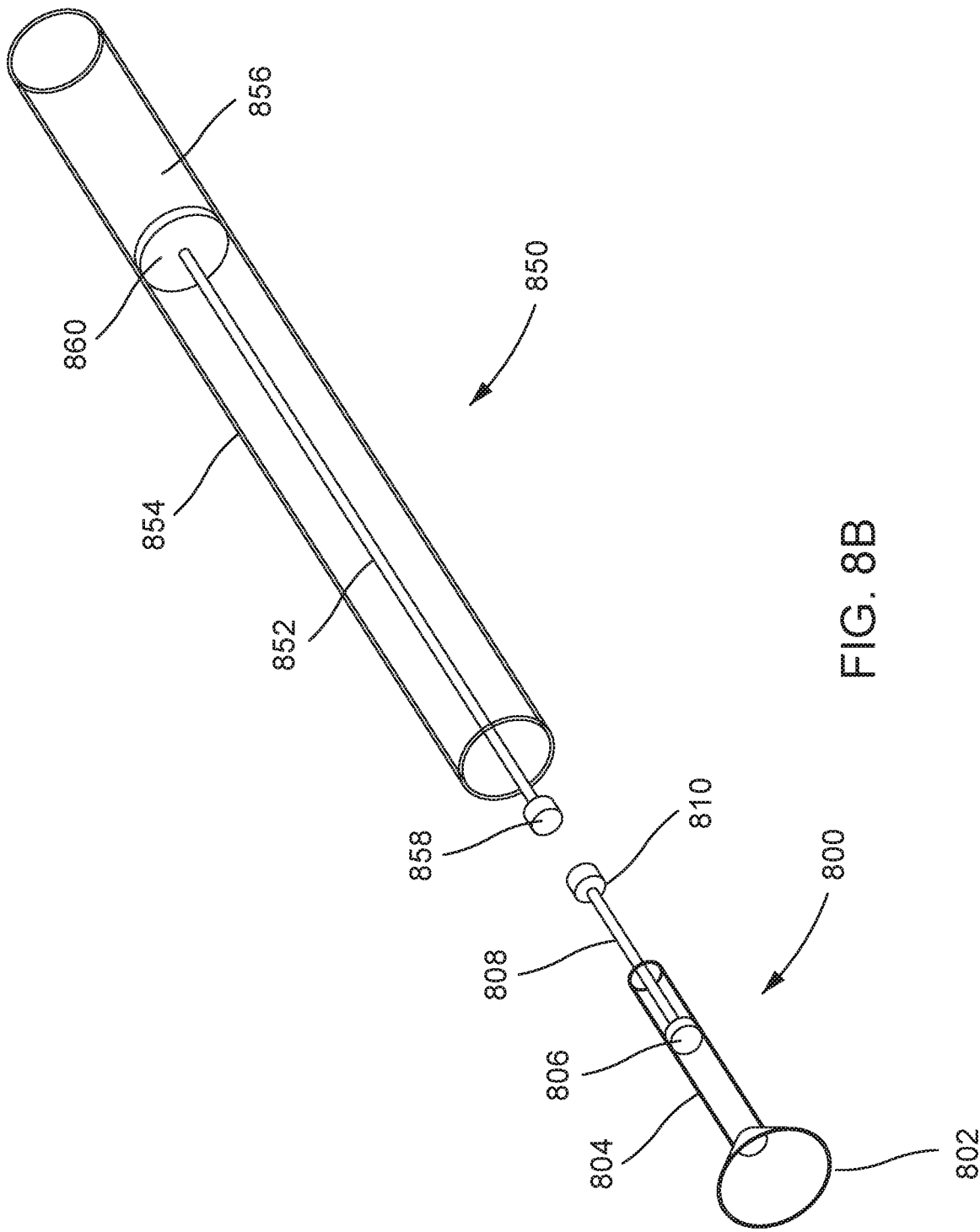

FIGS. 8A and 8B depict another variation of a system described here in which the system comprises a grasper configured to attach to tissue using a vacuum between the grasper and tissue. As shown there, the system may comprise a grasper 800 and a delivery device 850. Specifically, FIGS. 8A and 8B show perspective views of the grasper 800 and the delivery device 850. When the grasper 800 is coupled to the delivery device 850, the delivery device 850 may actuate the grasper 800 to connect the grasper 800 to tissue or detach the grasper therefrom, as described in detail herein. The grasper 800 may be releasably coupled to the delivery device 850 and decoupled from the delivery device 850. When the grasper 800 is coupled to the delivery device 850, the delivery device 850 may actuate the grasper 800 to connect the grasper 800 to tissue or to detach the grasper 800 therefrom.

In some variations, the delivery device 850 and the grasper 800 may be configured for laparoscopic introduction into the body, such as discussed in more detail herein. In these variations, the grasper 800 may be sized such that it may be advanced through a laparoscopic port. In some of these variations, the largest width of the grasper 800 (e.g., the diameter of the suction cup 802) may be less than or equal to about 10 mm, so that the grasper 800 may be advanced through a 10 mm laparoscopic port. Similarly, a distal portion of the delivery device 850 may also be sized such that it may fit through a laparoscopic port. In some variations, the delivery device 850 may be configured such that the distal portion of the delivery device 850 may have a diameter less than or equal to about 10 mm. The clip 800 and delivery device 850 may be formed from any suitable materials, such as one or more of medical grade, high-strength plastics or metals, such as stainless steel, cobalt chromium, PEEK, one or more nylons, polyimide, or the like, and/or may be at least partially formed from magnetic materials, as described herein. Additionally, in some variations, the suction cup 802 may be formed from a deformable or flexible material, which may allow the suction cup 802 to deform to accommodate irregular tissue. For example, in some variations the suction cup 802 may be formed from one or more rubbers (e.g., silicon, one or more thermoset elastomers) or urethanes.

In the embodiment of the grasper 800 shown in FIGS. 8A and 8B, the grasper 800 may be configured to releasably adhere to tissue using suction. As shown in FIGS. 8A and 8B, the grasper 800 may comprise a suction cup 802, a tube 804, and a piston 806 slidably moveable within the tube 804 and connected to a piston rod 808. Generally, the tube 804 may have a lumen extending therethrough. The distal opening 815 of the tube 804 may connect to an opening 812 through the suction cup 802, which may allow the piston 806 to displace air from or draw air through the suction cup 802. Specifically, advancement of the piston 806 may push air out of the tube 804 and out of the suction cup 802. Conversely, retraction of the piston 806 may draw air through the suction cup 802 and the tube 804.

To connect the grasper 800 to tissue, the piston 806 may be advanced to evacuate air from the tube 804 out of the suction cup 802, and the suction cup 802 may be positioned against tissue. With the suction cup 802 positioned against tissue, the piston 806 may be at least partially retracted. This may create a vacuum, as the presence of the tissue in the suction cup 802 may prevent air from passing into the tube 804 through the suction cup 802. Accordingly, the section cup 802 may instead provide a vacuum force to the tissue. This vacuum force may hold the grasper 800 against the tissue. To release the grasper 800 from tissue, the piston 806 may be advanced to remove the vacuum force.

The proximal end of the piston rod 808 may have an attached linking element 810, which may allow the grasper 800 to be engaged by the delivery device 850, as describe in more detail herein. The linking element 810 may comprise a magnetic or ferromagnetic material, such as, for example, stainless steel, iron, cobalt, nickel, neodymium iron boron, samarium cobalt, alnico, ceramic ferrite, alloys thereof and/or combinations thereof. In addition to allowing for engagement with the delivery device 850, the linking element 810 may allow the grasper 800 to be manipulated by the magnetic control assembly.

Generally, the suction cup 802 may be configured to promote connection of the grasper 800 to tissue. For example, the suction cup 802 may be formed from a shape that defines a cavity configured to at least partially receive tissue. In some variations, the suction cup 802 may have a hemispherical or a conical shape. Additionally or alternatively, the suction cup 802 may comprise one or more tabs or other protrusions that may be configuration to at least partially wrap around tissue. In these variations, the tabs/protrusions may engage tissue and may help to hold it temporarily in place. The volume of the tube 804 and size of the suction cup 802 may be chosen based on the desired suction strength; a larger tube and/or suction cup may allow the grasper 800 to have greater negative pressure adhering the grasper 800 to the tissue.

The grasper 800 may be delivered and actuated by any delivery device that is configured to reversibly withdraw the piston 806 of the grasper 800 to create suction to hold the grasper 800 to tissue. In one variation shown in FIGS. 8A-8B, the delivery device 850 may comprise an elongate sheath 854 and an actuation rod 852. The actuation rod 852 may have a delivery linking element 858 at its distal end and a piston actuator 860 at its proximal end, and may be slidably disposed in a elongate sheath 854. The actuation rod 852 may be advanced through the lumen 856 of the elongate sheath 854 to hold and actuate a grasper (such as the grasper 800 shown in FIGS. 8A-8B), as will be discussed in more detail herein.

The delivery linking element 858 may be configured to releasably couple the delivery device 850 to the grasper 800 via magnetic attraction between the delivery linking element 858 and the linking element 810 of the grasper 800 described herein. At least a portion of the delivery linking element 858 may comprise one or more materials which may be attracted to a magnetic field. These materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. The delivery linking element 858 may be movable between an advanced position (as shown in FIG. 8B) and a retracted position (as shown in FIG. 8A). When the delivery linking element 858 of the delivery device 850 is brought in proximity to the linking element 810 of the grasper 800, the delivery linking element 858 of the delivery device 850 may engage linking element 810 of the grasper 800 via magnetic attractive force. When the grasper 800 and 850 are engaged, retracting and advancement of the actuation rod 852 relative to the tube 804 and suction cup 802 of grasper 800 may create suction to adhere the suction cup 802 to tissue. With the suction cup 802 of the grasper 800 pressed against tissue, the actuation rod 852 may be moved proximally relative to the suction cup 802 and tube 804, which may create a negative pressure within the suction cup 802 and tube 804. After the grasper 800 is attached to tissue, a magnetic force may be applied to the grasper 800 by the magnetic control element to manipulate the attached tissue.

In order for releasable engagement of the delivery linking element 858 of the delivery device 850 and the linking element 810 of the grasper 800, delivery device 850 may further comprise a depth stop that may prevent linking element 810 from moving proximal to a certain point within lumen 856 of elongate sheath 854. Thus, if actuation rod 852 is moved proximally beyond the depth stop, the force from the depth stop on the linking element 810 may overcome the engagement force connecting the delivery linking element 858 and the linking element 810 (e.g., a magnetic attractive force), and the delivery linking element 858 and the linking element 810 may disengage. In some variations (not shown), the depth top may comprise an inner sheath. The inner sheath may be sized such that the delivery linking element 858 can fit within the inner sheath, but the linking element 810 cannot. Thus, if the actuation rod 852, and thus the delivery linking element 858, are withdrawn proximally relative to and within the inner sheath, the linking element 810 of clip 100 may not be able to move proximally beyond the distal end of the inner sheath, and thus the distance between the delivery linking element 858 and the linking element 810 may increase. Because force applied by a magnet decreases as the function of the distance from the magnet, increasing this distance may decrease the magnetic attractive force felt between the delivery linking element 858 and linking element 810. Eventually, the attractive force may be sufficiently diminished such that the delivery linking element 858 may decouple from the linking element 810. If desirable, the delivery device 850 may subsequently reengage the clip 800 to disconnect the clip 800 from tissue and/or reposition the clip 800.

In some variations, instead of a depth stop for releasable engagement of the delivery linking element 858 of the delivery device 850 and the linking element 810 of the grasper 800, delivery device 850, either the delivery linking element 858 or the delivery device 850 may comprise an electromagnet. The electromagnet may comprise an active configuration and an inactive configuration. The electromagnet may be activated in order to allow the delivery linking element 858 and delivery device 850 to releasably engage. Conversely, the electromagnet may be inactivated to allow the delivery linking element 858 and delivery device 850 to disengage. Additionally, although the system of FIGS. 8A-8B relies on magnetic attraction to couple the grasper 800 and delivery device 850, it should be appreciated that in some variations the delivery device 850 may comprise another attachment mechanism, such as a threaded rod that may be screwed onto the grasper tube end.

Figure 9A:
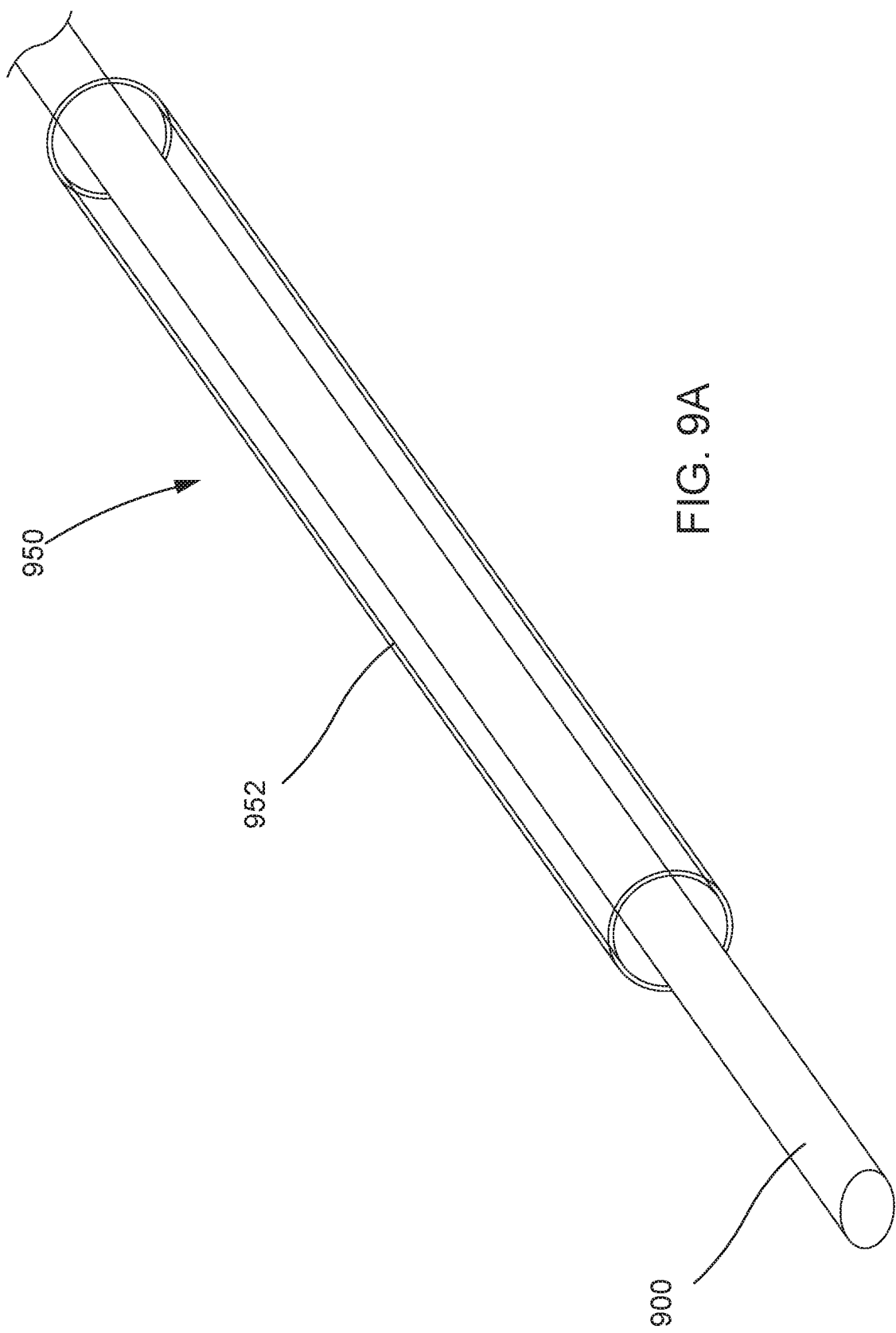
FIGS. 9A-9B depict perspective views of a variation of the systems described here.
Figure 9B:
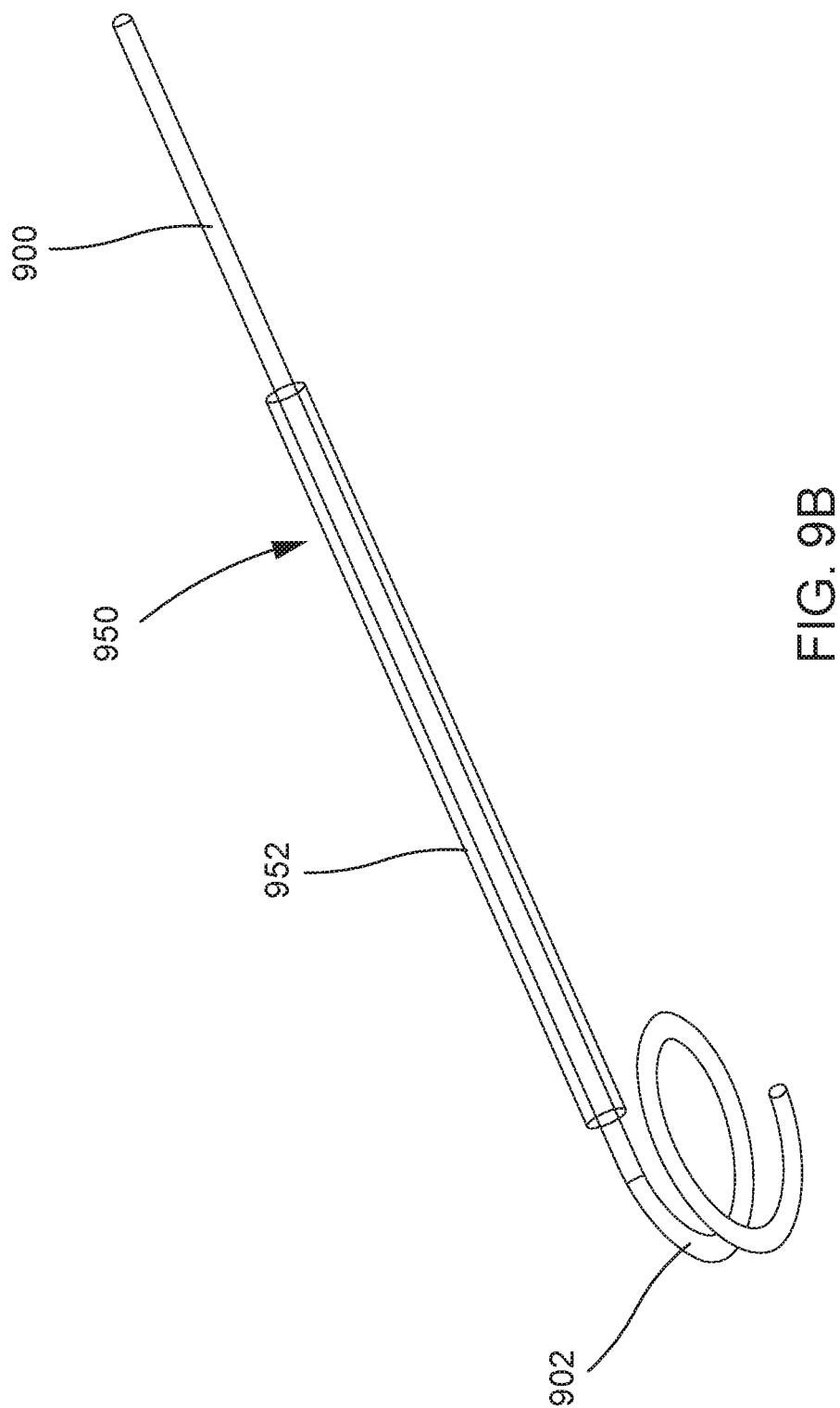

In addition to clip- or clamp-like grasping devices and suction-based devices, a system may include a wire having a pre-formed shape that may be configured to ensnare or otherwise engage tissue. FIGS. 9A-9B show perspective views of such a system comprising a wire 900 and a delivery device 950. The wire 900 may be deployed to wrap around or otherwise attach to tissue. In some variations, the wire 900 may be pre-shaped into a configuration configured to wrap around or otherwise attach to tissue, such as a coil, as shown in FIG. 9B. Generally, at least a portion of the wire 900 may be formed from one or more metallic or magnetic materials which may be attracted to a magnetic field, as described in more detail herein. The materials may include one or more magnetic or ferromagnetic materials, such as, for example, stainless steel, iron, cobalt, nickel, neodymium iron boron, samarium cobalt, alnico, ceramic ferrite, alloys thereof and/or combinations thereof. Having at least a portion of the wire 900 formed from one or more metallic or magnetic materials that may be attracted to a magnetic field may allow the wire 900 to be manipulated by the magnetic control assembly.

The delivery device 950 may comprise a shaft 952 configured to hold the wire 900 in a straightened configuration. The wire 900 may be inserted into the patient, for example through a laparoscopic port, while housed in the shaft 952. After the wire 900 is located near the target tissue, the wire 900 may be advanced distally out of the shaft 952, as shown in FIG. 9B. This may cause the wire to assume its pre-shaped configuration, which may allow it to attach to tissue. While the pre-shaped configuration is shown in FIG. 9A as being a coil 902, the wire may have any suitable shape configured to ensnare tissue. The wire may be fully deployed from the shaft 952, after which the shaft 952 may be removed from the patient. When the wire 900 has ensnared tissue, a magnetic force may be applied to the wire 900 by the magnetic control assembly, thus manipulating the attached tissue.

Magnetic Control Assembly

Once attached to tissue within the patient's body, the grasper may be manipulated by a magnetic control assembly. Generally, the magnetic control assembly may be configured to be placed outside a patient's body and to produce a magnetic field. The magnetic field produced by the magnetic control assembly may provide one or more forces to the magnetic device to control the position of the magnetic device. The magnetic control assembly may comprise at least one magnet configured to generate a magnetic field and at least one force modulation device. The force modulation device may control the magnitude of the force applied to the magnetic device.

In some embodiments, the force modulation device may comprise an adjustable shielding device, which may be configured to alter the magnetic field produced by the magnetic control assembly. Additionally or alternatively, the force modulation device may be configured to control a distance between the magnetic device and at least one magnet of the magnetic control assembly, which in turn may modulate the force applied to the magnetic device by the magnetic control assembly. In yet other embodiments, the force modulation device may be configured to both alter the magnetic field produced by the magnetic control assembly and control the distance between the magnetic control assembly and the magnetic device. In some variations, the magnetic control assemblies may comprise all or a portion of those described in U.S. application Ser. No. 14/200,302, filed on Mar. 7, 2014, and titled "Magnetic Control Assemblies and Systems Therefor." the contents of which are hereby incorporated by reference in their entirety.

Figure 10:
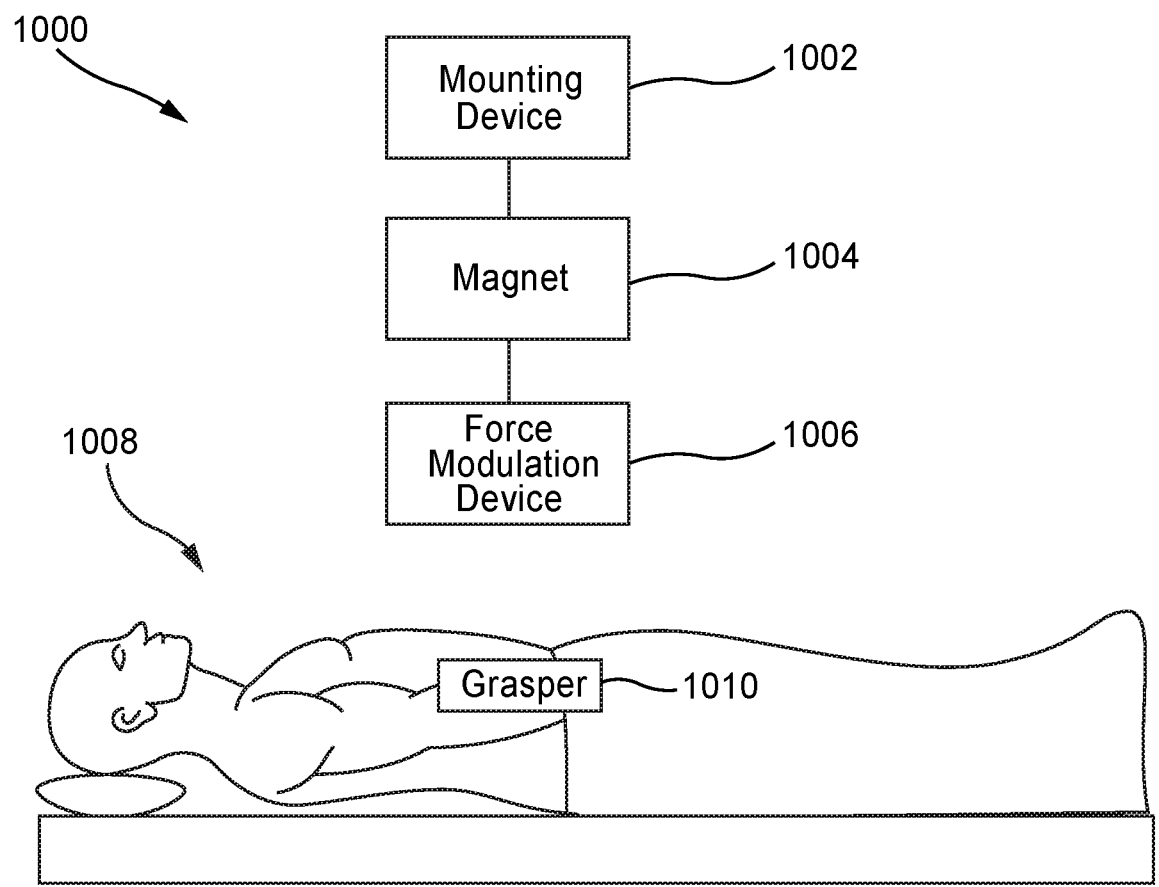
FIG. 10 depicts a block diagram of a variation of the systems described here.

FIG. 10 shows an illustrative variation of a magnetic control assembly. As shown there, in one variation the magnetic control assembly 1000 may comprise a mounting device 1002, a magnet 1004, and a force modulation device 1006. Although shown with a force modulation device, it should be appreciated that the magnetic control assembly 1000 need not comprise a force modulation device 1006. Similarly, the magnetic control assembly 1000 need not comprise a mounting device 1002.

The magnet 1004 may be configured to generate a magnetic field, such that when the magnetic control assembly 1000 is positioned near a patient 1008, the magnetic field may be generated inside the patient 1008. This magnetic field may apply a force to and manipulate a grasper 1010 positioned in the body. In some variations, the magnet 1004 may comprise one or more permanent magnets and/or one or more electromagnets. The magnet 1004 may comprise any number of individual magnets, which in some instances may be formed in an array. The magnet 1004 may have any suitable size and shape, such as cylindrical shape having a circular, oval, or semi-circle cross-section, a bar magnet having a rectangular or triangular cross section, a spherical magnet, or the like.

Generally, the mounting device 1002 may be configured to mount the magnetic control assembly 1000 to one or more structures (e.g., a wall, ceiling, an operating table, or the like). In some instances, the mounting device 1002 may be further configured to counterbalance the weight of the magnet 1004 and the force modulation device 1006, such that the magnet 1004 and the force modulation device 1006 may be moveably suspended by the mounting device 1006. With the magnetic control assembly 1000 suspended by the mounting device 1002, an operator may move the magnet 1004 and/or force modulation device 1006. Additionally or alternatively, the force modulation device 1006 may alter the positioning of the magnet 1004. In some variations, the position of the mounting device 1002 may be temporarily locked to fix the positions of the magnet 1004 and/or force modulation device 1006.

The force modulation device 1006 may be configured to modulate the strength of the magnetic field applied to a grasper 1010 positioned in the body. For example, in some instances it may be desirable to suspend the grasper 1010 against a tissue wall (e.g., the abdominal wall) while limiting the force that the grasper 1010 applies to the tissue wall. Accordingly, by modulating the strength of the magnetic field applied to the grasper 1010, the magnetic control assembly 1000 may control the force applied to the grasper 1010, which in turn may control the pressure applied by the grasper 1010 to the tissue wall. In some variations, the magnetic control assembly 1000 may comprise force modulation device 1006 that comprises an adjustable shielding device, which may alter the magnetic field produced by the magnet 1004 of the assembly. In other variations, the force modulation device 1006 may comprise a distance adjustment device, which may alter the distance between the magnet 1004 of the assembly and a grasper 1010 positioned in the body. In still other variations, the force modulation device 1006 may comprise an adjustable shielding device that is also configured to alter the distance between the magnet 1004 of the assembly 1000 and a grasper 1010 positioned in the body.

In some embodiments, the force modulation device 1006 may be controlled by an automated feedback loop based on a sensor located in the grasper 1010. This sensor may provide feedback, which is may be used by the magnetic control assembly to modulate the force applied to the grasper. In some variations of the graspers described here, the grasper may comprise at least one sensor. In some variations, the grasper may comprise a magnetometer configured to measure the strength of the magnetic fields applied to grasper. In these variations, the magnetometer may comprise a scalar magnetometer configured to measure a total strength of the magnetic field applied thereto or may comprise a vector magnetometer configured to measure the strength of a magnetic field in a particular direction. In some instances, a grasper may comprise a plurality of vector magnetometers configured to measure the strength of a magnetic field in multiple directions (e.g., along two axes, along three axes, or the like).

Additionally or alternatively, in some variations, the graspers described here may comprise a pressure sensor configured to measure pressure applied to one or more surfaces of the grasper. For example, when the grasper is pulled against an abdominal wall of a patient, the pressure sensor may be configured to measure the pressure between the grasper and the abdominal wall. It may be desirable to limit this pressure, as too much pressure applied to the abdominal wall may block blood flow thereto and possibly cause tissue necrosis. The grasper may comprise any combination of pressure sensors and magnetometers. When a grasper comprises at least one sensor, the grasper may be configured to communicate data from the sensor or sensors to the magnetic control assembly. In some variations, the grasper may be configured to communicate this data wirelessly. Additionally or alternatively, the grasper may be configured to produce one or more signals which may be used by the magnetic control assembly to determine a relative positioning between the grasper and the magnetic control assembly.

Methods

As mentioned above, the graspers described here may be used to provide remote suspension of tissue during a minimally-invasive procedure. Generally, to provide suspension of a tissue, a grasper as described herein may be advanced into the body, may be releasably connected to a tissue in the body, and may be suspended using one or more magnets positioned externally to the body to move and suspend the tissue. In some variations, the grasper may be detached from the tissue, and the grasper may be repositioned and reconnected to tissue (either the same tissue or different tissue).

The grasper, such as any of the graspers described herein, may be advanced into the body in any suitable manner. In some variations, the grasper may be advanced into the body through a laparoscopic port as part of a laparoscopic procedure. In some instances, the laparoscopic procedure may be a single-incision laparoscopic procedure. In some variations, the grasper may be advanced into the body using a delivery device, such as any of the delivery devices described herein. In these variations, the grasper may be releasably coupled to a distal engagement portion of the delivery device, and the distal engagement portion of the delivery device may be advanced into the body to advance and position the grasper within the body.

Once the grasper is positioned in the body, it may be releasably connected to tissue. To connect the grasper to tissue, the grasper may first be placed in an open configuration. In some variations, the grasper may be placed in an open configuration using the delivery device carrying the grasper, as described with respect to each system herein. With the grasper in the open configuration, the grasper may be manipulated to position the tissue between the first jaw and the second jaw. The grasper may be returned to a closed configuration. The grasper may then be released from the delivery device, which may be removed from the body in some variations. With the grasper releasably connected to the tissue, a magnetic control element comprising one or more magnets may be positioned externally of the body and may magnetically attract the grasper to reposition and/or hold the grasper.

In some instances it may be desirable to detach the grasper from the tissue. For example, in some instances it may be desirable to attach the grasper to a different portion of the tissue. In these instances, the grasper may be detached from the tissue using a delivery device to return the grasper to an open configuration. The grasper may be repositioned to again place tissue between the jaws of the grasper, and the grasper may then be placed in the closed configuration to reattach the grasper to tissue. In other instances, the grasper may be detached from the tissue, and removed from the body.

We claim:

1. A system for manipulating tissue, comprising:
    a grasper comprising two arms configured to be attached to tissue in a body of a patient, wherein the two arms are connected via a linkage assembly comprising at least one pivot joint, wherein the linkage assembly is connected to a coupling element, and wherein the two arms can be moved from a closed configuration to an open configuration by releasably engaging an actuation rod with the coupling element via a magnetic force and proximally retracting the actuation rod;
    a delivery device comprising the actuation rod, the delivery device configured to releasably engage the grasper and to actuate the grasper between the closed configuration and the open configuration; and
    a magnetic control assembly comprising a magnet configured to generate a magnetic field and to apply a magnetic force to the grasper.

2. The system of claim 1, wherein the grasper comprises a magnetic or ferromagnetic material.

3. The system of claim 1, wherein the two arms are configured to attach to tissue by holding the tissue between the two arms.

4. The system of claim 1, wherein the two arms are connected via the linkage assembly having an expanded configuration and a collapsed configuration and comprising a plurality of struts.

5. The system of claim 4, wherein the two arms can be moved from the open configuration to the closed configuration by moving the linkage assembly from the collapsed configuration to the expanded configuration.

6. The system of claim 1, wherein the at least one pivot joint comprises a first pivot joint and a second pivot joint.

7. The system of claim 1, wherein the linkage assembly comprises one or more straight strut and one or more bent strut.

8. The system of claim 1, wherein the coupling element comprises a distal end connected to the linkage assembly and a proximal end configured to be releasably engaged by the actuation rod.

9. The system of claim 1, wherein the coupling element comprises magnetic material.

10. A system for manipulating tissue, comprising:
    a grasper comprising two arms configured to be attached to tissue in a body of a patient, wherein the two arms are connected via a first pivot joint of a linkage assembly, wherein the linkage assembly is connected to a coupling element via a second pivot joint of the linkage assembly, and wherein the two arms can be moved from a closed configuration to an open configuration by moving the linkage assembly from an expanded configuration to a collapsed configuration;
    a delivery device comprising an outer sheath defining a lumen, the delivery device configured to releasably engage the grasper and to actuate the grasper between the closed configuration and the open configuration; and
    a magnetic control assembly comprising a magnet configured to generate a magnetic field and to apply a magnetic force to the grasper.

11. The system of claim 10, wherein the outer sheath comprises a distal lip with a tapered shape.

12. The system of claim 10, wherein the outer sheath comprises a distal lip with a funnel shape.

13. The system of claim 10, wherein a diameter of the outer sheath decreases from a distal end to a proximal end of the delivery device.

14. The system of claim 10, wherein the grasper is configured to actuate between the closed configuration and the open configuration by translating the linkage assembly through the lumen.

15. The system of claim 10, wherein the delivery device comprises an actuation rod.

* * * * *